(12) United States Patent
Kim et al.

(10) Patent No.: US 9,150,496 B2
(45) Date of Patent: Oct. 6, 2015

(54) CONDENSED-CYCLIC COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Soo-Yon Kim, Yongin-si (KR); Seok-Hwan Hwang, Yongin-si (KR); Young-Kook Kim, Yongin-si (KR); Hye-Jin Jung, Yongin-si (KR); Jin-O Lim, Yongin-si (KR); Sang-Hyun Han, Yongin-si (KR); Eun-Jae Jeong, Yongin-si (KR); Jun-Ha Park, Yongin-si (KR); Eun-Young Lee, Yongin-si (KR); Bo-Ra Lee, Yongin-si (KR); Jong-Hyuk Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 394 days.

(21) Appl. No.: 13/677,255

(22) Filed: Nov. 14, 2012

(65) Prior Publication Data

US 2014/0027721 A1    Jan. 30, 2014

(30) Foreign Application Priority Data

Jul. 25, 2012    (KR) ........................ 10-2012-0081403

(51) Int. Cl.
*C07C 211/61* (2006.01)
*H01L 51/00* (2006.01)
(Continued)

(52) U.S. Cl.
CPC ................ *C07C 211/61* (2013.01); *C07B 59/00* (2013.01); *C07C 211/54* (2013.01);
(Continued)

(58) Field of Classification Search
CPC .. C07C 211/54; C07C 211/56; C07C 211/58; C07C 211/60; C07C 211/61; C07C 255/58; C07D 209/86; C07D 209/88; C07D 213/74; C07D 307/91; C07D 333/76; C09K 11/06; C09K 2211/1007; C09K 2211/1011; C09K 2211/1029; C09K 2211/1088; C09K 2211/1092; H01L 51/0032; H01L 51/0054; H01L 51/006; H01L 51/50; H05B 33/14
See application file for complete search history.

(56) References Cited

U.S. PATENT DOCUMENTS 7,053,255 B2    5/2006    Ikeda et al.
7,233,019 B2    6/2007    Ionkin et al.
(Continued)

FOREIGN PATENT DOCUMENTS

JP    2006-273737 A    10/2006
KR    10-2006-0006760    1/2006
(Continued)

*Primary Examiner* — Dawn Garrett
(74) *Attorney, Agent, or Firm* — Christie, Parker & Hale, LLP

(57) ABSTRACT

Embodiments of the invention are directed to a condensed-cyclic compound represented by Formula 1, and to an organic light-emitting device including the condensed-cyclic compound.

The organic light-emitting device may include an organic layer containing the condensed-cyclic compound.

20 Claims, 1 Drawing Sheet

Formula 1

(51) Int. Cl.

| | | |
|---|---|---|
| *C07C 211/54* | (2006.01) | |
| *C07C 211/60* | (2006.01) | |
| *C07C 211/58* | (2006.01) | |
| *C07C 255/58* | (2006.01) | |
| *C07D 333/76* | (2006.01) | |
| *C07C 211/56* | (2006.01) | |
| *C07D 209/86* | (2006.01) | |
| *C07D 209/88* | (2006.01) | |
| *C07D 307/91* | (2006.01) | |
| *C09K 11/06* | (2006.01) | |
| *H05B 33/14* | (2006.01) | |
| *C07B 59/00* | (2006.01) | |

(52) U.S. Cl.
CPC ............ *C07C 211/56* (2013.01); *C07C 211/58* (2013.01); *C07C 211/60* (2013.01); *C07C 255/58* (2013.01); *C07D 209/86* (2013.01); *C07D 209/88* (2013.01); *C07D 307/91* (2013.01); *C07D 333/76* (2013.01); *C09K 11/06* (2013.01); *H01L 51/006* (2013.01); *H01L 51/0032* (2013.01); *H05B 33/14* (2013.01); *C07C 2101/14* (2013.01); *C07C 2102/08* (2013.01); *C07C 2103/18* (2013.01); *C07C 2103/24* (2013.01); *C07C 2103/26* (2013.01); *C07C 2103/40* (2013.01); *C07C 2103/50* (2013.01); *C07C 2103/94* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *H01L 51/0054* (2013.01)

(56) References Cited

U.S. PATENT DOCUMENTS

| | | |
|---|---|---|
| 2005/0156164 A1 | 7/2005 | Sotoyama |
| 2009/0085468 A1 | 4/2009 | Funahashi et al. |
| 2009/0230854 A1 | 9/2009 | Kim et al. |
| 2010/0187511 A1 | 7/2010 | Funahashi et al. |

FOREIGN PATENT DOCUMENTS

| | | |
|---|---|---|
| KR | 10-2006-0111048 | 10/2006 |
| KR | 10-2008-0068862 | 7/2008 |
| KR | 10-2009-0085939 A | 8/2009 |
| KR | 10-2009-0093674 A | 9/2009 |
| KR | 10-2009-0098589 | 9/2009 |
| KR | 10-2010-0017849 | 2/2010 |
| WO | WO 2006/112582 A1 | 10/2006 |

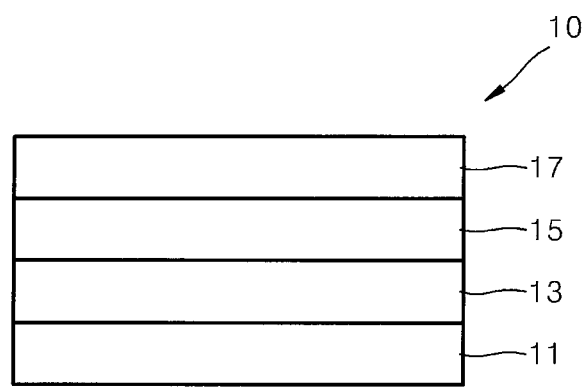

CONDENSED-CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2012-0081403, filed on Jul. 25, 2012 in the Korean Intellectual Property Office, the entire content of which is incorporated herein by reference.

BACKGROUND

1. Technical Field

The present invention relates to a condensed-cyclic compound and an organic light-emitting device including the condensed-cyclic compound.

2. Description of the Related Art

Organic light-emitting devices (OLEDs) are self-emitting devices having advantages such as wide viewing angles, good contrast, quick response speeds, high brightness, and good driving voltage characteristics. Additionally, OLEDs can provide multicolored images.

A typical OLED has a structure including a substrate on which is sequentially stacked an anode, a hole transport layer (HTL), an emission layer (EML), an electron transport layer (ETL), and a cathode. In this regard, the HTL, the EML, and the ETL are organic thin films formed of organic compounds.

The operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is a demand an emission layer material, and in particular, a material for a blue emission layer, with high color purity and improved lifetime.

SUMMARY

Embodiments of the present invention provide a condensed-cyclic compound for an organic light-emitting device with low voltage, high luminance, high efficiency, and a long lifespan. Other embodiments provide an organic light-emitting device including an organic layer containing the condensed-cyclic compound.

According to an aspect of the present invention, a condensed-cyclic compound is represented by Formula 1 below.

Formula 1

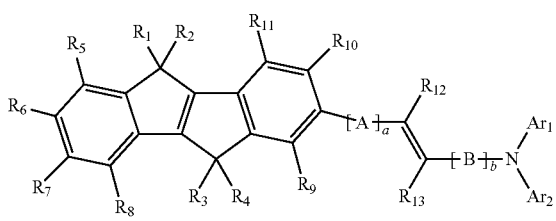

In Formula 1, $Ar_1$ and $Ar_2$ are each independently a substituted or unsubstituted $C_5$-$C_{40}$ aryl group or a substituted or unsubstituted $C_3$-$C_{40}$ heteroaryl group. N, $Ar_1$ and $Ar_2$ may optionally combine to form a substituted or unsubstituted $C_5$-$C_{20}$ heteroaryl group.

A and B are each a divalent linker, and are each independently one of a substituted or unsubstituted $C_5$-$C_{40}$ arylene group, or a substituted or unsubstituted $C_3$-$C_{40}$ heteroarylene group.

a is an integer from 0 to 3, and b is an integer from 0 to 3. If a is 2 or greater, the two or more A groups may be identical to or different from each other. Similarly, if b is 2 or greater, the two or more B groups may be identical to or different from each other.

$R_1$ to $R_{13}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_2$-$C_{40}$ cycloalkenyl group, a substituted or unsubstituted $C_5$-$C_{40}$ aryl group, a substituted or unsubstituted $C_2$-$C_{40}$ heteroaryl group, a substituted or unsubstituted $C_5$-$C_{40}$ aryloxy group, a substituted or unsubstituted $C_5$-$C_{40}$ arylthio group, —Si($R_{31}$)($R_{32}$)($R_{33}$), or —N($R_{34}$)($R_{35}$).

$R_{31}$ and $R_{35}$ are each independently a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_5$-$C_{40}$ aryl group, a substituted or unsubstituted $C_5$-$C_{40}$ aryloxy group, a substituted or unsubstituted $C_5$-$C_{40}$ arylthio group, or a substituted or unsubstituted $C_2$-$C_{40}$ heteroaryl group.

According to another aspect of the present invention, an organic light-emitting device includes a first electrode, a second electrode facing the first electrode, and an organic layer between the first electrode and the second electrode. The organic layer includes at least one layer, and comprises at least one of the above-described condensed-cyclic compounds.

BRIEF DESCRIPTION OF THE DRAWING

The above and other features and advantages of the present invention will become more apparent by reference to the following detailed description in conjunction with the attached drawing in which:

FIG. 1 is a schematic diagram of the structure of an organic light-emitting device according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, a condensed-cyclic compound is represented by Formula 1.

Formula 1

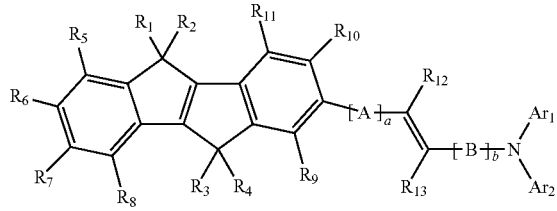

In Formula 1, $Ar_1$ and $Ar_2$ are each independently a substituted or unsubstituted $C_5$-$C_{40}$ aryl group or a substituted or unsubstituted $C_3$-$C_{40}$ heteroaryl group. N, $Ar_1$ and $Ar_2$ may optionally combine to form a substituted or unsubstituted $C_5$-$C_{20}$ heteroaryl group.

A and B are each a divalent linker, and are each independently one of a substituted or unsubstituted $C_5$-$C_{40}$ arylene group, or a substituted or unsubstituted $C_3$-$C_{40}$ heteroarylene group.

a is an integer from 0 to 3, and b is an integer from 0 to 3. If a is 2 or greater, the two or more A groups may be identical to or different from each other. Similarly, if b is 2 or greater, the two or more B groups may be identical to or different from each other.

$R_1$ to $R_{13}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_2$-$C_{40}$ cycloalkenyl group, a substituted or unsubstituted $C_5$-$C_{40}$ aryl group, a substituted or unsubstituted $C_2$-$C_{40}$ heteroaryl group, a substituted or unsubstituted $C_5$-$C_{40}$ aryloxy group, a substituted or unsubstituted $C_5$-$C_{40}$ arylthio group, —Si($R_{31}$)($R_{32}$)($R_{33}$), or —N($R_{34}$)($R_{35}$).

$R_{31}$ and $R_{35}$ are each independently a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_5$-$C_{40}$ aryl group, a substituted or unsubstituted $C_5$-$C_{40}$ aryloxy group, a substituted or unsubstituted $C_5$-$C_{40}$ arylthio group, or a substituted or unsubstituted $C_2$-$C_{40}$ heteroaryl group.

For example, $Ar_1$ and $Ar_2$ may be each independently one of a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted phenanthrenyl group, a substituted or unsubstituted pyranyl group, a substituted or unsubstituted pyridyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted imidazopyridyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolyl group, a substituted or unsubstituted pyridoindolyl group, a substituted or unsubstituted indazolyl group, a substituted or unsubstituted carbazolyl group, a substituted or unsubstituted purinyl group, a substituted or unsubstituted benzoquinolyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furyl group, a substituted or unsubstituted benzofuryl group, a substituted or unsubstituted dibenzofuryl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, or a substituted or unsubstituted tetrazolyl group.

For example, $Ar_1$ and $Ar_2$ may be each independently one of the groups represented by Formulae 2A to 2H below, but are not limited thereto.

Formula 2A

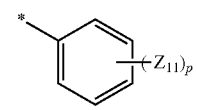

Formula 2B

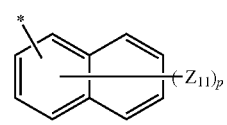

Formula 2C

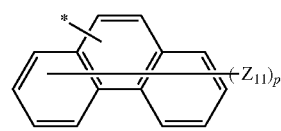

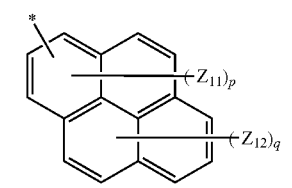
Formula 2D

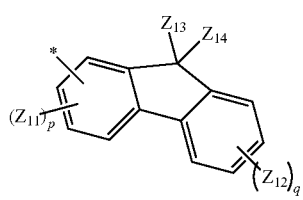
Formula 2E

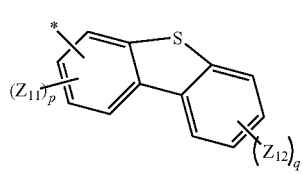
Formula 2F

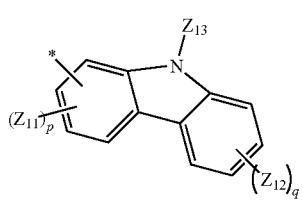
Formula 2G

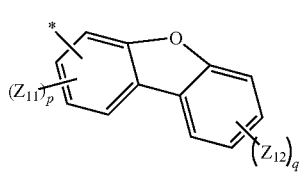
Formula 2H

In Formulae 2A to 2H, $Z_{11}$, $Z_{12}$, $Z_{13}$, and $Z_{14}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridyl group, a substituted or unsubstituted fluorenyl group, or a substituted or unsubstituted quinolyl group. $Z_{13}$ and $Z_{14}$ (linked to the same carbon atom) may optionally combine together to form a substituted or unsubstituted $C_5$-$C_{20}$ aryl group. A plurality of each of $Z_{11}$, $Z_{12}$, $Z_{13}$ and $Z_{14}$ may be identical to or different from each other. p is an integer from 1 to 9, q is an integer from 1 to 5, and * indicates a binding site.

For example, $Ar_1$ and $Ar_2$ may be each independently one of the groups represented by Formulae 3A to 3W below, but are not limited thereto.

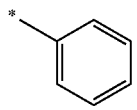
Formula 3A

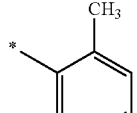
Formula 3B

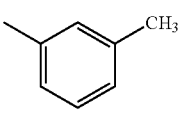
Formula 3C

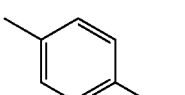
Formula 3D

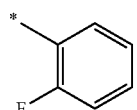
Formula 3E

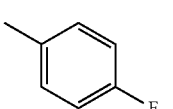
Formula 3F

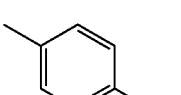
Formula 3G

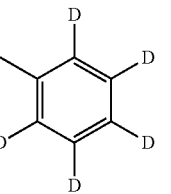
Formula 3H

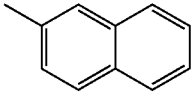
Formula 3I

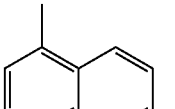
Formula 3J

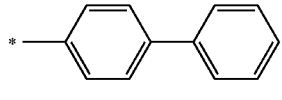
Formula 3K

Formula 3L

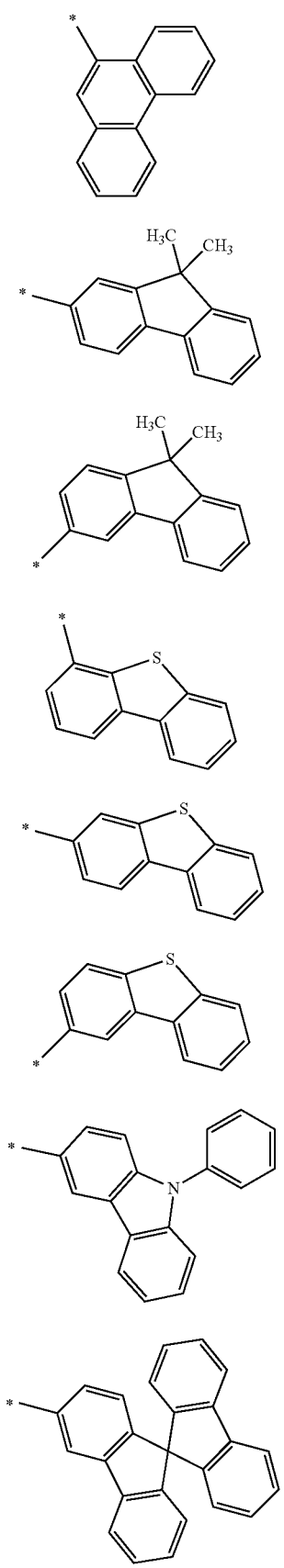

Formula 3M

Formula 3N

Formula 3O

Formula 3P

Formula 3Q

Formula 3R

Formula 3S

Formula 3T

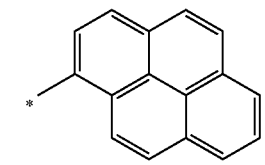

Formula 3U

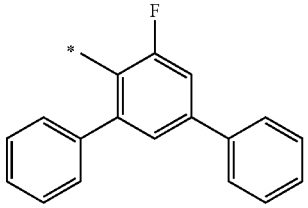

Formula 3V

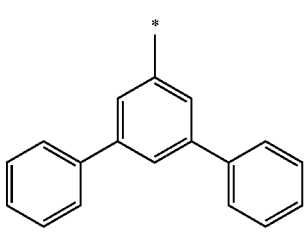

Formula 3W

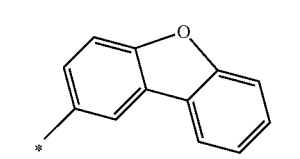

In Formulae 3A to 3W, * indicates a binding site.

A and B may be each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzofurylene group, a substituted or unsubstituted dibenzothiophenylene group, a substituted or unsubstituted pyridylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted furylene group, a substituted or unsubstituted thiophenylene group, or a substituted or unsubstituted oxadiazolylene group.

For example, A and B may be each independently one of the groups represented by Formulae 4A to 4G below, but are not limited thereto.

Formula 4A

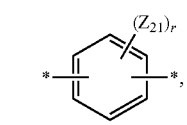

Formula 4B

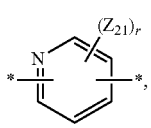

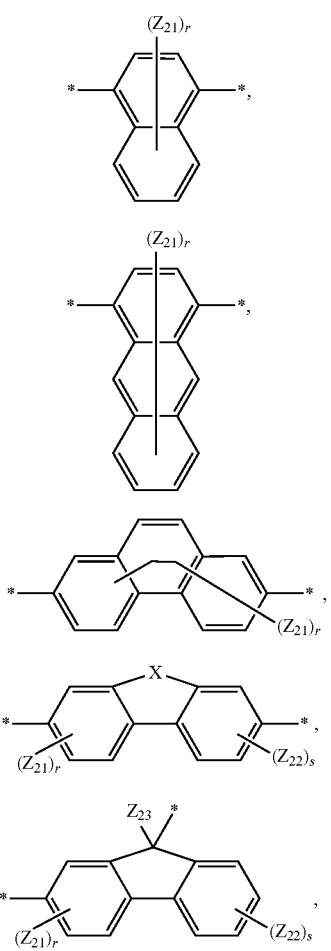

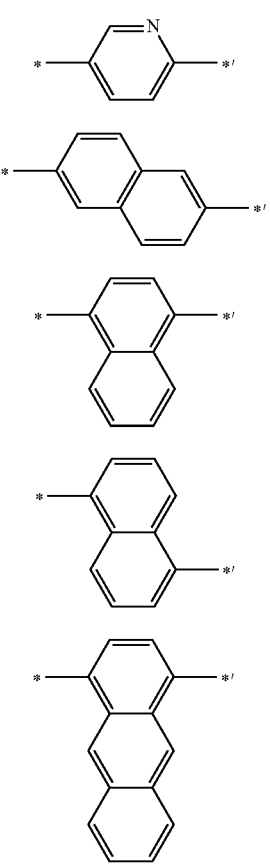

In Formulae 4A to 4G, X may be O, S, N($Z_{23}$), or C($Z_{24}$)($Z_{25}$). $Z_{21}$ to $Z_{25}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, or a substituted or unsubstituted pyridyl group. Any plurality of $Z_{21}$ and/or $Z_{22}$ may be identical to or different from each other. r is an integer from 1 to 8, s is an integer from 1 to 4, and * and *' indicate binding sites.

For example, A and B may be each independently one of the groups represented by Formulae 5A to 5N below, but are not limited thereto.

-continued

Formula 5M

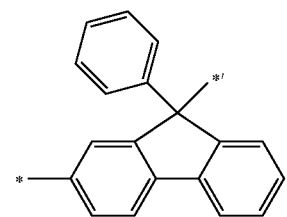

Formula 5N

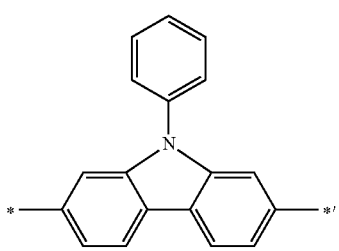

In Formulae 5A to 5N, * and *' indicate binding sites.

$R_1$ and $R_{13}$ may be each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted cyclohexyl group, a substituted or unsubstituted ethenyl group, a substituted or unsubstituted phenyl group, a substituted or unsubstituted naphthyl group, a substituted or unsubstituted fluorenyl group, a substituted or unsubstituted carbazolyl group, a substituted or unsubstituted dibenzofuryl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted perylenyl group, a substituted or unsubstituted furyl group, a substituted or unsubstituted thiophenyl group, or a substituted or unsubstituted oxadiazolyl group.

$R_1$ and $R_{13}$ may be each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, or a groups represented by one of Formulae 6A to 6F.

Formula 6A

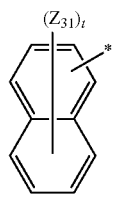

Formula 6B

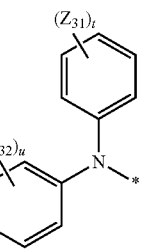

Formula 6C

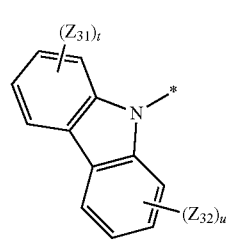

Formula 6D

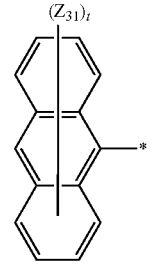

Formula 6E

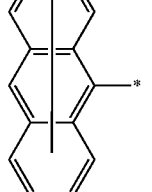

Formula 6F

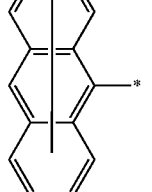

In Formulae 6A to 6F, $Z_{31}$ and $Z_{32}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, or a substituted or unsubstituted pyridyl group. Any plurality of $Z_{21}$ and/or $Z_{22}$ may be identical to or different from each other. r is an integer from 1 to 7, u is an integer from 1 to 4, and * indicates a binding site.

For example, $R_1$ and $R_{13}$ may be each independently one of a hydrogen atom, a deuterium atom, a halogen atom, a substituted or unsubstituted methyl group, a substituted or unsubstituted ethyl group, a substituted or unsubstituted propyl group, or a group represented by one of Formulae 7A to 7G below.

Formula 7A

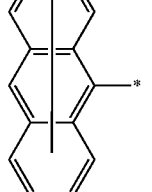

-continued

Formula 7B
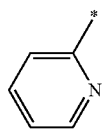

Formula 7C
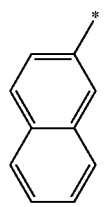

Formula 7D
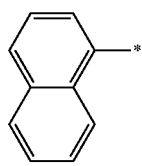

Formula 7E
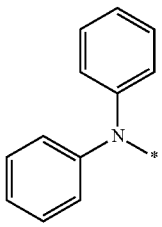

Formula 7F
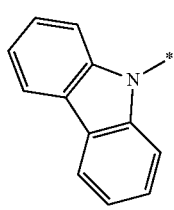

Formule 7G
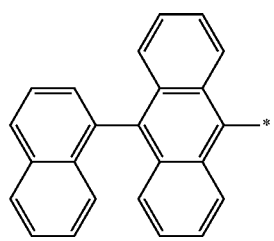

In Formulae 7A to 7G, * indicates a binding site.

In some embodiments, in the condensed-cyclic compound of Formula 1 above, $Ar_1$ and $Ar_2$ may be each independently a phenyl group; a naphthyl group; a phenanthrenyl group; a pyrenyl group; a fluorenyl group; a carbazolyl group; a dibenzothiophenyl group; or a phenyl group, a naphthyl group, a phenanthrenyl group, a pyrenyl group, a fluorenyl group, a carbazolyl group, or a dibenzothiophenyl group substituted with a deuterium atom, a halogen atom, a methyl group, or a cyano group.

A and B may be each independently a phenylene group; a naphthylene group; a pyridylene group; a phenanthrenylene group; an anthrylene group; a fluorenylene group; carbazolylene group; a dibenzothiophenylene group; a dibenzofurylene group; or a phenylene group, a naphthylene group, a pyridylene group, a phenanthrenylene group, an anthrylene group, a fluorenylene group, a carbazolylene group, a dibenzothiophenylene group, or a dibenzofurylene group substituted with a hydrogen atom, a deuterium atom, a halogen atom, a hydroxyl group, a cyano group, a nitro group, or a carboxyl group. a is an integer from 0 to 2, and b is an integer from 0 to 2. If a is 2, the two A groups may be identical to or different from each other. Similarly, if b is 2, the two B groups may be identical to or different from each other.

$R_1$ to $R_4$ may be each independently a $C_1$-$C_{10}$ alkyl group; a $C_2$-$C_{10}$ heteroaryl group; or a $C_1$-$C_{10}$ alkyl group or a $C_2$-$C_{10}$ heteroaryl group substituted with a hydrogen atom, a deuterium atom, a halogen atom or a hydroxyl group. $R_5$ to $R_{11}$ may be each independently a hydrogen atom; a deuterium atom; a halogen atom; a phenyl group; a naphthyl group; an anthryl group; a phenanthrenyl group; a pyrenyl group; a pyridyl group; a carbazolyl group; a diphenyl amino group; or a phenyl group, a naphthyl group, an anthryl group, a phenanthrenyl group, a pyrenyl group, a pyridyl group, a carbazolyl group or a diphenyl amino group substituted with a hydrogen atom, a deuterium atom, a halogen atom, or a $C_1$-$C_{30}$ aryl group. $R_{12}$ and $R_{13}$ may be each independently a hydrogen atom, a deuterium atom, a halogen atom, a phenyl group, or a naphthyl group.

For example, $R_1$ to $R_4$ may be a methyl group, a deuterated methyl group, an ethyl group, a propyl group, or a pyridyl group. $R_6$ may be a phenyl group, a naphthyl group, a pyridyl group, a carbazolyl group, or a diphenylamino group. $R_5$ and $R_7$ to $R_{11}$ may be a hydrogen atom.

The condensed-cyclic compound represented by Formula 1 above may be one of the Compounds 1 to 80 below, but is not limited thereto.

1
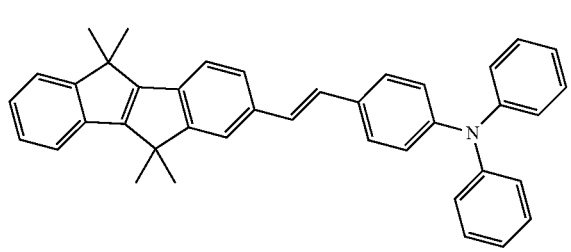

2
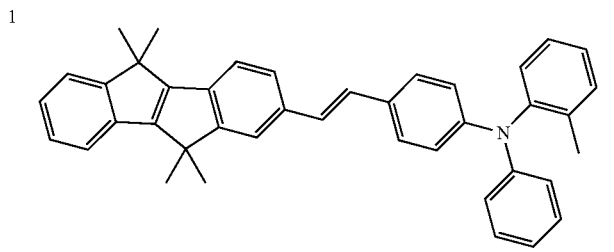

-continued
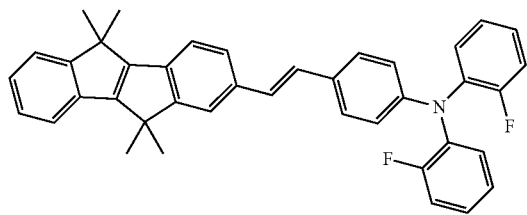
3
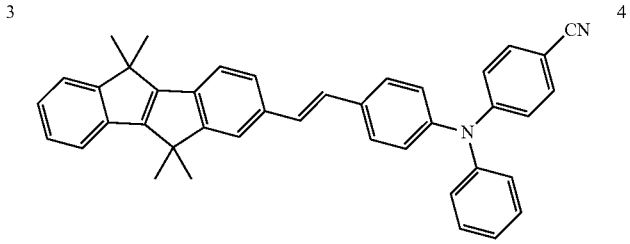
4
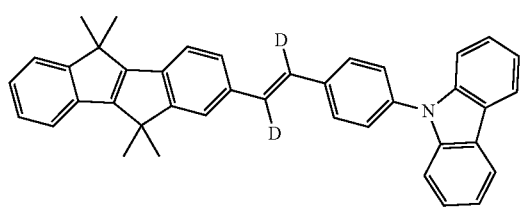
5
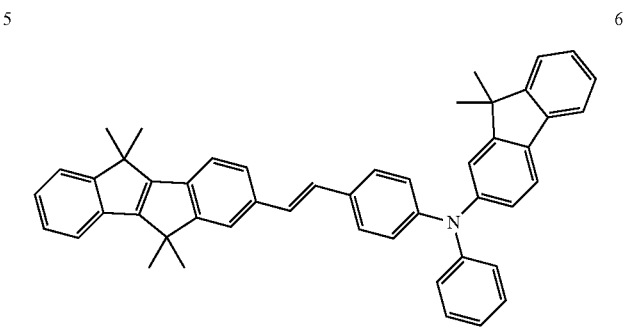
6
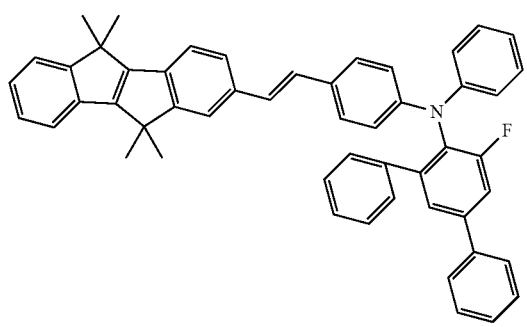
7
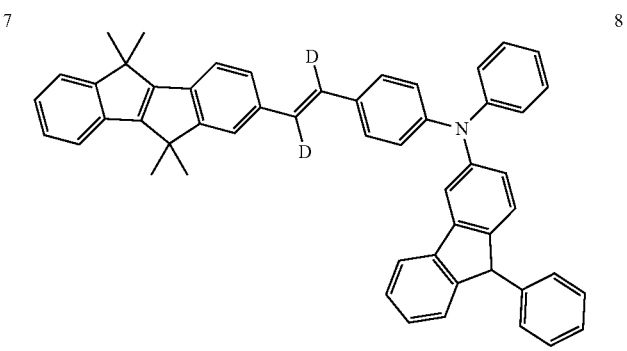
8
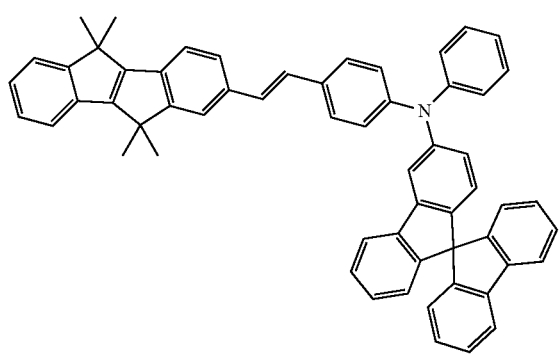
9
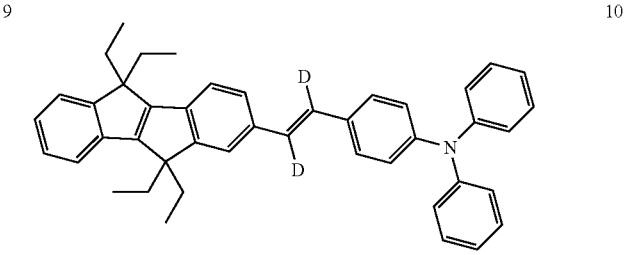
10
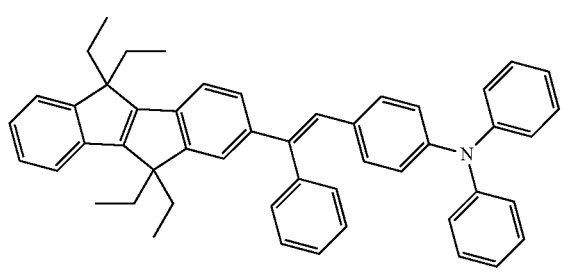
11
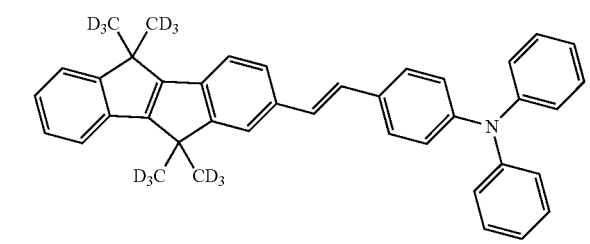
12

-continued
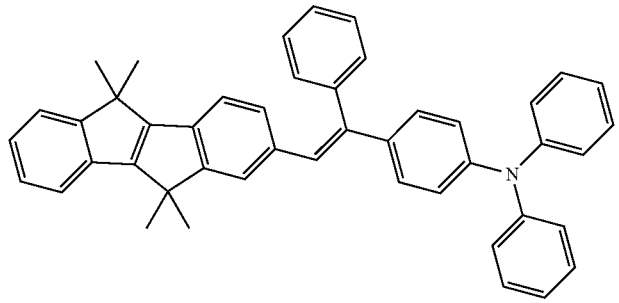
13
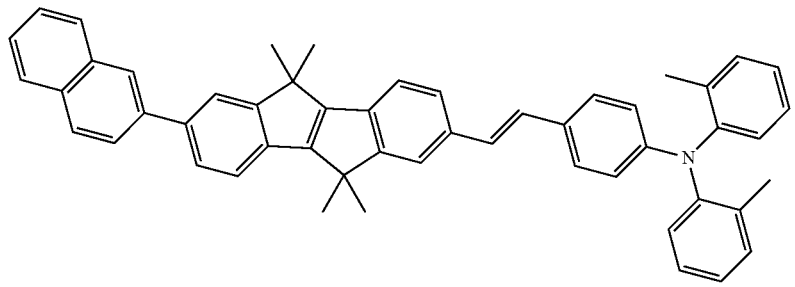
14
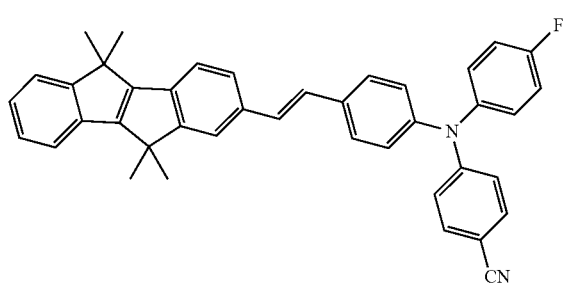
15
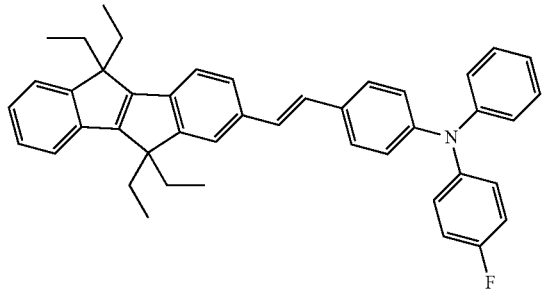
16
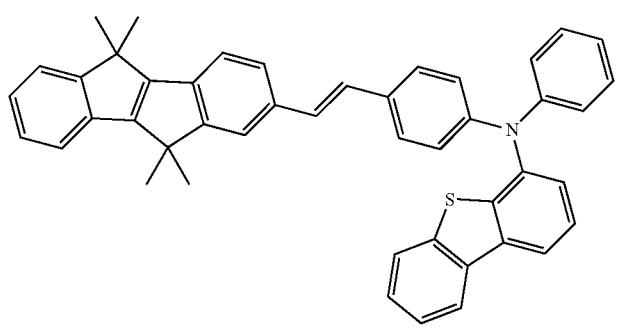
17
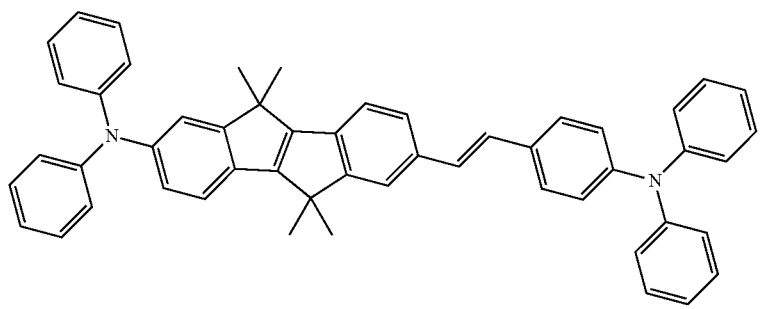
18

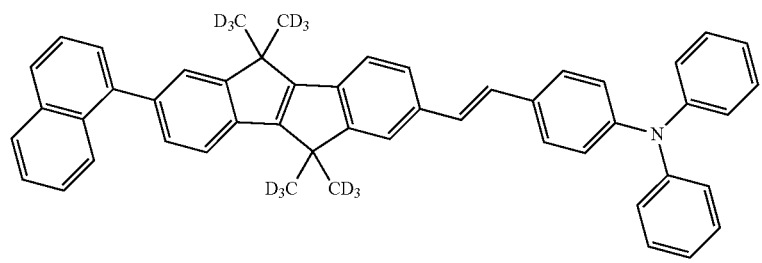
19
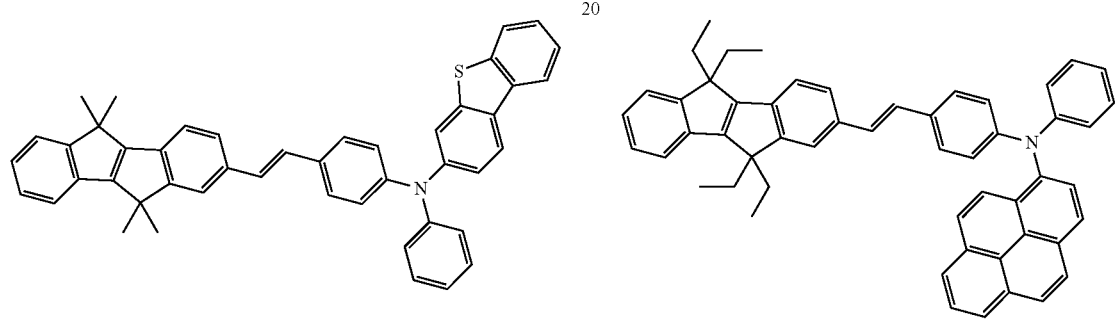
20 21
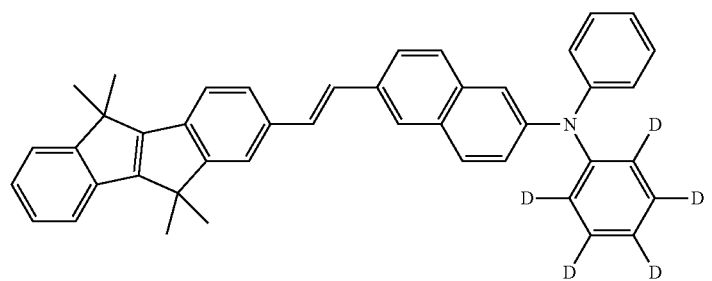
22
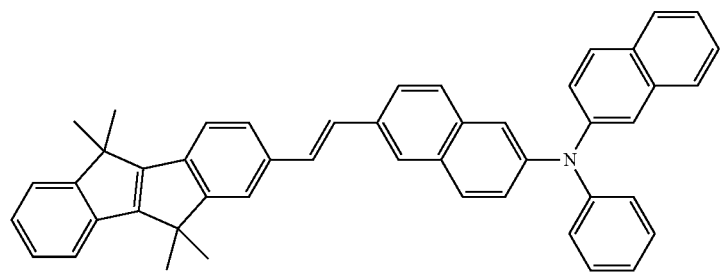
23
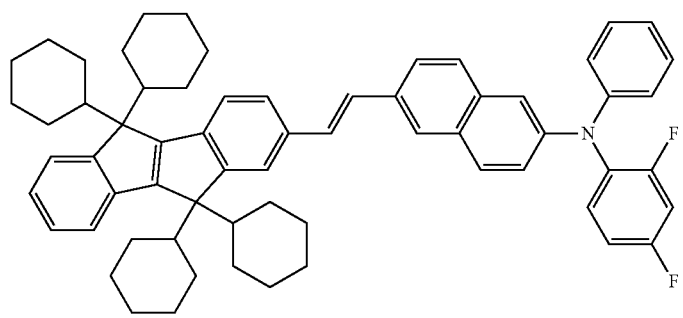
24

-continued
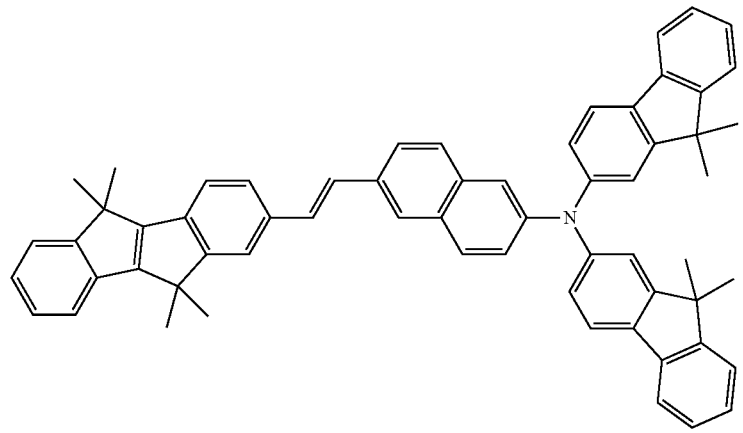
25
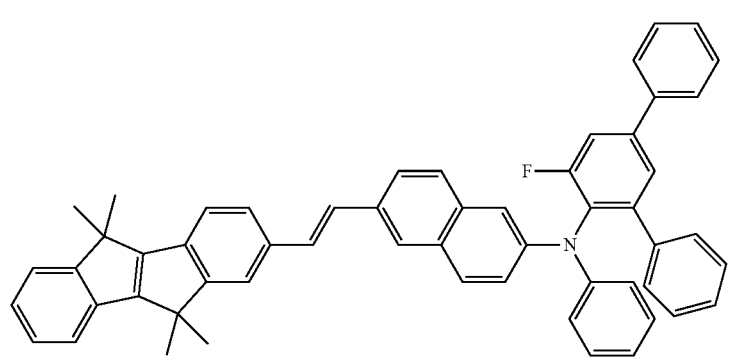
26
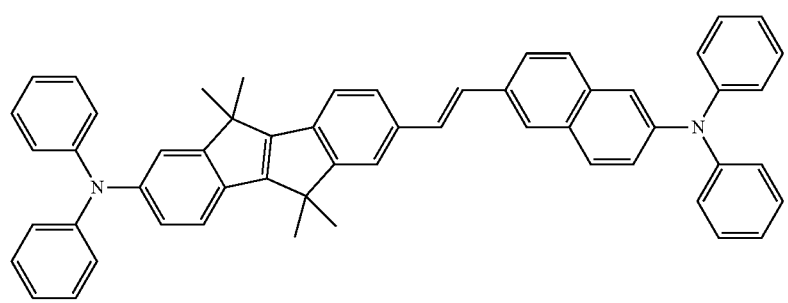
27
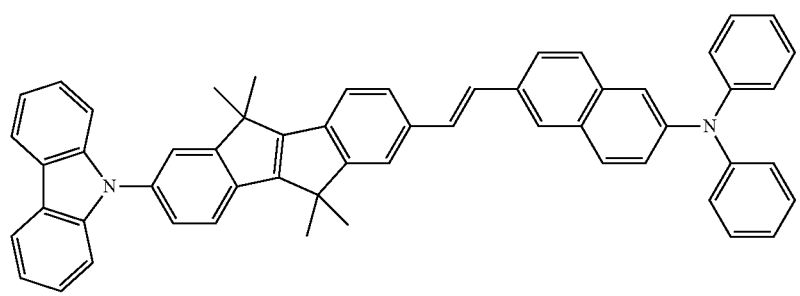
28
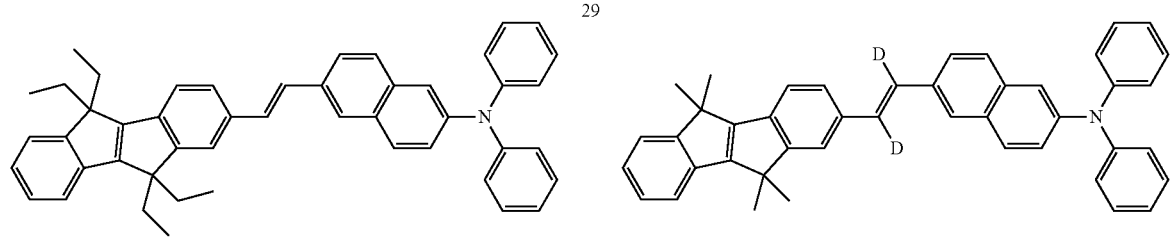
29 30

31
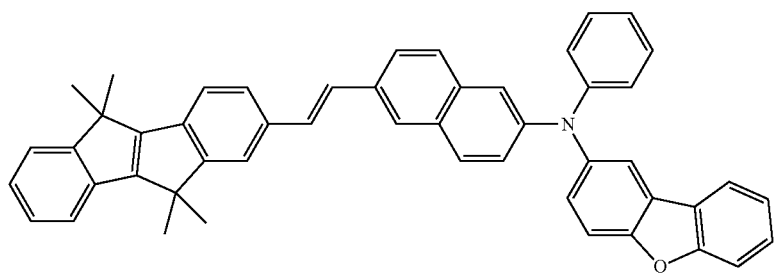
32
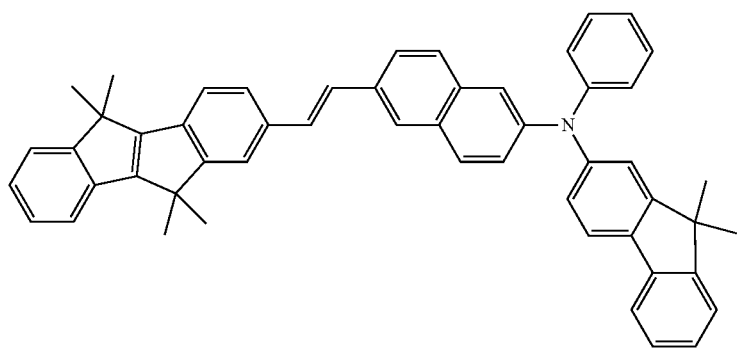
33
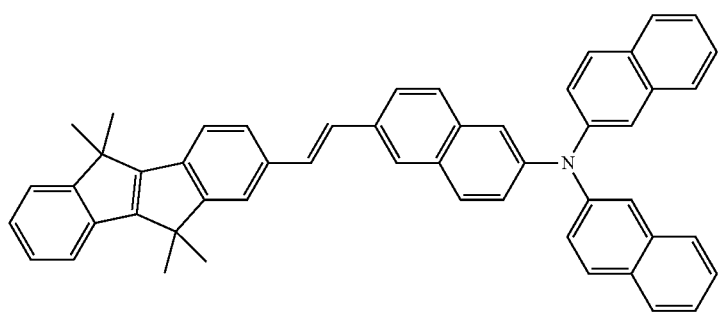
34
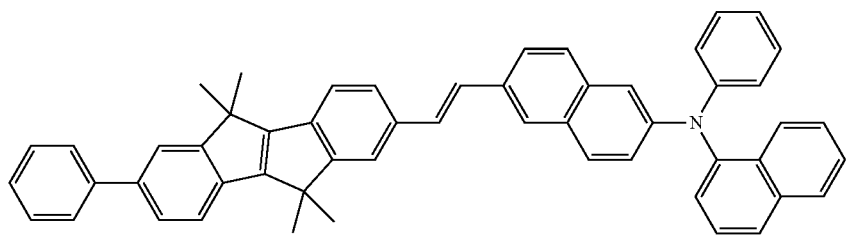
35
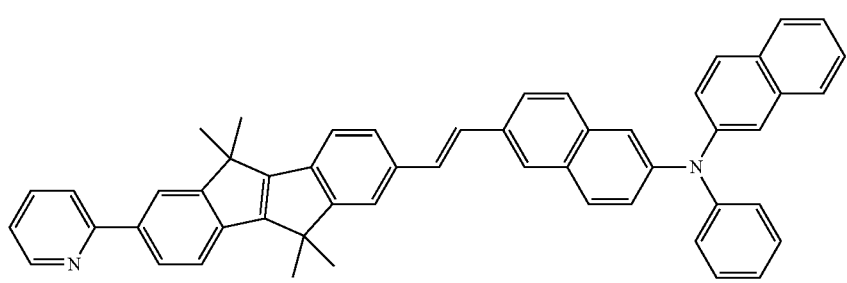

-continued
36
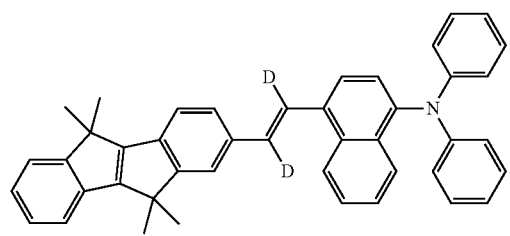
37
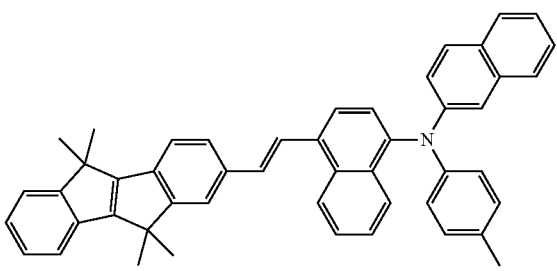
38
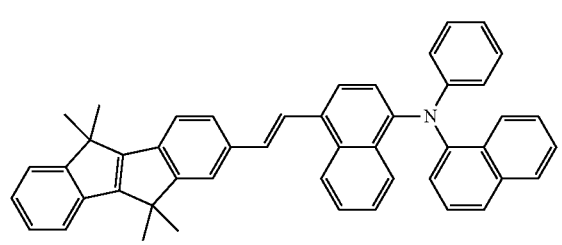
39
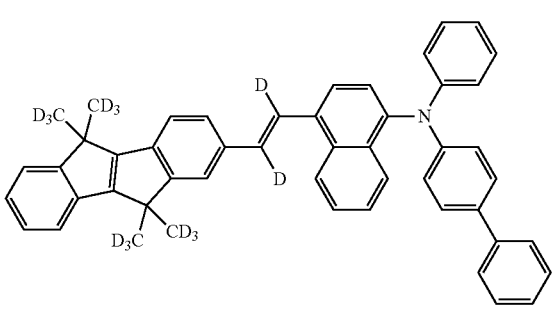
40
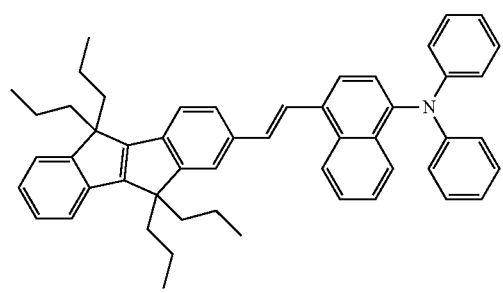
41
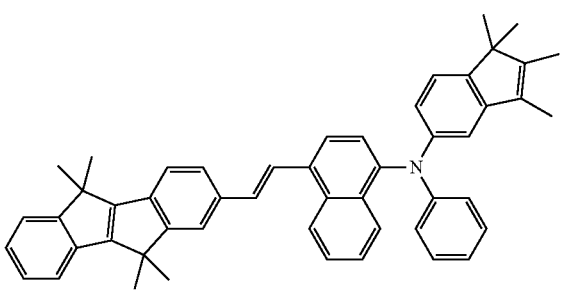
42
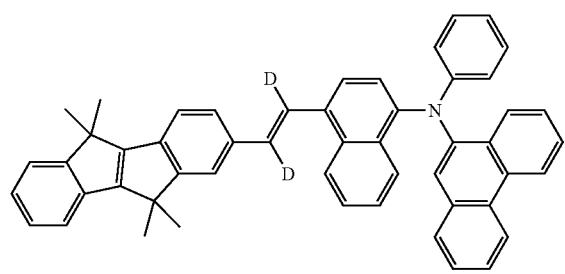
43
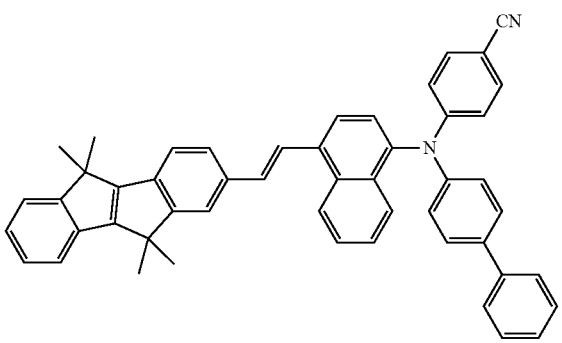
44
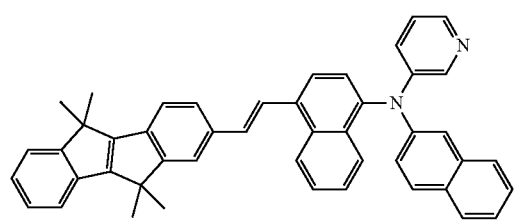
45
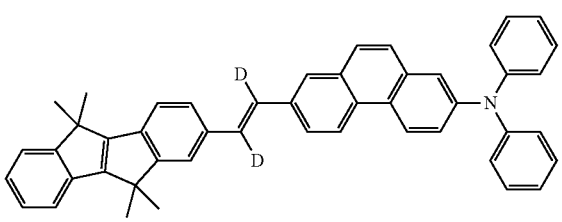

-continued
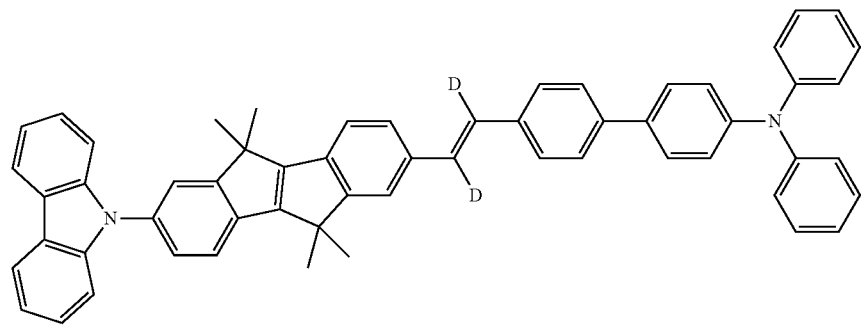
46
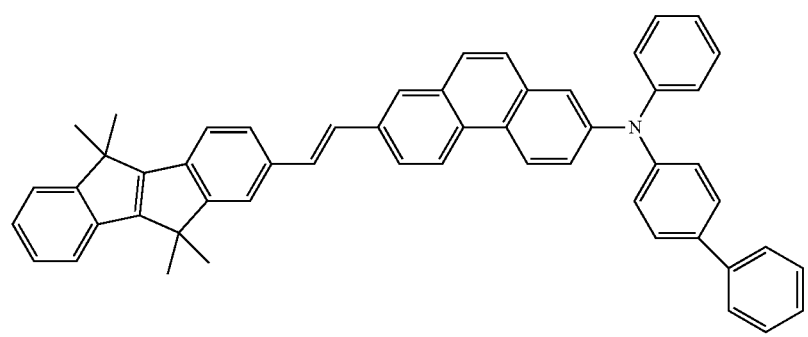
47
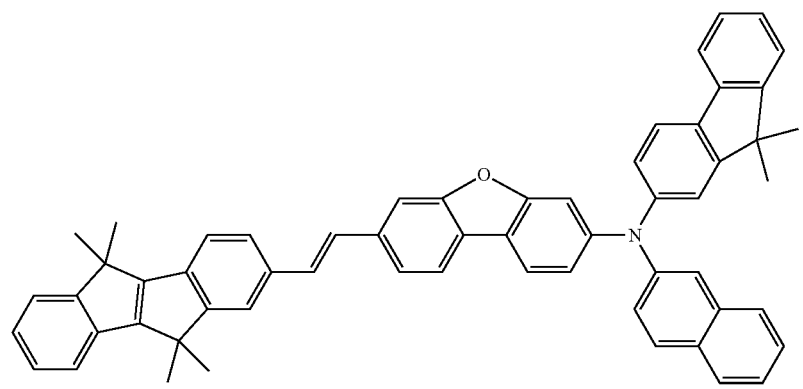
48
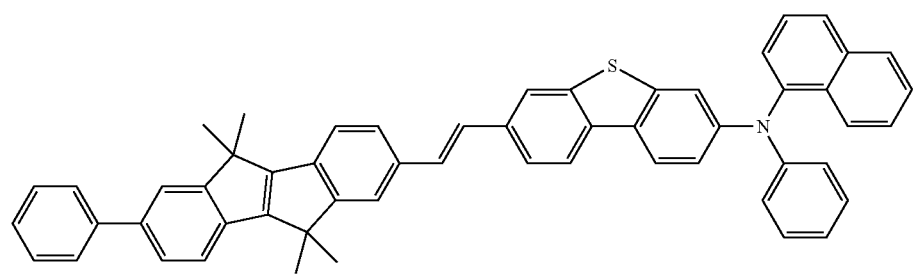
49

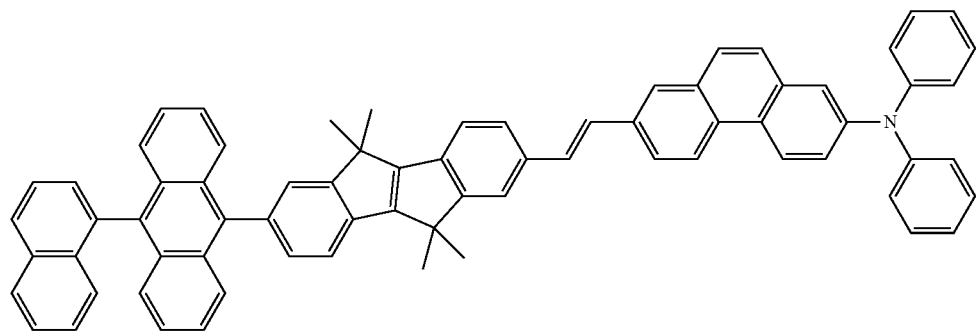
50
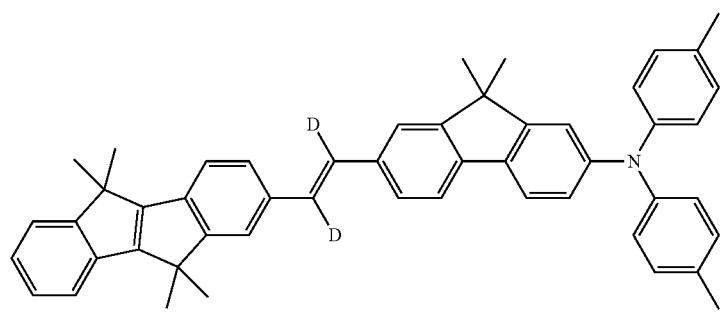
51
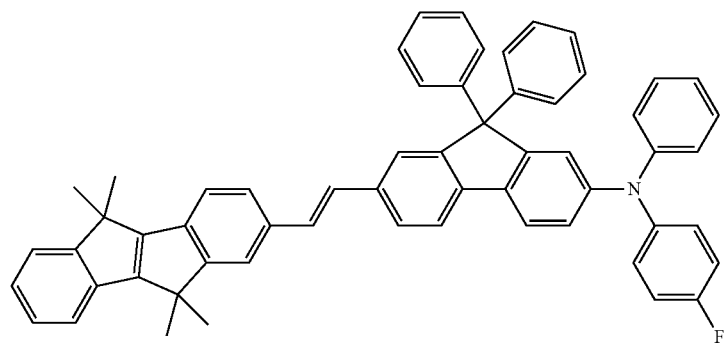
52
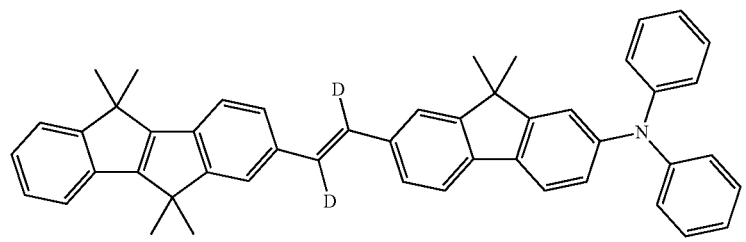
53
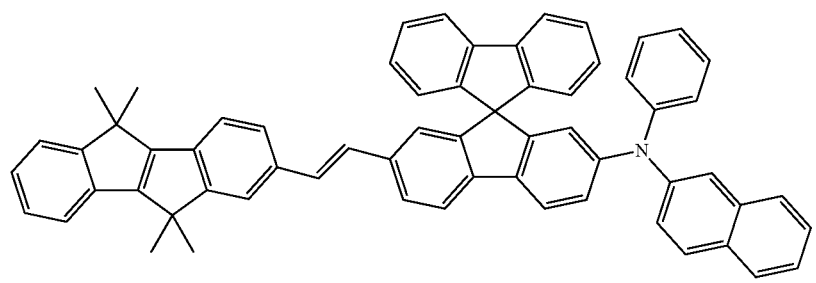
54

55
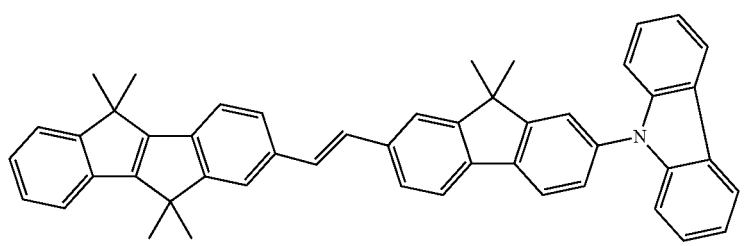
56
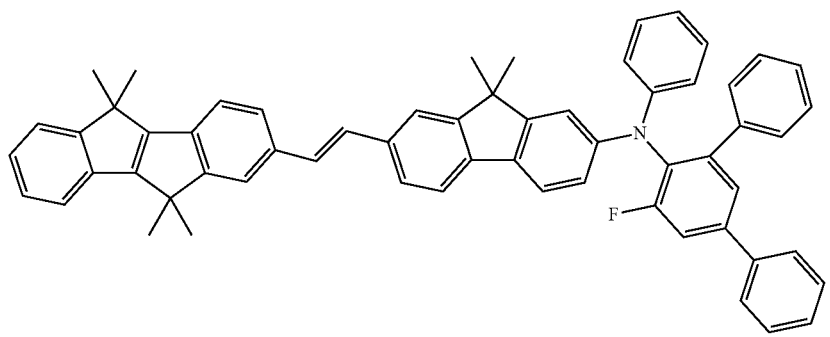
57 58
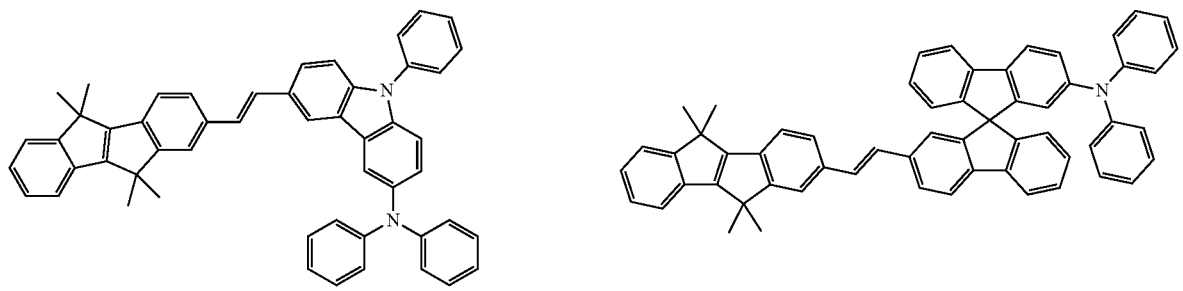
59
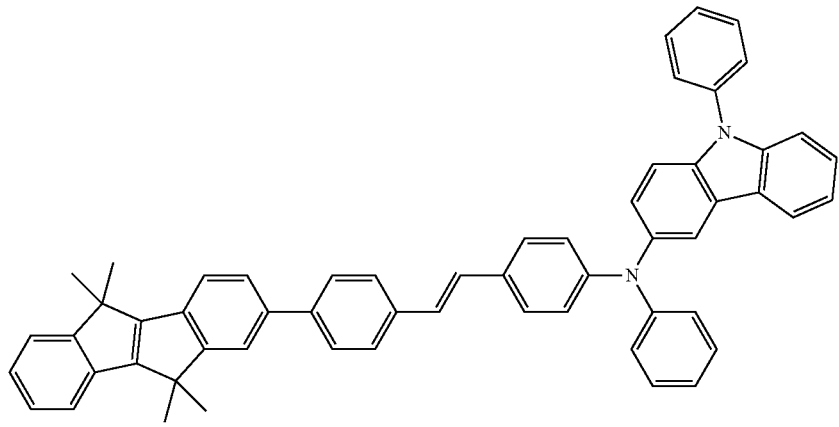

60
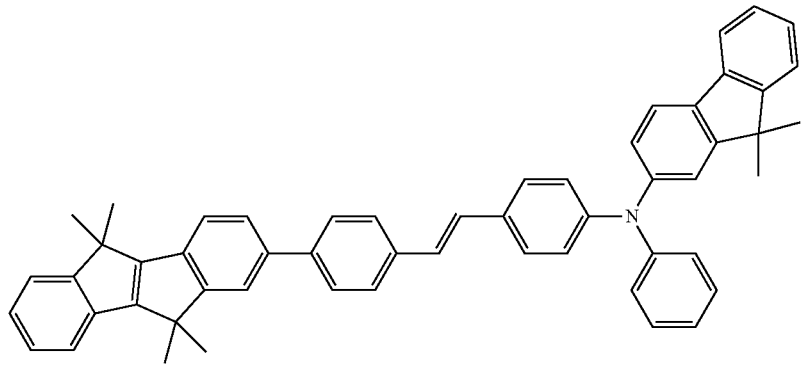
61
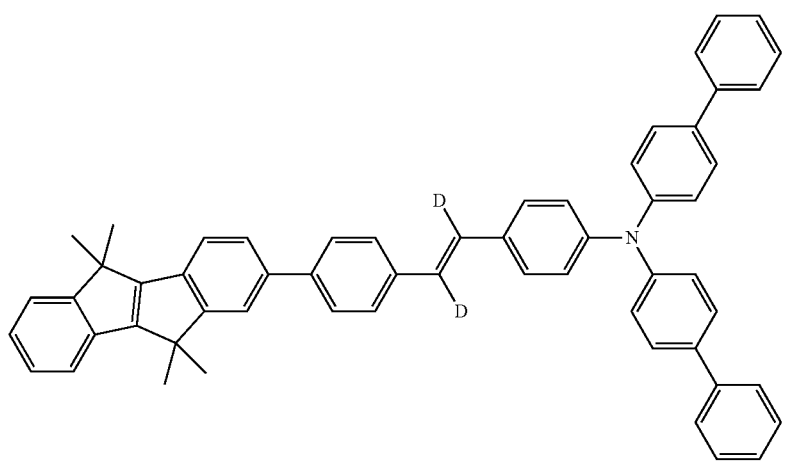
62
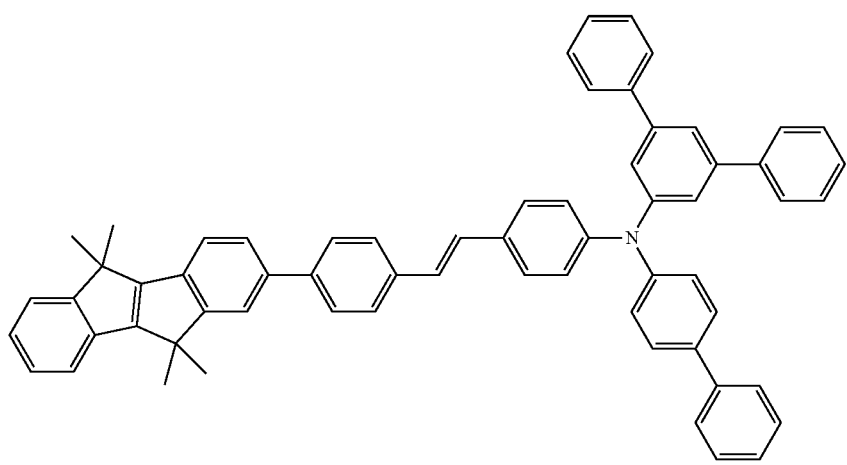
63
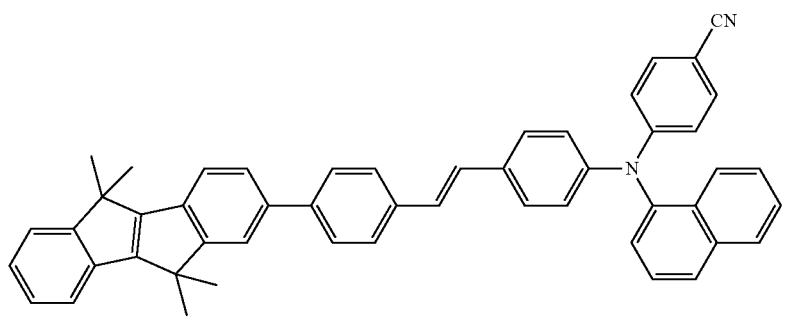

-continued
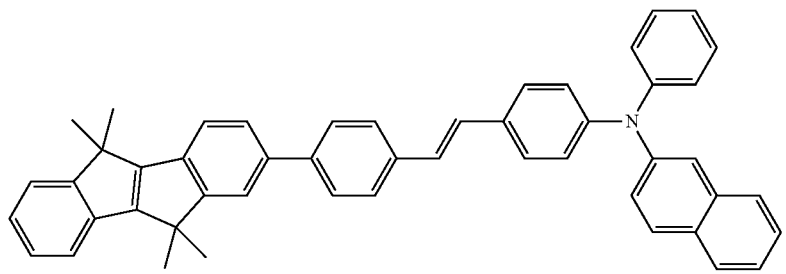
64
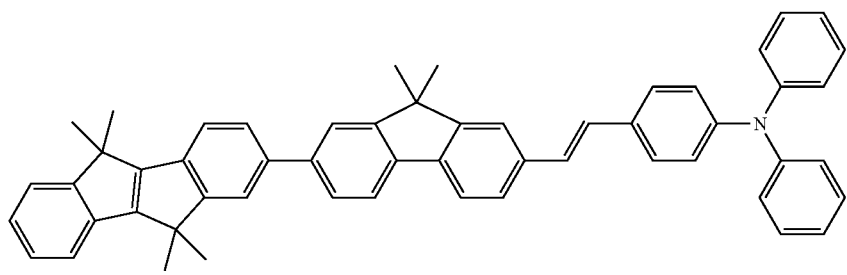
65
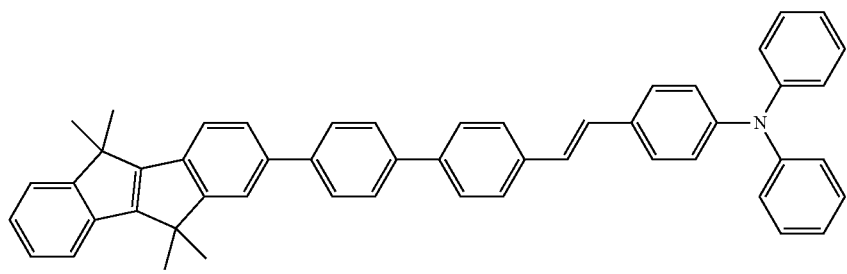
66
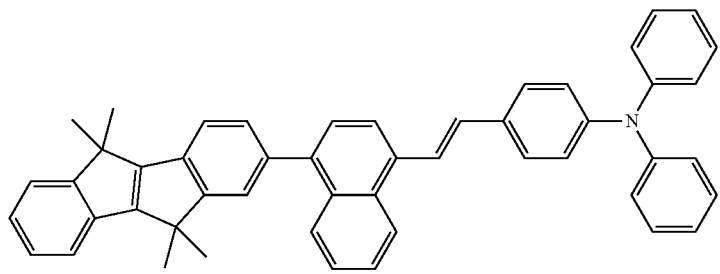
67
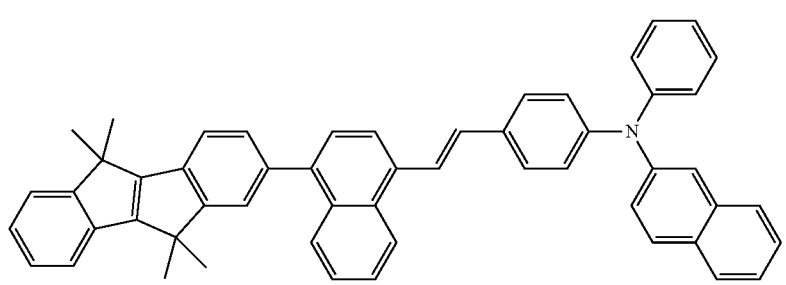
68

69
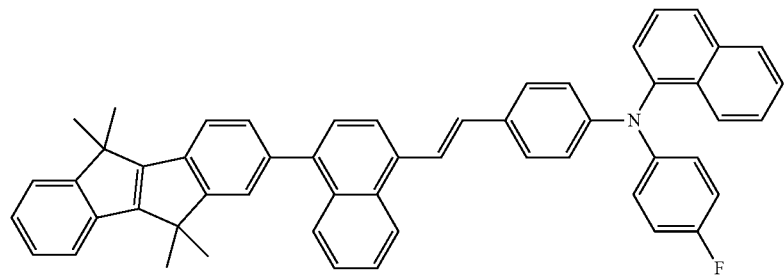
70
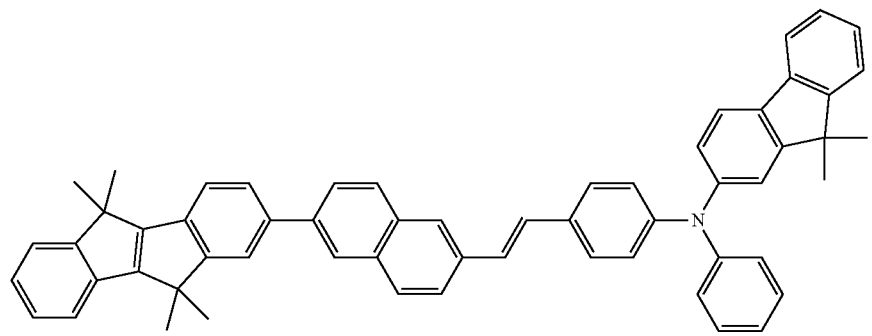
71
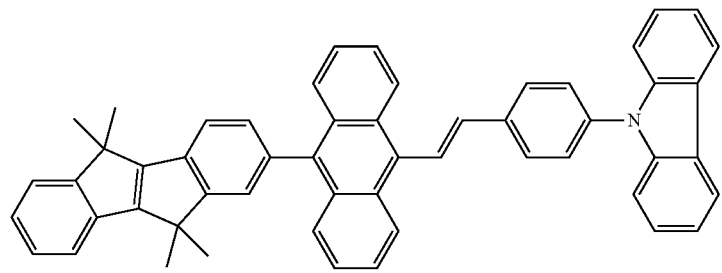
72
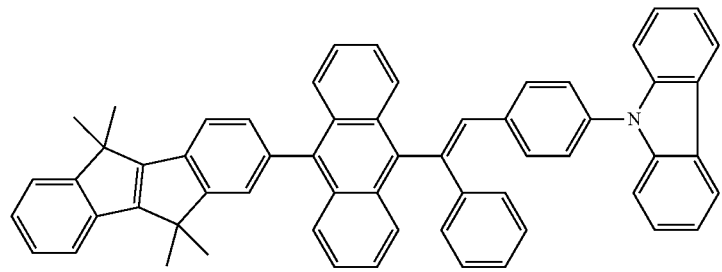
73
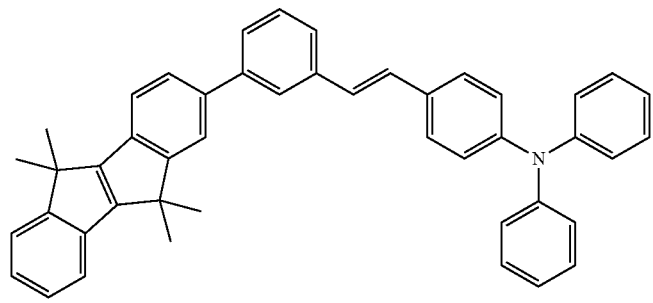

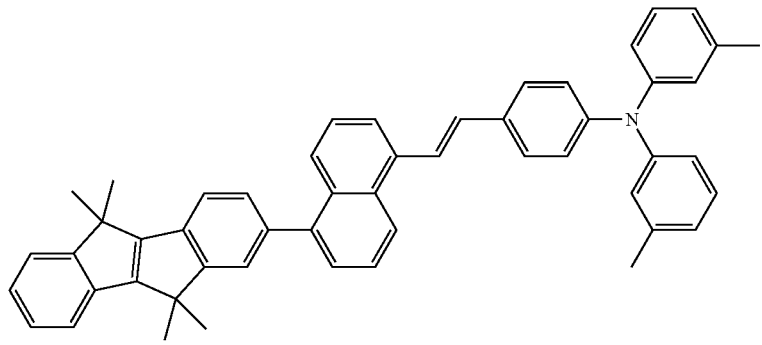
74
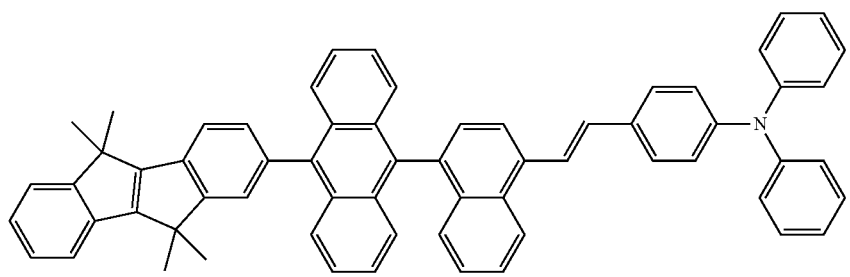
75
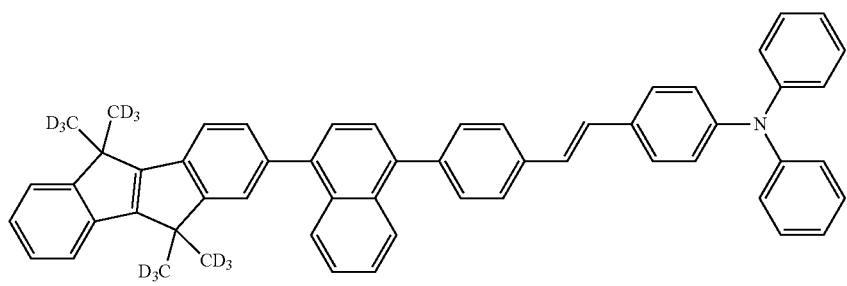
76
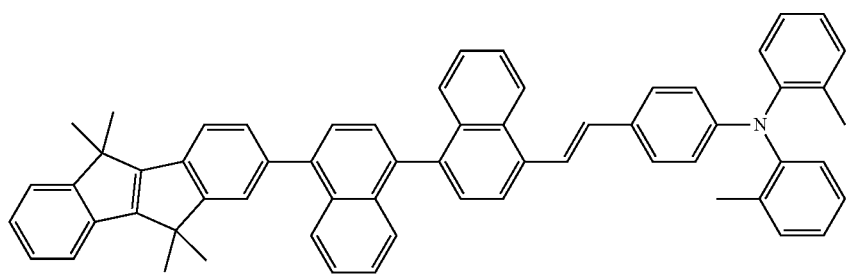
77
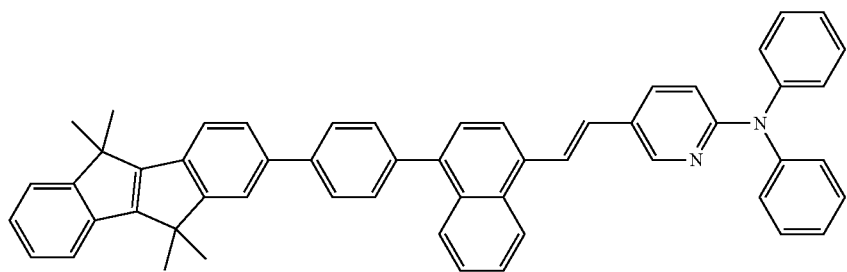
78

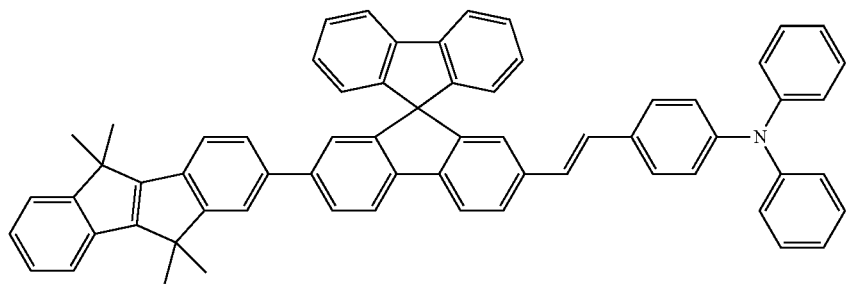

79

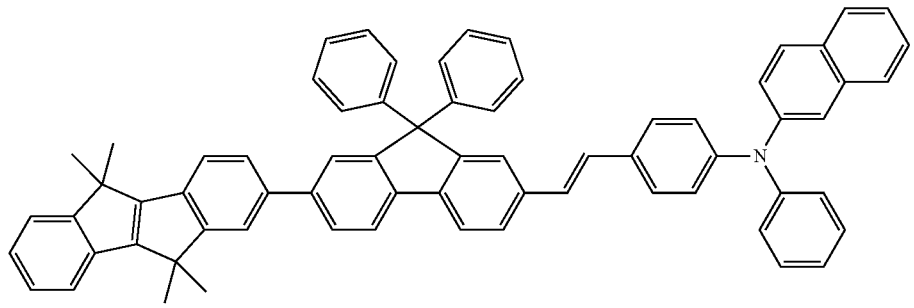

80

The condensed-cyclic compound of Formula 1 above may be used as an emitting material, a hole injecting material, and/or a hole transporting material of an organic light-emitting device. The compound represented by Formula 1 includes an indenoindene structure with four condensed rings. This highly condensed ring structure may increase molecular rigidity and molecular heat resistance. Furthermore, a glass transition temperature (Tg) and melting point of the molecules may be varied by introducing a variety of substituents for two $sp^3$ carbons in the indenoindene molecules. Furthermore, in the condensed cyclic compound of Formula 1, the structure of a combined indenoindene and styrylamine may facilitate an uneven distribution of electrons caused by the resonance of styrylamine and indenoindene and energy transition from a host. This may increase the emission efficiency of the styrylamine structure. Therefore, when the compound of Formula 1 is used as a dopant material for an organic light-emitting device, the organic light-emitting device may achieve high efficiency and high-purity blue light emission.

As used herein, non-limiting examples of the unsubstituted $C_1$-$C_{40}$ alkyl group (or $C_1$-$C_{40}$ alkyl group) include linear or branched $C_1$-$C_{40}$ alkyl groups, such as methyl, ethyl, propyl, isobutyl, sec-butyl, pentyl, iso-amyl, hexyl, and the like. The substituted $C_1$-$C_{40}$ alkyl group refers to a $C_1$-$C_{40}$ alkyl group in which at least one hydrogen atom is substituted with at least one of a deuterium atom; —F; —Cl; —Br; —I; —CN; a hydroxyl group; a nitro group; an amino group; an amidino group; a silyl group; hydrazine; hydrazone; a carboxyl group or a salt thereof; a sulfonic acid group or a salt thereof; a phosphoric acid group or a salt thereof; a $C_1$-$C_{40}$ alkyl group; a $C_1$-$C_{40}$ alkoxy group; a $C_2$-$C_{40}$ alkenyl group; a $C_2$-$C_{40}$ alkynyl group; a $C_1$-$C_{40}$ alkyl group, a $C_1$-$C_{40}$ alkoxy group, a $C_2$-$C_{40}$ alkenyl group, or a $C_2$-$C_{40}$ alkynyl group substituted with a deuterium atom, —F, —Cl, —Br, —I, —CN, a hydroxyl group, a nitro group, an amino group, an amidino group, a silyl group, hydrazine, hydrazone, a carboxyl group or a salt thereof, a sulfonic acid group or a salt thereof, or a phosphoric acid group or a salt thereof; a $C_3$-$C_{40}$ cycloalkyl group; a $C_5$-$C_{40}$ aryl group; a $C_2$-$C_{40}$ heteroaryl group; a $C_5$-$C_{40}$ arakyl group; a $C_5$-$C_{40}$ aryloxy group; or a $C_3$-$C_{40}$ cycloalkyl group, a $C_5$-$C_{40}$ aryl group, a $C_2$-$C_{40}$ heteroaryl group, a $C_5$-$C_{40}$ aralkyl group, or a $C_5$-$C_{40}$ aryloxy group substituted with at least one of a deuterium atom, —F, —Cl, —Br, —I, —CN, a hydroxyl group, a nitro group, an amino group, an amidino group, a silyl group, hydrazine, hydrazone, a carboxyl group or a salt thereof, a sulfonic acid group or a salt thereof, a phosphoric acid group or a salt thereof, a $C_1$-$C_{40}$ alkyl group, a $C_1$-$C_{40}$ alkoxy group, a $C_2$-$C_{40}$ alkenyl group, a $C_2$-$C_{40}$ alkynyl group, a $C_5$-$C_{40}$ aryl group, or a $C_2$-$C_{40}$ heteroaryl group.

As used herein, the unsubstituted $C_1$-$C_{40}$ alkoxy group (or a $C_1$-$C_{40}$ alkoxy group) may be represented by the formula of —OA, where A is a unsubstituted $C_1$-$C_{40}$ alkyl group as described above. Non-limiting examples thereof include methoxy, ethoxy, and isopropyloxy. The substituted $C_1$-$C_{40}$ alkoxy group refers to a $C_1$-$C_{40}$ alkoxy group in which at least one hydrogen atom is substituted with the substituents described above in connection with the substituted $C_1$-$C_{40}$ alkyl group.

As used herein, the unsubstituted $C_2$-$C_{40}$ alkenyl group (or $C_2$-$C_{40}$ alkenyl group) is a hydrocarbon chain having at least one carbon-carbon double bond in the center or at a terminal end of the unsubstituted $C_2$-$C_{40}$ alkyl group. Non-limiting examples of the unsubstituted $C_2$-$C_{40}$ alkenyl group include ethenyl, propenyl, and butenyl groups. The substituted $C_2$-$C_{40}$ alkenyl group refers to a $C_2$-$C_{40}$ alkenyl group in which at least one hydrogen atom is substituted with the substituents described above in connection with the substituted $C_2$-$C_{40}$ alkyl group.

As used herein, the unsubstituted $C_2$-$C_{40}$ alkynyl group (or $C_2$-$C_{40}$ alkynyl group) is an alkyl group having at least one carbon-carbon triple bond in the center or at a terminal end of the $C_2$-$C_{40}$ alkyl group. Non-limiting examples of the unsubstituted $C_2$-$C_{40}$ alkynyl group include ethynyl and propynyl. The substituted $C_2$-$C_{40}$ alkynyl group refers to a $C_2$-$C_{40}$ alkynyl group in which at least one hydrogen atom is substituted with the substituents described above in connection with the substituted $C_2$-$C_{40}$ alkyl group.

The unsubstituted $C_5$-$C_{40}$ aryl group is a monovalent group having a carbocyclic aromatic system having 5 to 40 carbon atoms including at least one aromatic ring. The unsubstituted $C_5$-$C_{40}$ arylene group is a divalent group having a carbocyclic aromatic system having 5 to 40 carbon atoms including at least one aromatic ring. When the aryl group or the arylene group has at least two rings, they may be fused to each other or connected to each other via a single bond. The substituted $C_5$-$C_{40}$ aryl group is a $C_5$-$C_{40}$ aryl group in which at least one hydrogen atom is substituted with the substituents described above in connection with the substituted $C_5$-$C_{40}$ alkyl group. The substituted $C_5$-$C_{40}$ arylene group is a $C_5$-$C_{40}$ arylene group in which at least one hydrogen atom is substituted with the substituents described above in connection with the substituted $C_5$-$C_{40}$ alkyl group.

Non-limiting examples of the substituted or unsubstituted $C_5$-$C_{40}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group or a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, or a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Non-limiting examples of the substituted $C_5$-$C_{40}$ aryl group may be inferred from the above examples of the unsubstituted $C_5$-$C_{40}$ aryl group and the substituted $C_1$-$C_{40}$ alkyl group. Non-limiting examples of the substituted or unsubstituted $C_5$-$C_{40}$ arylene group may be inferred from the examples of the substituted or unsubstituted $C_5$-$C_{40}$ aryl group described above.

The unsubstituted $C_2$-$C_{40}$ heteroaryl group is a monovalent group having at least one aromatic ring having at least one heteroatom selected from N, O, P, and S. The unsubstituted $C_2$-$C_{40}$ heteroarylene group is a divalent group having at least one aromatic ring having at least one heteroatom selected from N, O, P, and S. In this regard, when the heteroaryl group and the heteroarylene group have at least two rings, they may be fused to each or connected to each other via a single bond. The substituted $C_2$-$C_{40}$ heteroaryl group is a $C_2$-$C_{40}$ heteroaryl group in which at least one hydrogen atom is substituted with the substituents described above in connection with the substituted $C_1$-$C_{40}$ alkyl group. The substituted $C_2$-$C_{40}$ heteroarylene group is a $C_2$-$C_{40}$ heteroarylene group in which at least one hydrogen atom is substituted with the substituents described above in connection with the substituted $C_1$-$C_{40}$ alkyl group.

Non-limiting examples of the unsubstituted $C_2$-$C_{40}$ heteroaryl group include a pyrazolyl group, an imidazolyl group, an oxazolyl group, a thiazolyl group, a triazolyl group, a tetrazolyl group, an oxadiazolyl group, a pyridyl group, a pyridazinyl group, a pyrimidinyl group, a triazinyl group, a carbazolyl group, an indolyl group, a quinolinyl group, an isoquinolinyl group, a benzoimidazolyl group, an imidazopyridyl group and an imidazopyrimidinyl group. Examples of the $C_2$-$C_{40}$ heteroaryl group may be inferred from the examples of the unsubstituted $C_2$-$C_{40}$ heteroaryl group and the substituents of the substituted $C_1$-$C_{40}$ alkyl group described above. Examples of the substituted or unsubstituted $C_2$-$C_{40}$ heteroarylene group may be inferred based on the examples of the substituted or unsubstituted $C_2$-$C_{40}$ heteroaryl group described above.

The substituted or unsubstituted $C_5$-$C_{40}$ aryloxy group refers to an —$OA_2$ group in which $A_2$ is a substituted or unsubstituted $C_5$-$C_{40}$ aryl group (described above). The substituted or unsubstituted $C_5$-$C_{40}$ arylthiol group refers to a —$SA_3$ group in which $A_3$ is a substituted or unsubstituted $C_5$-$C_{40}$ aryl group (described above).

The condensed-cyclic compound of Formula 1 may be synthesized by organic synthesis. The synthesis method of the condensed-cyclic compound of Formula 1 may be understood by those of ordinary skill in the art from the examples that will be described below.

The condensed-cyclic compound of Formula 1 may be used between a pair of electrodes of an organic light-emitting device. For example, the condensed-cyclic compound may be used in an emission layer, in a layer between the anode and the emission layer (for example, a hole injection layer, a hole transport layer, or a functional layer with both hole injection and transport capabilities), and/or in a layer between the cathode and the emission layer (for example, an electron injection layer, an electron transport layer, or a functional layer with both hole injection and transport capabilities).

According to another aspect of the present invention, an organic light-emitting device includes a first electrode, a second electrode facing the first electrode, and an organic layer between the first electrode and the second electrode. The organic layer may include at least one layer. The organic layer may include at least one of the condensed-cyclic compounds of Formula 1 described above.

As used herein, the term "organic layer" refers to a layer containing an organic compound, and includes at least one layer. For example, the organic layer may include at least one layer selected from a hole injection layer, a hole transport layer, a functional layer (hereinafter, a hole injection transport layer) having both hole injection and hole transport capabilities, an electron blocking layer, an emission layer, a hole blocking layer, an electron injection layer, an electron transport layer, and a functional layer (hereinafter, an electron functional layer) having both electron injection and electron transport capabilities. The organic layer may not include solely an organic compound. The organic layer may include an inorganic compound or an inorganic material. In an embodiment, the organic layer may include both an organic compound and an inorganic compound or an inorganic material in one layer. For example, the organic layer may include an organometallic complex in one layer. In some other embodiments, the organic layer may include a layer containing an organic compound and a layer containing an inorganic compound or an inorganic material.

The organic layer may include at least one of the condensed-cyclic compounds listed above in one layer, and in some other embodiments, may include at least one of the condensed-cyclic compounds listed above in different layers. For example, the organic layer may include one of the condensed-cyclic compounds as an emitting dopant in an emission layer, and another condensed-cyclic compound as a hole transport material in a hole transport layer. In another embodiment, the organic layer may include one of the condensed-cyclic compounds as an emitting dopant and another condensed-cyclic compound as an emitting host in an emission layer. In another embodiment, the organic layer may include one of the condensed-cyclic compounds as an emitting dopant and another condensed-cyclic compound as an emitting host in an emission layer, and still another condensed-cyclic compound as a hole transport material in a hole transport layer.

The organic layer may include at least one of an emission layer, a hole injection layer, a hole transport layer, and a hole injection transport layer, and at least one of the emission layer, the hole injection layer, the hole transport layer, and the hole injection transport layer may include the condensed-cyclic compound.

In some embodiments, the organic light-emitting device may have a first electrode/hole injection layer/hole transport layer/emission layer/electron transport layer/second electrode structure, where the emission layer, the hole transport layer, or the hole injection layer may include the condensed-cyclic compound. In some embodiments, at least two of the emission layer, the hole transport layer, and the hole injection layer may include the condensed-cyclic compound. In these embodiments, each of the at least two layers may include a different condensed-cyclic compound. As described above, each layer of the organic layer may include a mixture of at least two of the condensed-cyclic compounds listed above, or a mixture of at least one of the condensed-cyclic compounds and another compound different from the above described condensed-cyclic compounds.

In some embodiments, the organic layer may include an emission layer, which may include a host and a dopant, and the condensed-cyclic compound may be a fluorescent host, a phosphorescent host, or a fluorescent dopant of the emission layer.

In some embodiments, the organic layer may include an emission layer, which may further include an anthracene compound, an arylamine compound, or a styryl compound. The emission layer may or may not include the condensed-cyclic compound.

The organic layer may include an emission layer, which may include a host and a dopant. The emission layer may further include a phosphorescent dopant. For example, the phosphorescent dopant may be, but is not limited to, an organometallic complex including at least one of iridium (Ir), platinum (Pt), osmium (Os), rhenium (Re), titanium (Ti), zirconium (Zr), hafnium (Hf), or a combination of at least two thereof. The emission layer may or may not include the condensed-cyclic compound.

At least one of the hole injection layer, the hole transport layer, and the hole injection transport layer may further include a charge-generating material, in addition to the condensed-cyclic compound. The charge-generating material may be, for example, a p-dopant. The hole injection layer, the hole transport layer, and the hole injection transport layer may or may not include the condensed-cyclic compound.

The organic layer may further include an electron transport layer, which may include an electron transporting organic compound and a metal-containing material. The metal-containing material may include a lithium (Li) complex. The electron transport layer may or may not include the condensed-cyclic compound.

FIG. 1 is a schematic sectional view of an organic light-emitting device 10 according to an embodiment of the present invention. Hereinafter, a structure of an organic light-emitting device according to an embodiment of the present invention and a method of manufacturing the same will be described with reference to FIG. 1.

Referring to FIG. 1, the organic light-emitting device 10 according to the present embodiment includes a first electrode 13, an organic layer 15, and a second electrode 17, which are sequentially stacked on a substrate 11.

The substrate 11 may be any substrate that is used in existing organic light-emitting devices. In some embodiments, the substrate 11 may be a glass substrate or a transparent plastic substrate with good mechanical strength, thermal stability, transparency, surface smoothness, ease of handling, and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transparent electrode. Suitable first electrode-forming materials include transparent and conductive materials such as ITO, IZO, $SnO_2$, and ZnO. In some embodiments, the first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed by vacuum deposition, the vacuum deposition conditions may vary according to the compound used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound used to form the HIL, and the desired structure and thermal properties of the HIL to be formed. For example, the coating rate may be in the range of about 2,000 rpm to about 5,000 rpm, and the temperature at which heat treatment is performed to remove solvent after coating may be in the range of about 80° C. to about 200° C. However, the coating conditions are not limited thereto.

For example, as the HIL material, the condensed-cyclic compound of Formula 1, or any known hole injection materials may be used. Non-limiting examples of hole injection materials include N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), 4.4'4"-Tris(N,N-diphenylamino)triphenylamine (TDATA), 4,4',4"-tris{N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline)/poly(4-styrenesulfonate (PANI/PSS).

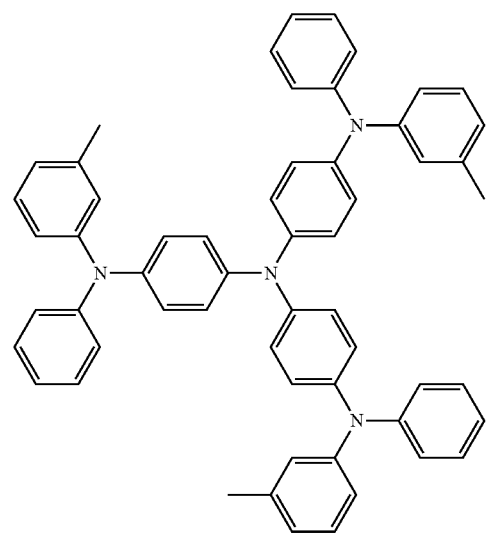

m-MTDATA

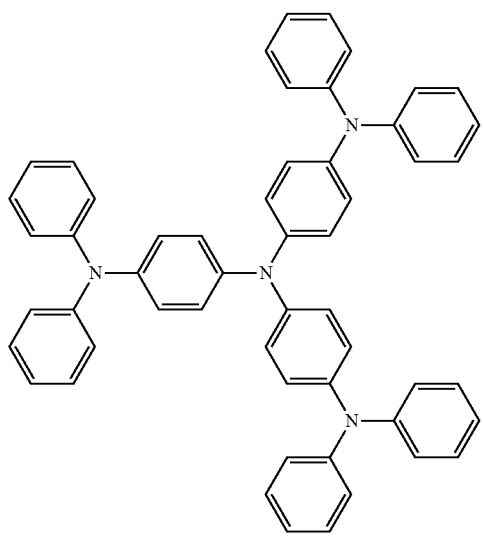

TDATA

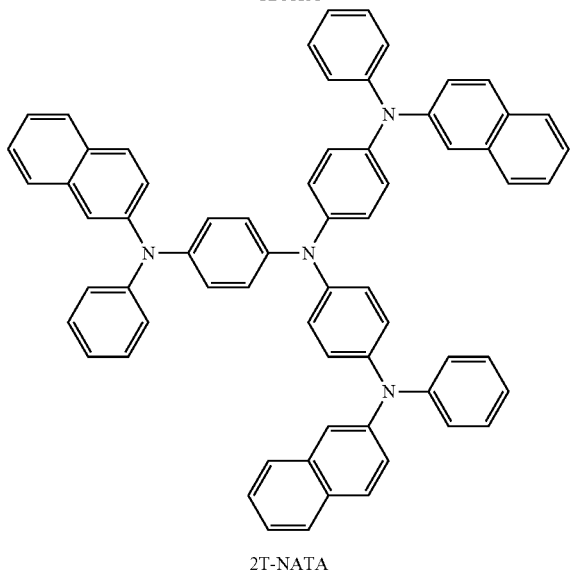

2T-NATA

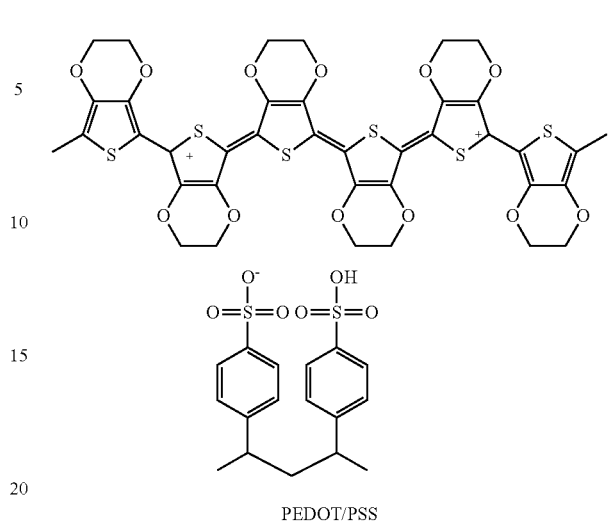

PEDOT/PSS

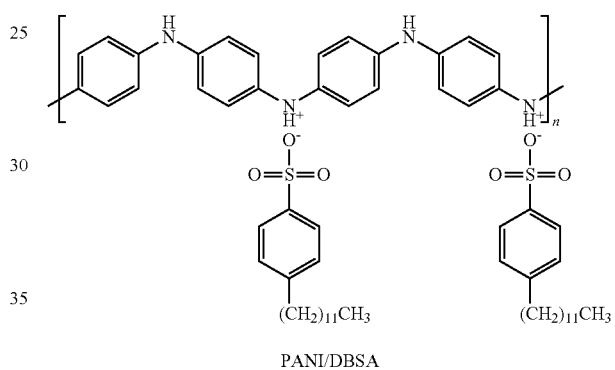

PANI/DBSA

The thickness of the HIL may be about 100 Å to about 10,000 Å, and for example, about 100 Å to about 1,000 Å. When the thickness of the HIL is within these ranges, the HIL may have good hole injecting ability without substantially increasing driving voltage.

Then, a HTL may be formed on the HIL by vacuum deposition, spin coating, casting, Langmuir-Blodgett (LB) deposition, or the like. When the HTL is formed by vacuum deposition or spin coating, the conditions for deposition or coating may be similar to those for the formation of the HIL, though the conditions for the deposition or coating may vary according to the material used to form the HTL.

The HTL may be formed of the condensed-cyclic compound of Formula 1 or any known hole transporting materials. Examples of hole transporting materials include carbazole derivatives such as N-phenylcarbazole, polyvinylcarbazole, and the like; triphenylamine materials such as TPD (N,N'-bis(3-methylphenyl)-N,N'-diphenyl-[1,1-biphenyl]-4,4'-diamine), NPB(N,N'-di(1-n aphthyl)-N,N'-diphenylbenzidine, TCTA (4,4',4''-tris(N-carbazolyl)triphenylamine), and the like.

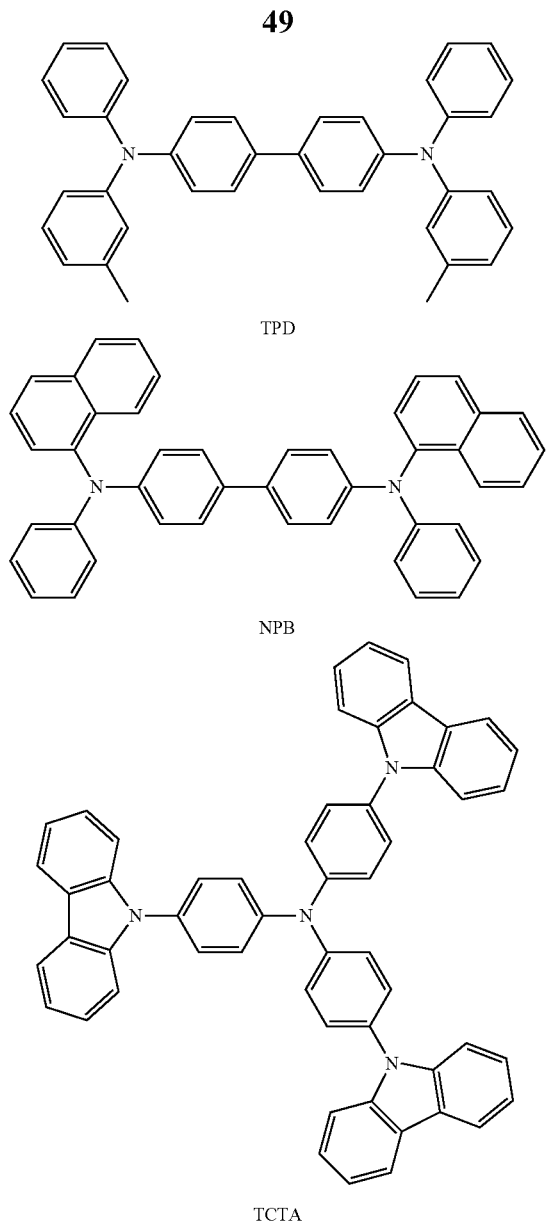

TPD

NPB

TCTA

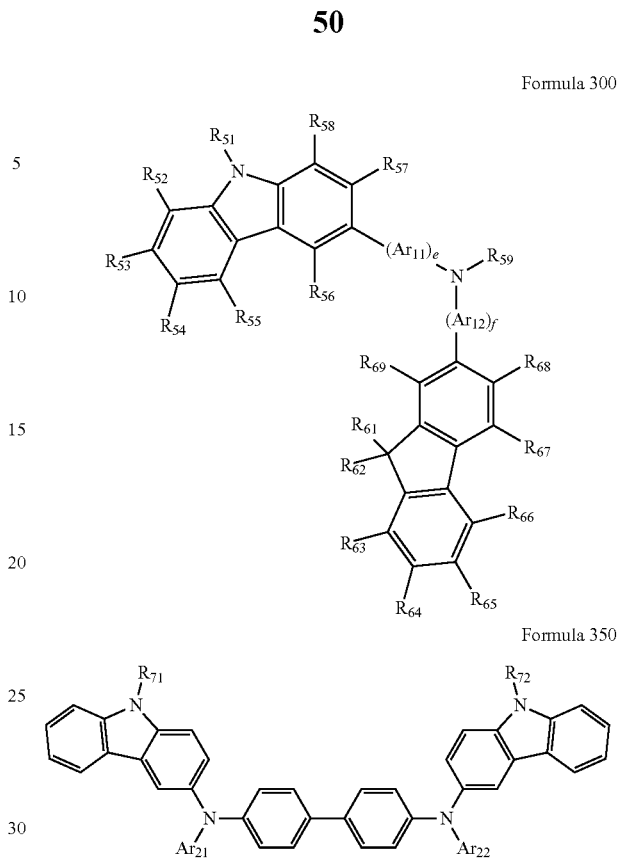

Formula 300

Formula 350

In Formulae 300 and 350, $Ar_{11}$ and $Ar_{12}$ are each independently a substituted or unsubstituted $C_5$-$C_{40}$ arylene group, and $Ar_{21}$ and $Ar_{22}$ may be each independently a substituted or unsubstituted $C_5$-$C_{40}$ aryl group. $Ar_{11}$, $Ar_{12}$, $Ar_{21}$ and $Ar_{22}$ are as defined above in connection with $Ar_1$ and $Ar_2$.

In Formula 300, e and f may be each independently an integer from 0 to 5, for example, may be 0, 1, or 2. In a non-limiting embodiment, e may be 1, and f may be 0.

In Formulae 300 and 350, $R_{51}$ to $R_{58}$, $R_{61}$ to $R_{69}$, and $R_{71}$ to $R_{72}$ may be each independently one of a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_5$-$C_{40}$ aryl group, a substituted or unsubstituted $C_5$-$C_{40}$ aryloxy group, or a substituted or unsubstituted $C_5$-$C_{40}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt The thickness of the HTL may be about 50 Å to about 1,000 Å, and for example, about 100 Å to about 800 Å. When the thickness of the HTL 14 is within these ranges, the HTL 140 may have satisfactory hole transporting ability without substantially increasing driving voltage.

In some embodiments, instead of the HIL and the HTL, a hole injection transport layer may be formed. The hole injection transport layer may contain at least one hole injection layer material and at least one hole transport layer material. The thickness of the hole injection transport layer may be from about 500 Å to about 10,000 Å, and in some embodiments, may be from about 100 Å to about 1,000 Å. When the thickness of the hole injection transport layer is within these ranges, the hole injection transport layer may have satisfactory hole injection and transport capabilities without substantially increasing driving voltage.

In some embodiments, at least one of the HIL, HTL, and hole injection transport layer may include at least one of a compound of Formula 300 below and a compound of Formula 350 below:

thereof, or a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

In Formula 300, $R_{59}$ may be independently a phenyl group, a naphthyl group, an anthryl group, a biphenyl group, or a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

In an embodiment, the compound of Formula 300 may be a compound represented by Formula 300A below, but is not limited thereto.

Formula 300A

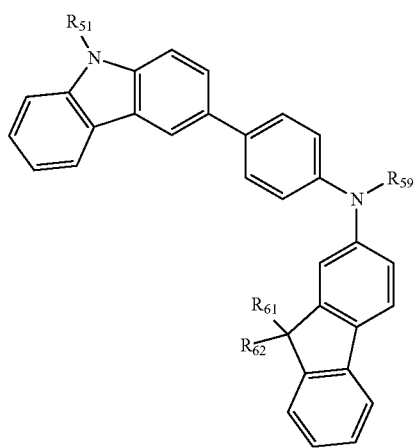

$R_{51}$, $R_{60}$, $R_{61}$ and $R_{59}$ in Formula 300A are as defined above.

In some embodiments, at least one of the HIL, HTL, and H-functional layer may include at least one compounds represented by one of Formulae 301 to 320 below.

301

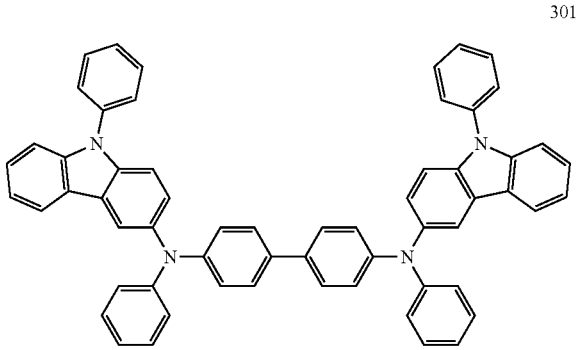

302

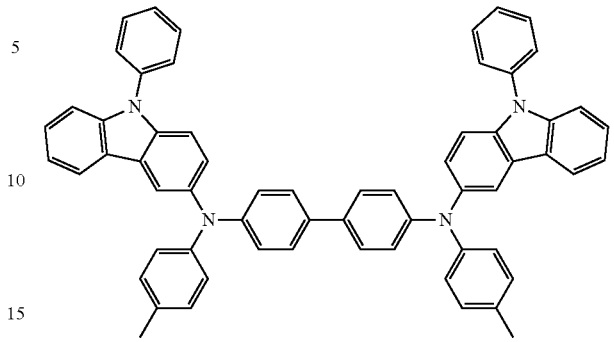

303

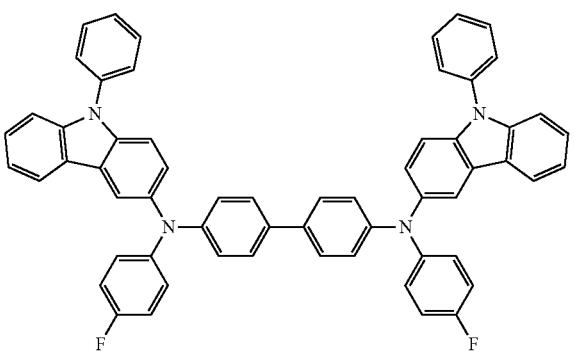

304

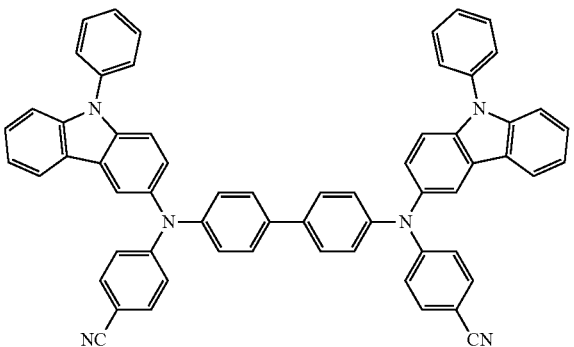

305

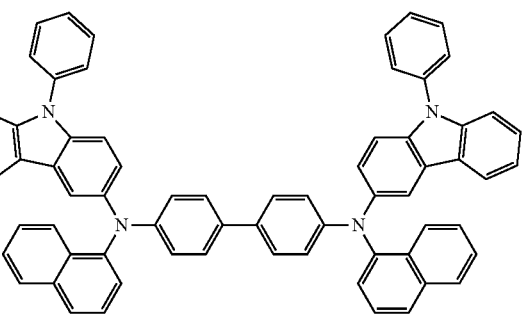

306
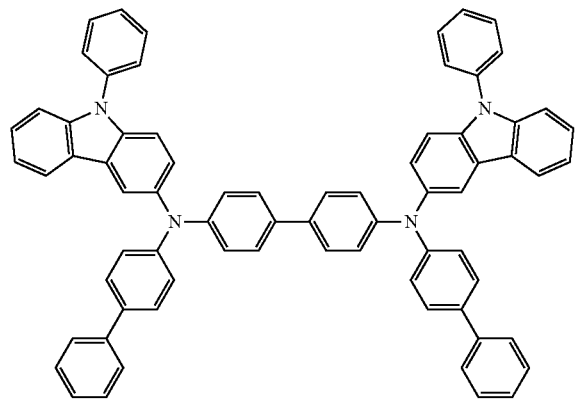
307
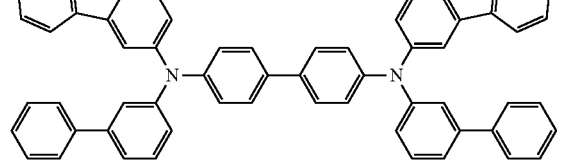
308
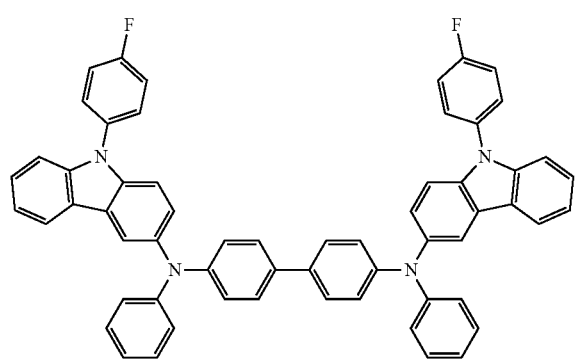
309
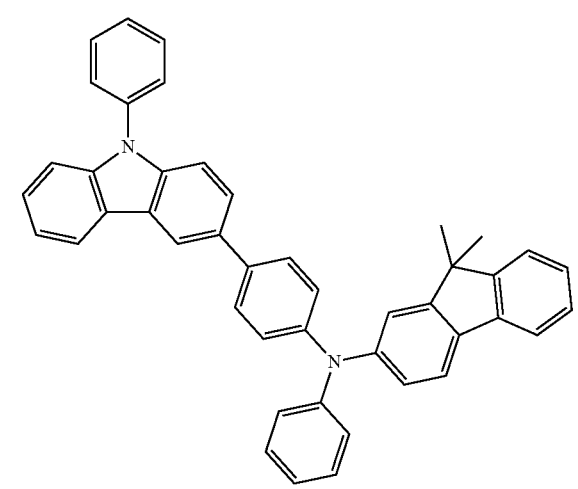
310
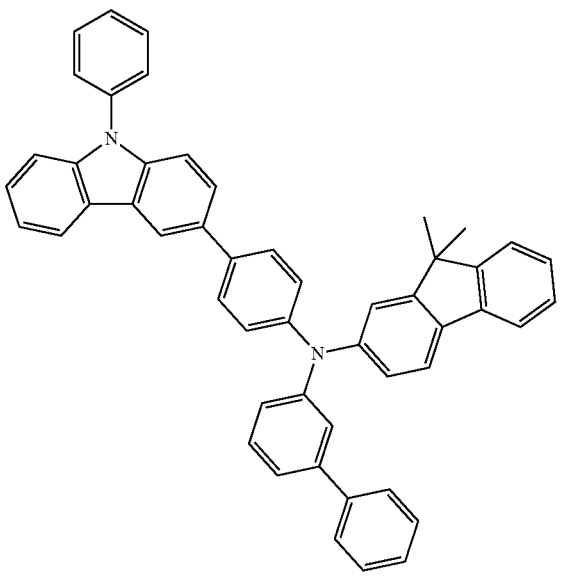
311
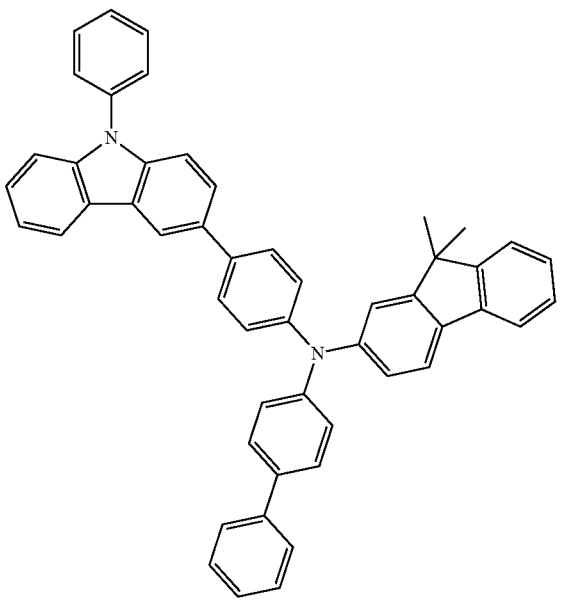

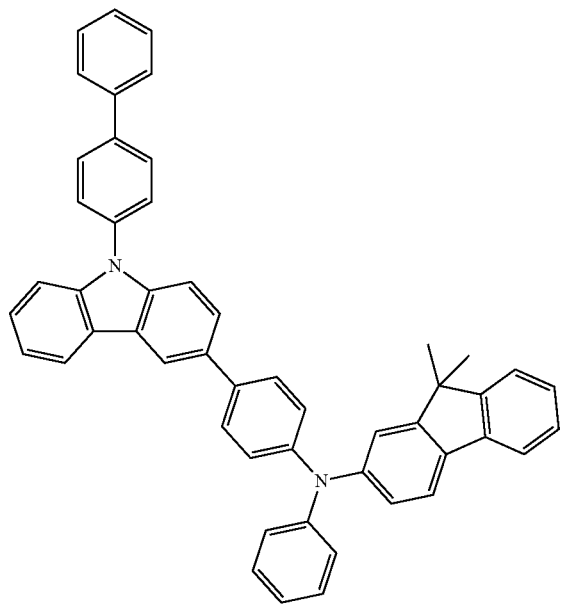
312
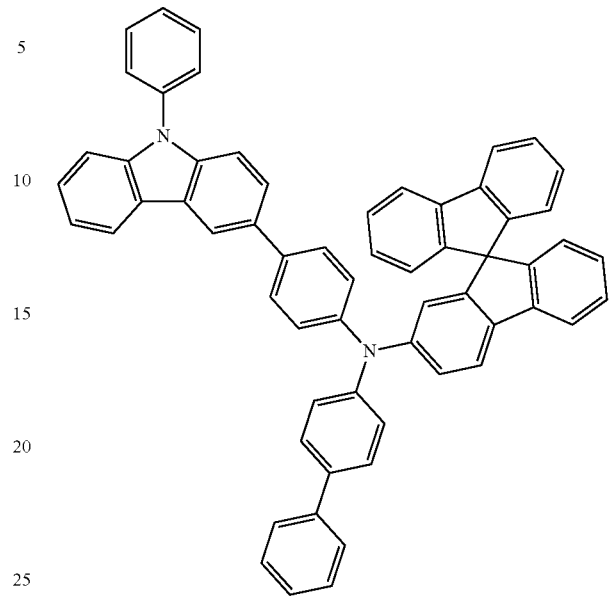
314
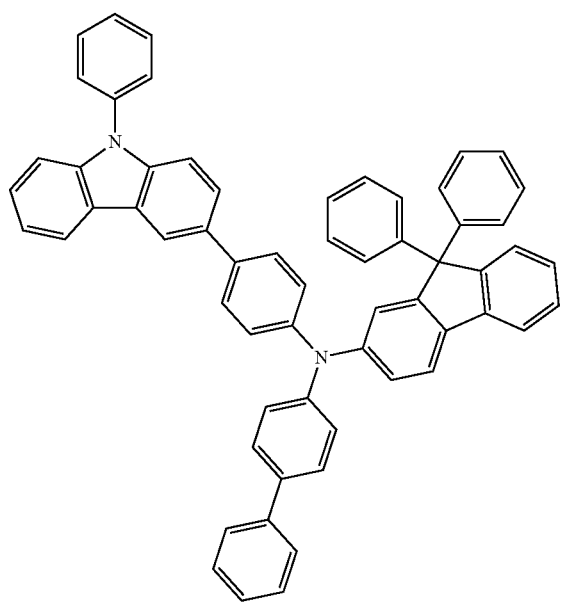
313
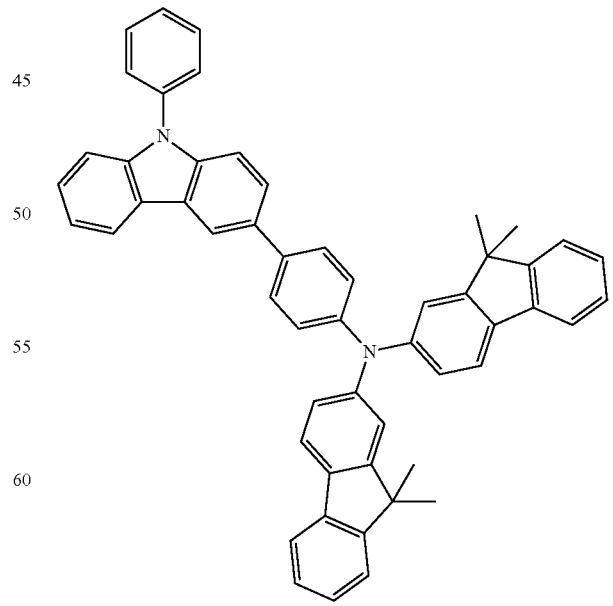
315

316

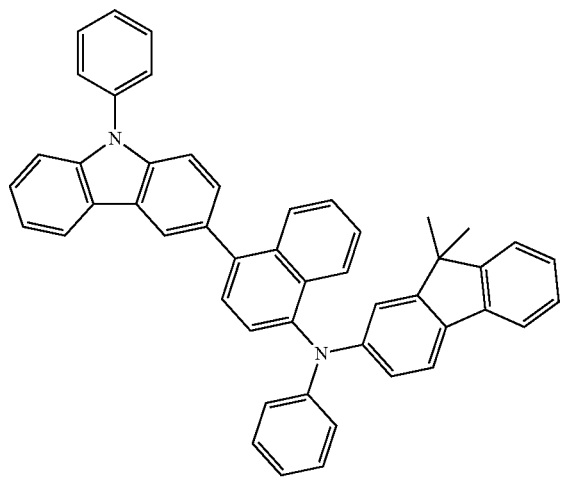

317

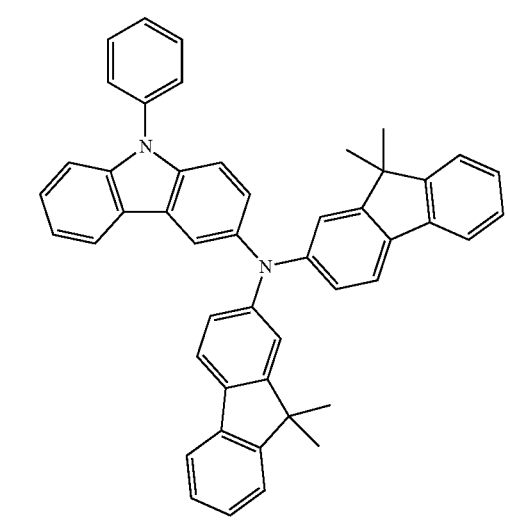

318

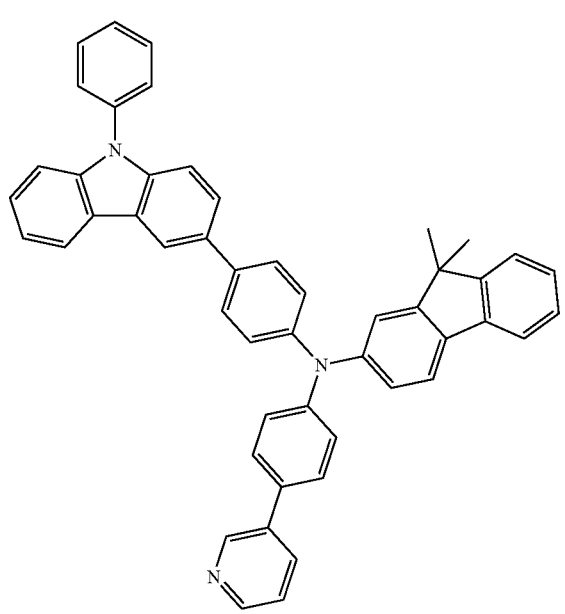

319

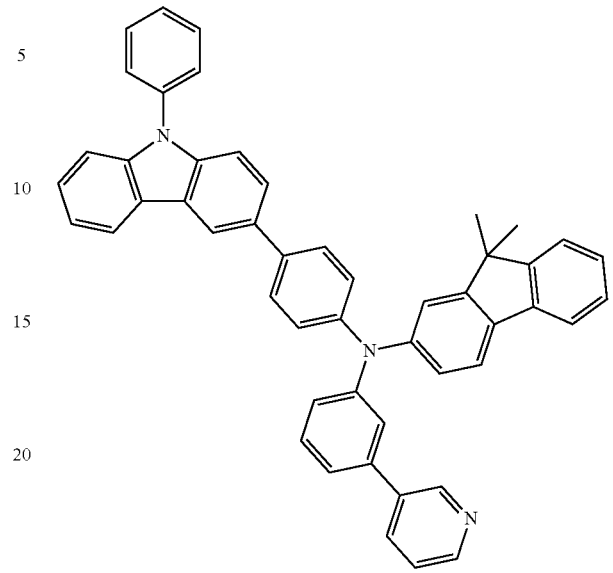

320

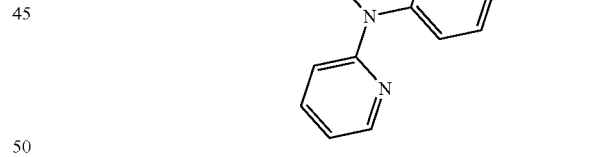

At least one of the HIL, HTL, and hole injection transport layer may further include a charge-generating material for improved layer conductivity, in addition to a known hole injecting material, hole transport material, and/or material having both hole injection and hole transport capabilities, as described above.

The charge generating material may be, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

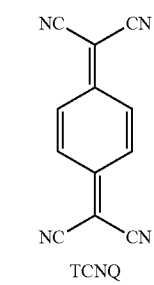

TCNQ

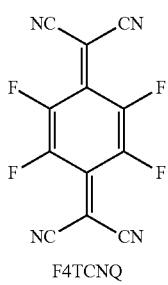

F4TCNQ

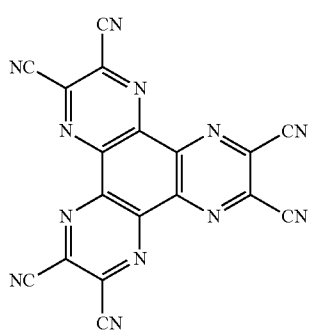

<100>

When the hole injection layer, the hole transport layer, or the hole injection transport layer having both hole injection and hole transport capabilities further includes a charge-generating material, the charge-generating material may be (but is not limited to being) homogeneously dispersed or inhomogeneously distributed in the layer.

A buffer layer may be disposed between at least one of the HIL, HTL, and hole injection transport layer, and the EML. The buffer layer may compensate for an optical resonance distance of light according to a wavelength of the light emitted from the EML, and thus may increase efficiency. The butter layer may include any hole injecting material or hole transporting material that is widely known. In some other embodiments, the buffer layer may include the same material as one of the materials included in the HIL, HTL, and hole injection transport layer that underlie the buffer layer.

Then, an EML may be formed on the HTL, hole injection transport layer, or buffer layer by vacuum deposition, spin coating, casting, Langmuir-Blodget (LB) deposition, or the like. When the EML is formed by vacuum deposition or spin coating, the deposition or coating conditions may be similar to those for the formation of the HIL, though the conditions for deposition or coating may vary according to the material used to form the EML.

The EML may be formed using at least one of the condensed-cyclic compounds of Formula 1, and known light-emitting materials (including hosts and dopants). When including the condensed-cyclic compound of Formula 1, the EML may further include a known phosphorescent host, fluorescent host, phosphorescent dopant, or fluorescent dopant. The condensed-cyclic compound may also serve as a phosphorescent host, a fluorescent host, or a fluorescent dopant.

The condensed-cyclic compound of Formula 1 may be used as a host. In another embodiment, a known dopant may be used. Non-limiting examples of hosts include Alq3 (tris(8-quinolinorate)aluminum), CBP (4.4'-N,N'-dicabazole-biphenyl), PVK (poly(n-vinylcarbazole), AND (9,10-di(naphthalene-2-yl)anthracene), TCTA, TPBI ((1,3,5-tris(N-phenylbenzimidazole-2-yl)benzene), TBADN ((3-tert-butyl-9,10-di(naphth-2-yl)anthracene), DSA (distyrylarylene), E3, dmCBP (see the following formula), and Compounds 501 to 509 below.

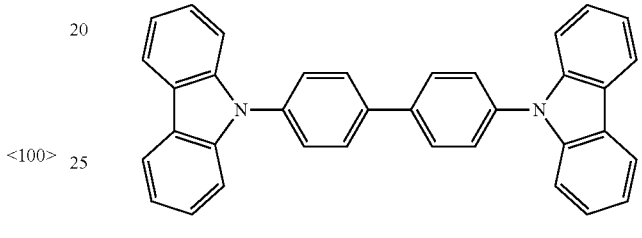

CBP

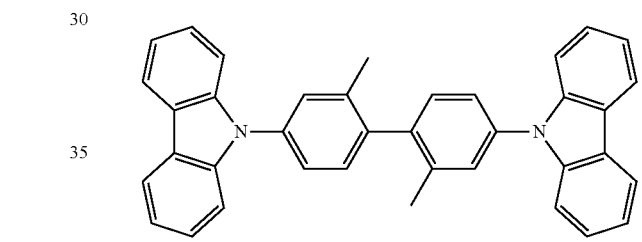

dmCBP

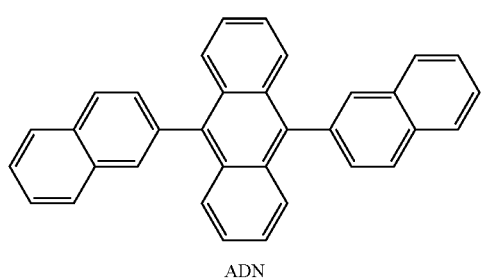

ADN

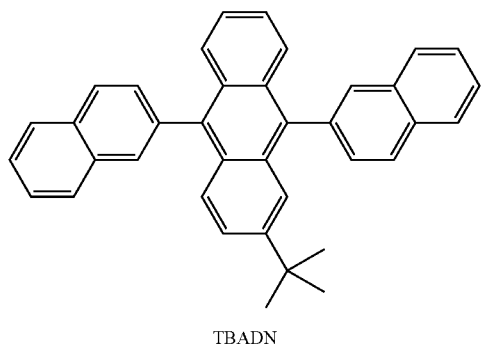

TBADN

-continued
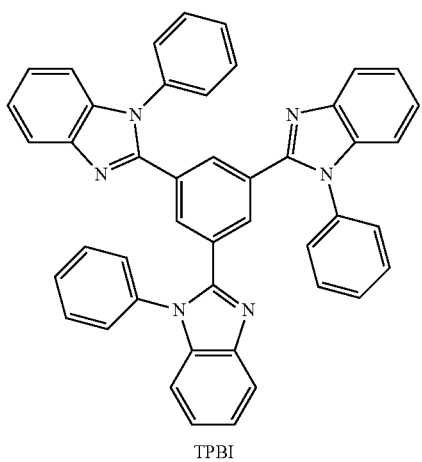
TPBI
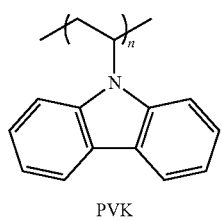
PVK
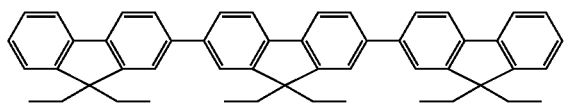
E3
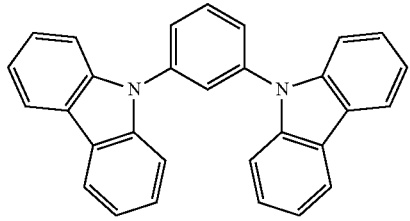
501
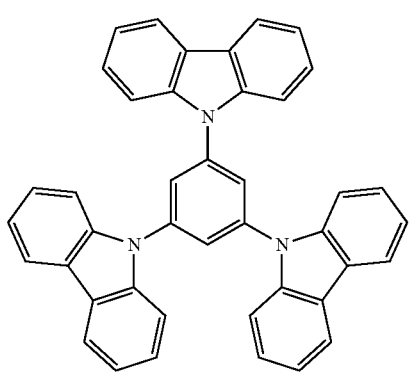
502
-continued
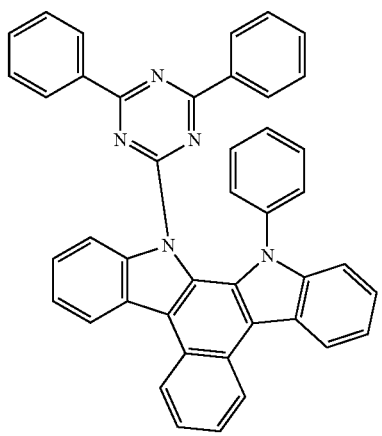
503
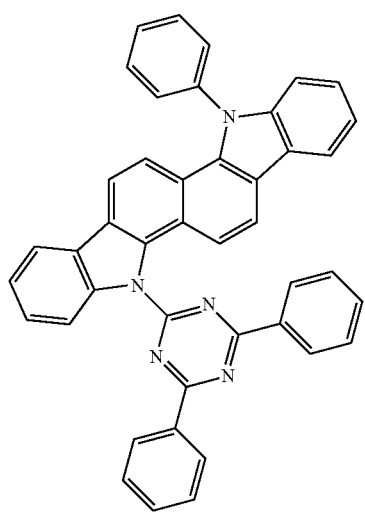
504
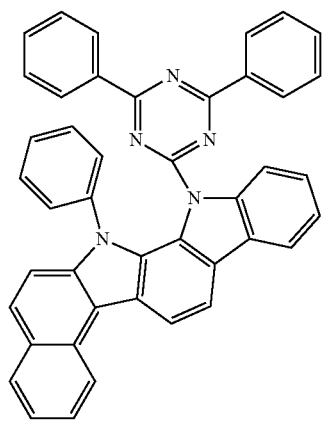
505

506

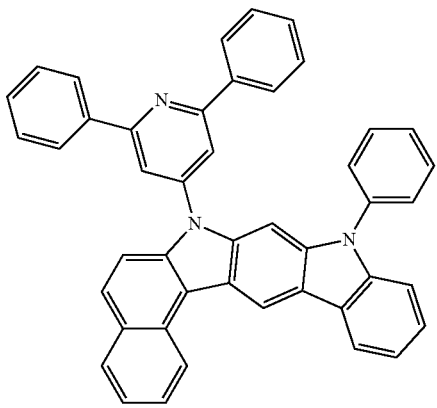

507

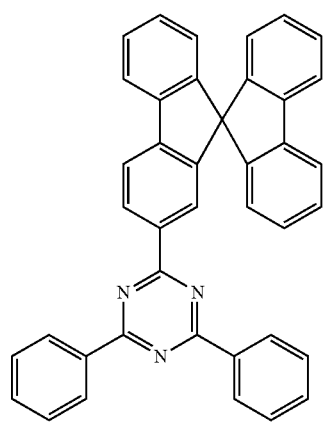

508

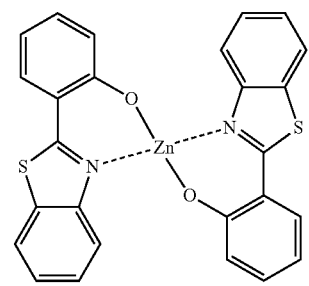

509

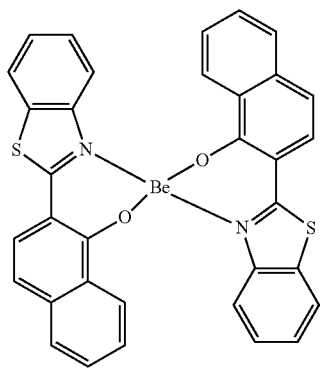

In some embodiments, an anthracene-based compound represented by Formula 400 below may be used as the host.

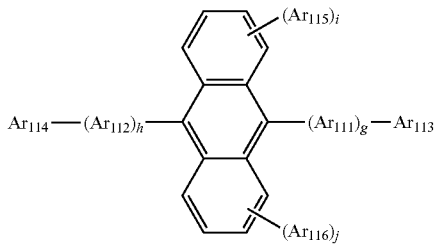

Formula 400

In Formula 400, $Ar_{111}$ and $Ar_{112}$ are each independently a substituted or unsubstituted $C_5$-$C_{40}$ arylene group. $Ar_{113}$ to $Ar_{116}$ are each independently a substituted or unsubstituted $C_1$-$C_{10}$ alkyl group or a substituted or unsubstituted $C_5$-$C_{40}$ aryl group. g, h, l, and j are each independently an integer from 0 to 4.

In some non-limiting embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group substituted with at least one of a phenyl group, a naphthyl group, or an anthryl group.

In Formula 400 above, g, h, l, and j may be each independently 0, 1, or 2.

In some non-limiting embodiments, $Ar_{113}$ to $Ar_{116}$ in Formula 400 may be each independently one of a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{40}$ alkyl group, a $C_2$-$C_{40}$ alkenyl group, a $C_2$-$C_{40}$ alkynyl group, a $C_1$-$C_{40}$ alkoxy group, a phenyl group, a naphthyl group, an anthryl group, a pyrenyl group, a phenanthrenyl group, or a fluorenyl group; or

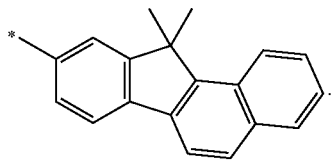 [SMILES: Cc1ccc2c(c1)C(C)(C)c1c-2ccc2ccccc12]

For example, the anthracene compound of Formula 400 above may be one of the compounds represented by the following formulae, but is not limited thereto.

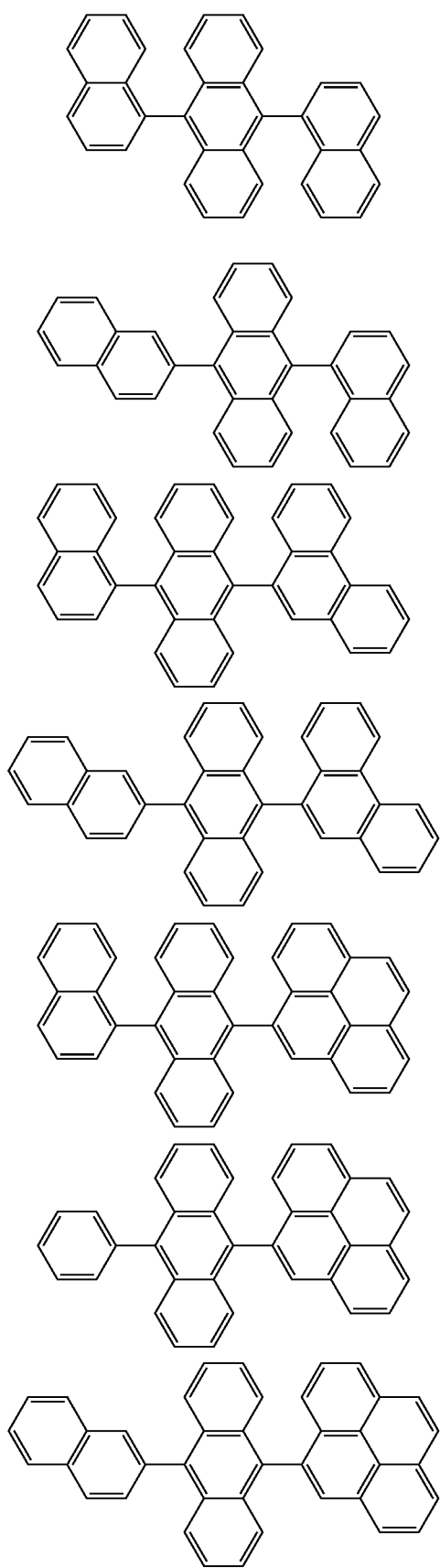
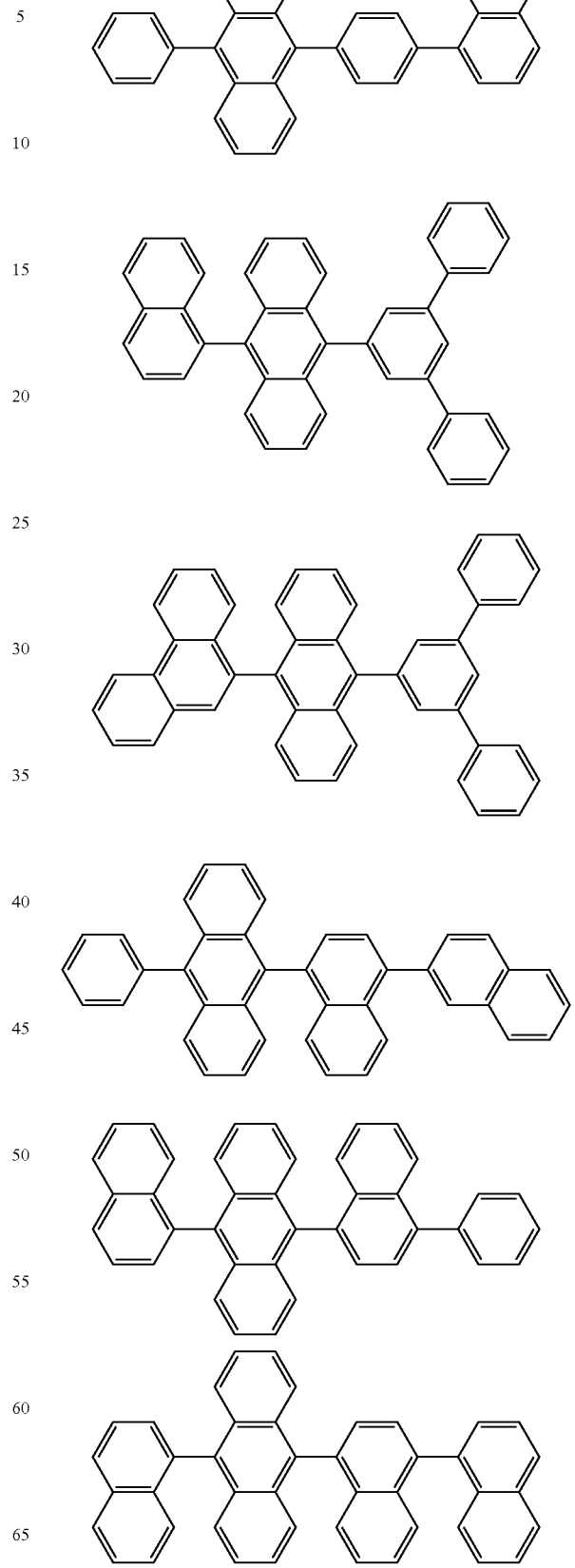

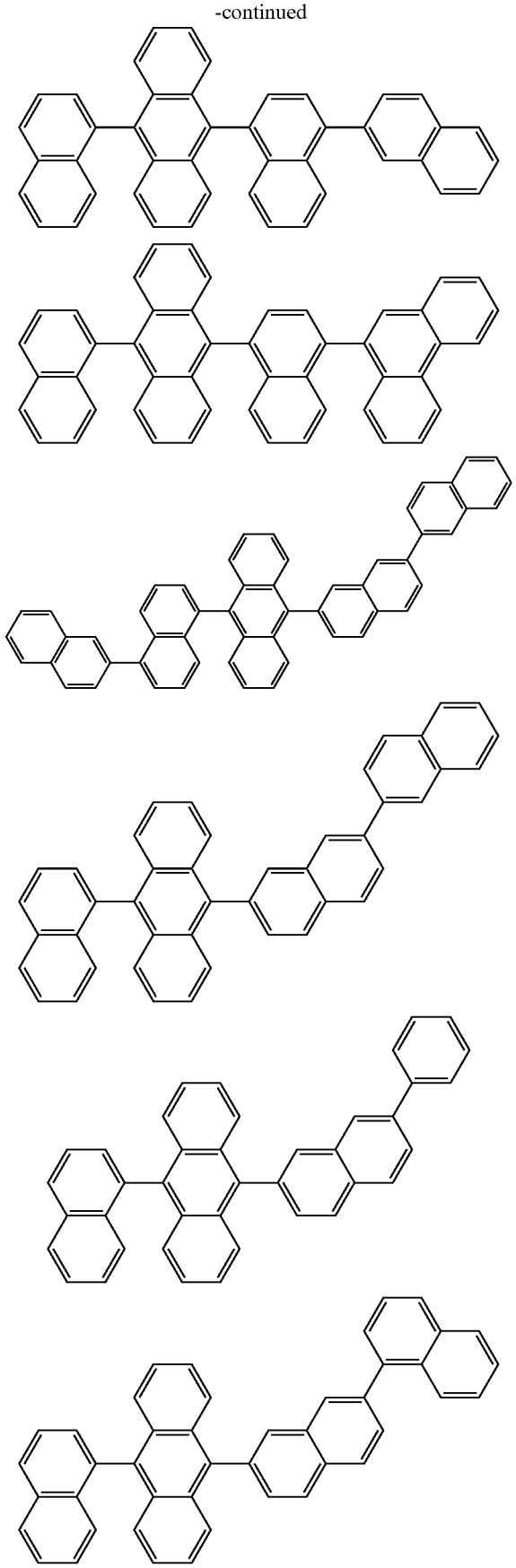

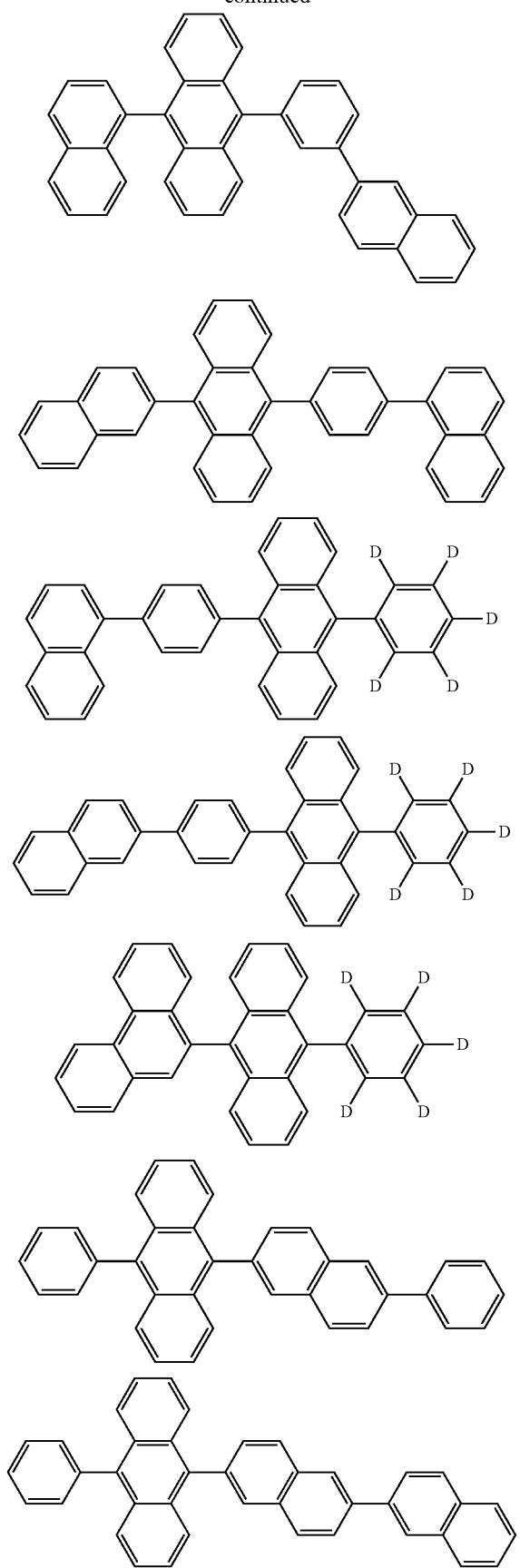

-continued

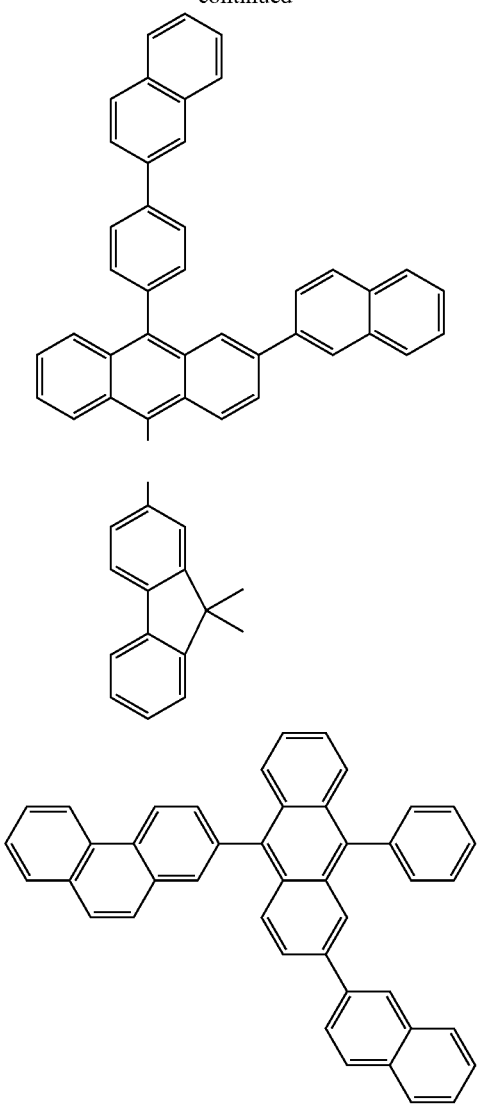

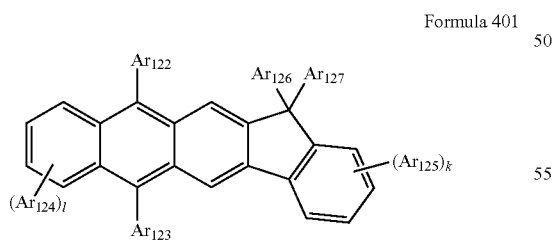

In some embodiments, an anthracene-based compound represented by Formula 401 below may be used as the host.

Formula 401

$Ar_{122}$ to $Ar_{125}$ in Formula 401 above may be defined as described above in conjunction with $Ar_{113}$ of Formula 400.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto.

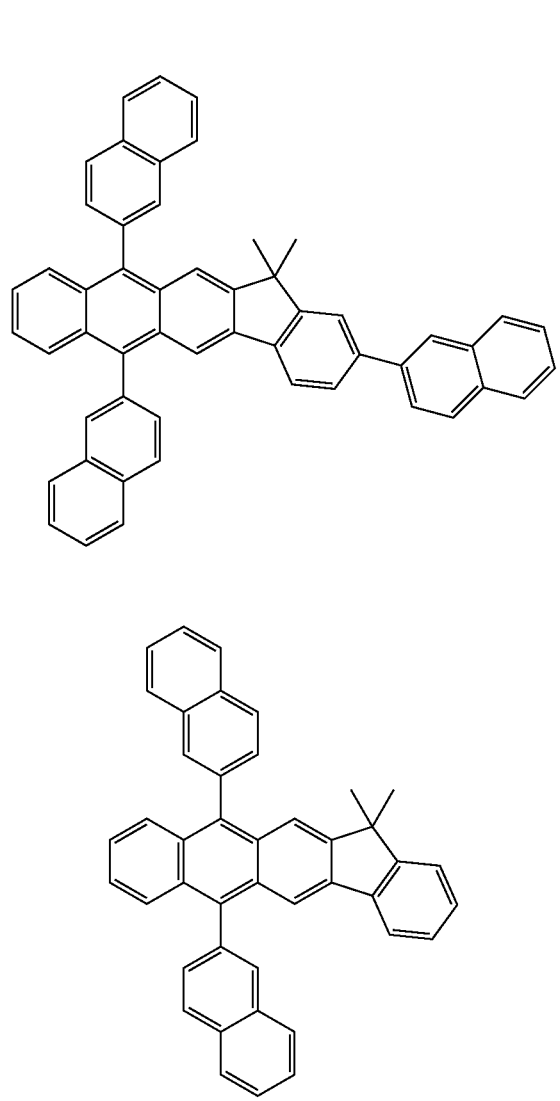

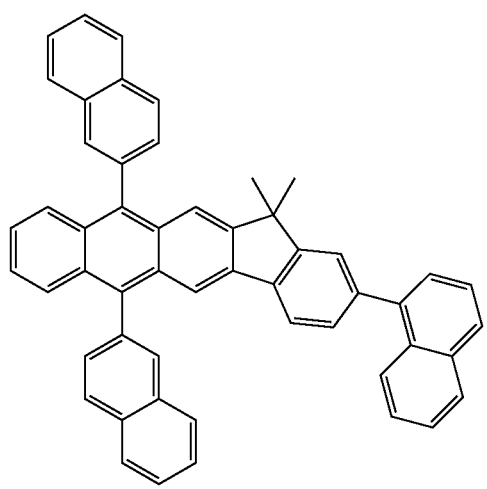

-continued

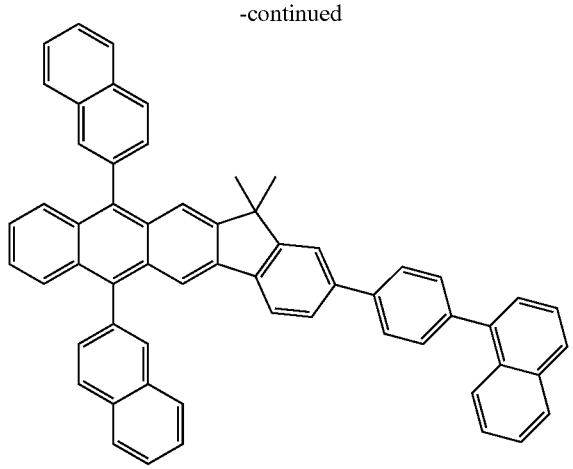

The condensed-cyclic compound of Formula 1 may be used as a dopant. In another embodiment, a known dopant may be used. For example, at least one of a fluorescent dopant and a phosphorescent dopant may be used. For example, the phosphorescent dopant may include, but is not limited to, an organometallic complex including at least one selected from iridium (Ir), platinum (Pt), osmium (Os), rhenium (Re), titanium (Ti), zirconium (Zr), hafnium (Hf), or a combination of at least two thereof.

Non-limiting examples of blue dopants include $F_2$Irpic (bis[3,5-difluoro-2-(2-pyridyl)phenyl](picolinato)iridium (III)), ($F_2$ ppy)$_2$Ir(tmd), Ir(dfppz)$_3$, DPVBi (4,4'-bis(2.2'-diphenylethen-1-yl)biphenyl), DPAVBi (4.4'-bis[4-(diphenylamino)styryl]biphenyl), and TBPe (2,5,8,11-tetra-tert-butyl perylene).

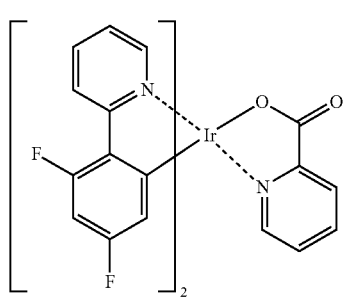

$F_2$Irpic

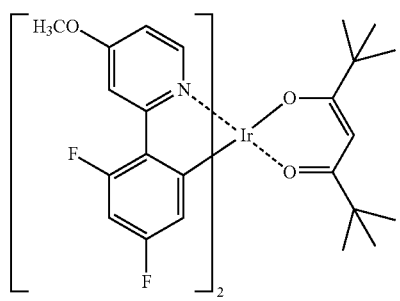

($F_2$ppy)$_2$Ir(tmd)

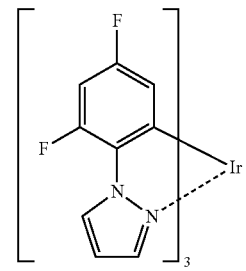

Ir(dfppz)$_3$

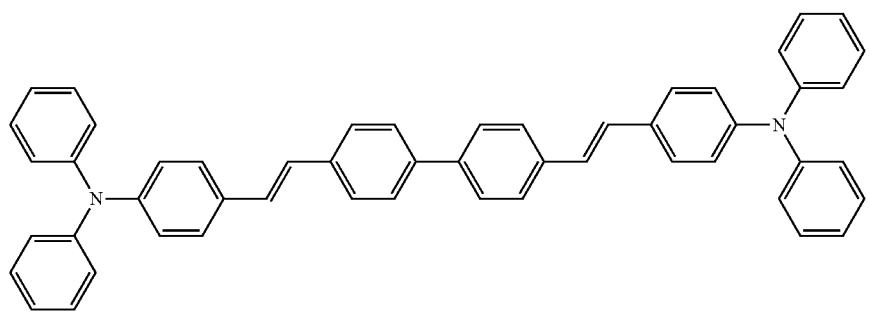

DPAVBi

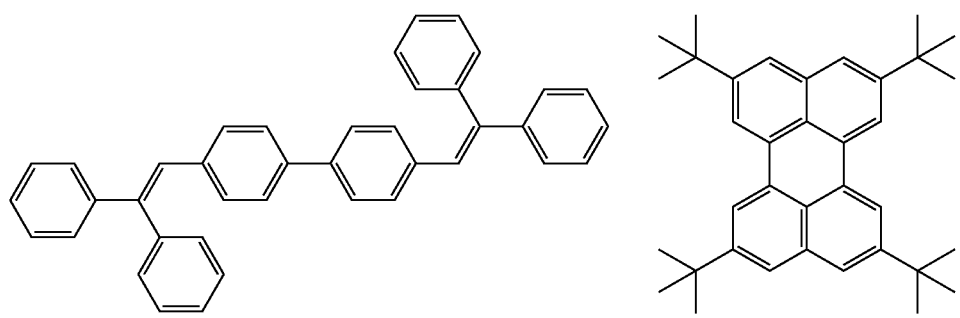

DPABi  TPBe

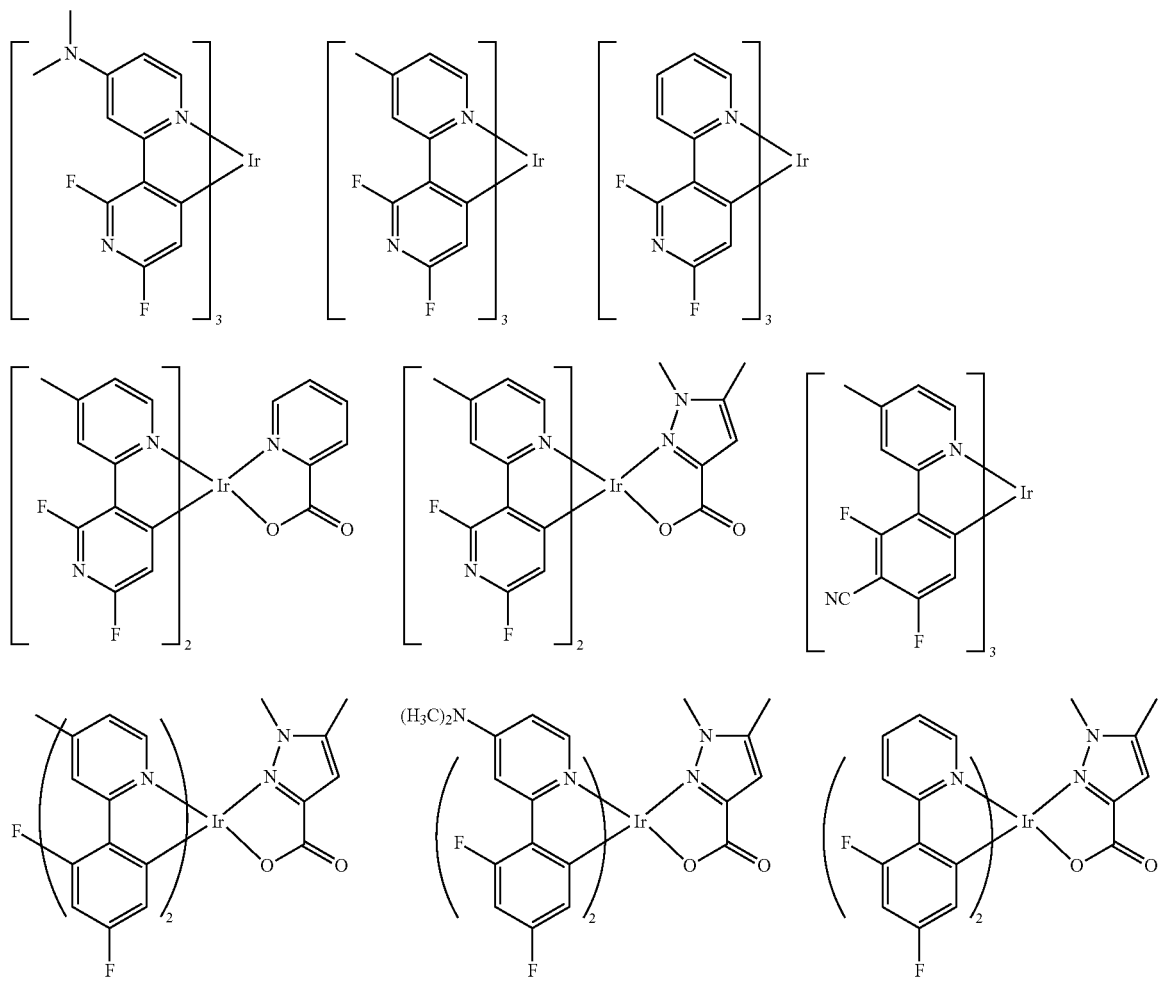
Non-limiting examples of red dopants include PtOEP (Pt (II) octaethylporphine), Ir(piq)₃ (tris(2-phenylisoquinoline) iridium), and Btp₂Ir(acac) (bis(2-(2'-benzothienyl)-pyridinato-N,C3')iridium(acetylacetonate)), which are represented by the following formulae.
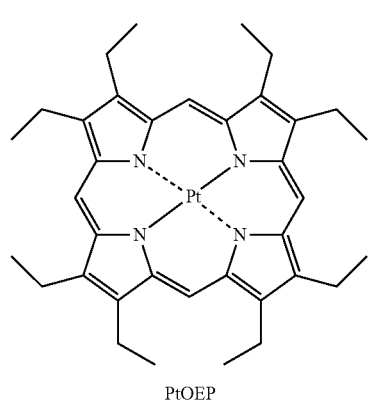
PtOEP
-continued
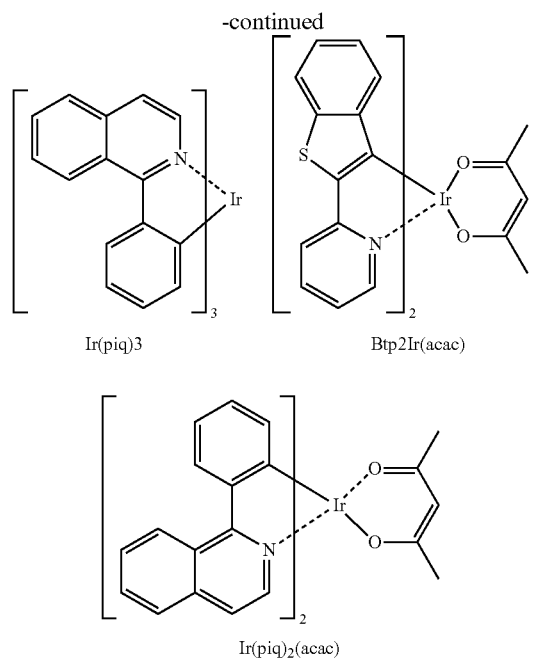
Ir(piq)3
Btp2Ir(acac)
Ir(piq)₂(acac)

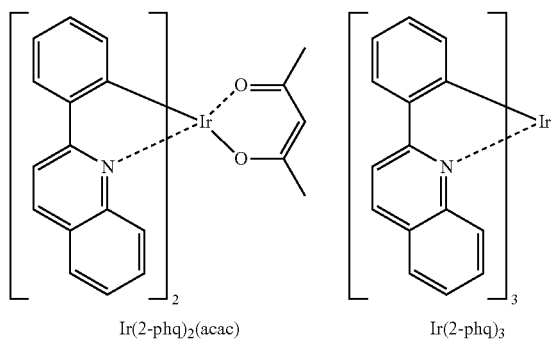

Ir(2-phq)₂(acac)   Ir(2-phq)₃

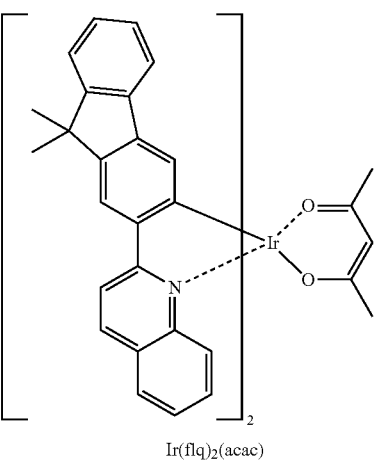

Ir(flq)₂(acac)

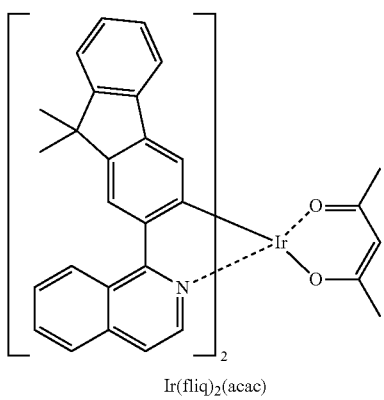

Ir(fliq)₂(acac)

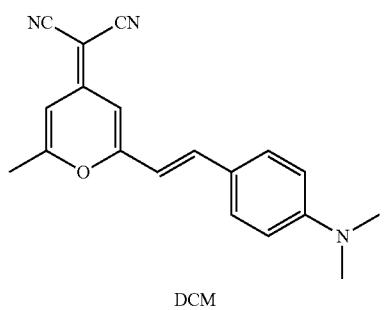

DCM

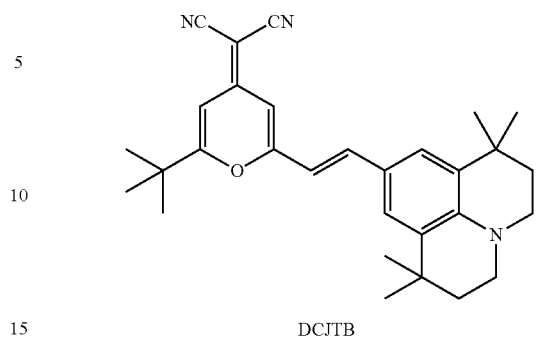

DCJTB

Non-limiting examples of red dopants are Ir(ppy)₃(tris(2-phenylpyridine) iridium), Ir(ppy)₂(acac)(bis(2-phenylpyridine)(acetylacetonato)iridium(III)), Ir(mppy)₃(tris(2-(4-tolyl)phenylpyridine)iridium), or C545T (10-(2-benzothiazolyl)-1,1,7,7-tetramethyl-2,3,6,7-tetrahydro-1H,5H,11H-[1]benzopyrano[6,7,8-ij]-quinolizin-11-one).

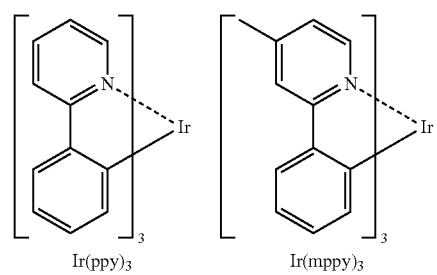

Ir(ppy)₃   Ir(mppy)₃

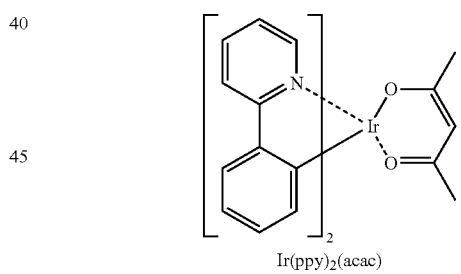

Ir(ppy)₂(acac)

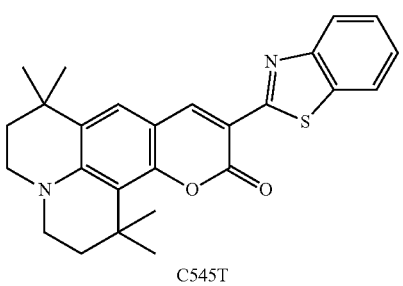

C545T

Non-limiting examples of the dopant that may be used in the EML include Pt complexes represented by the following formulae.

-continued
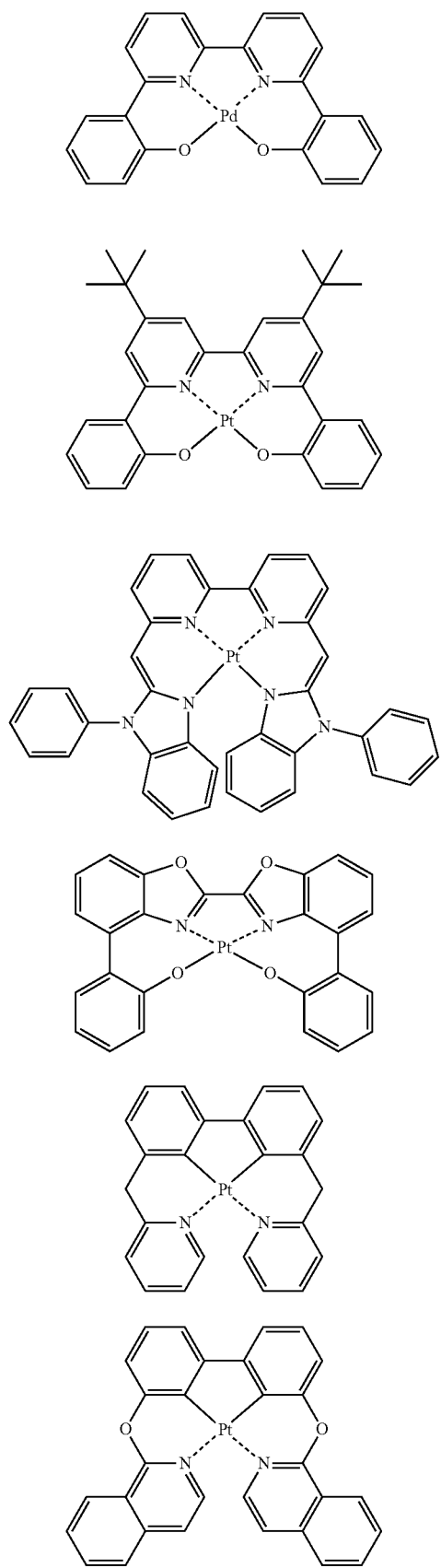
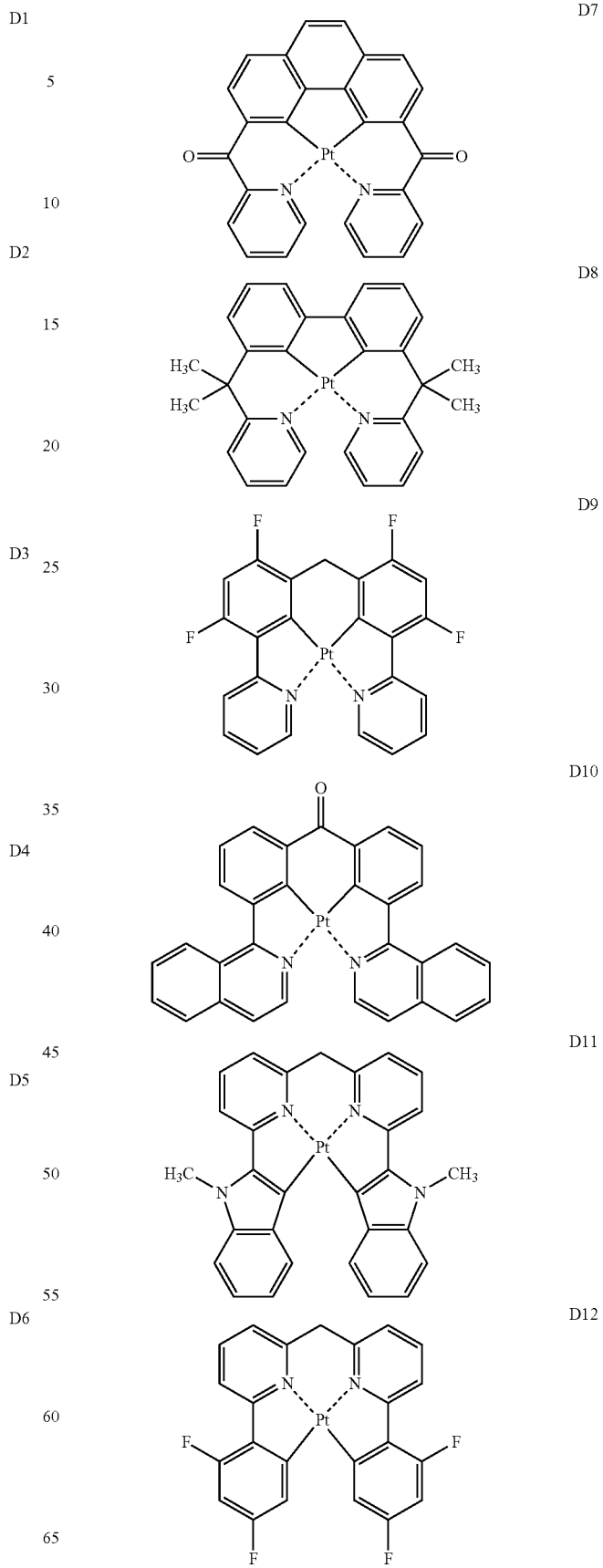

D13 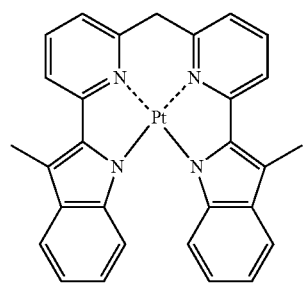
D14 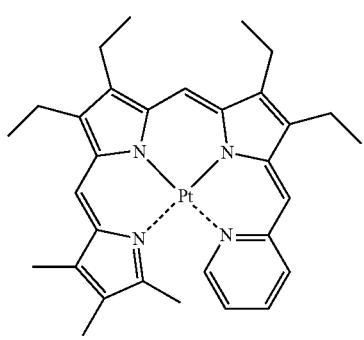
D15 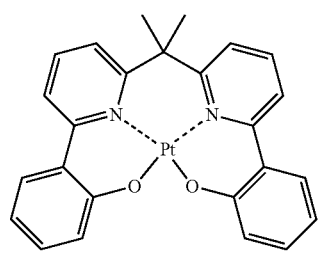
D16 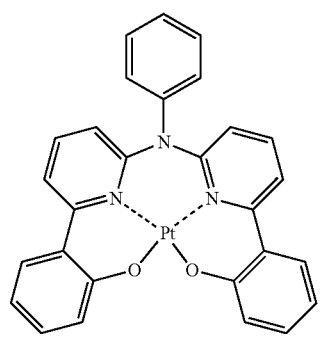
D17 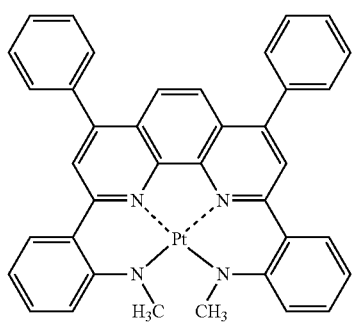
D18 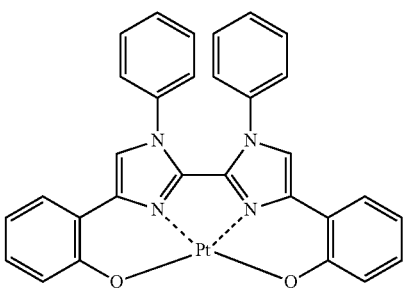
D19 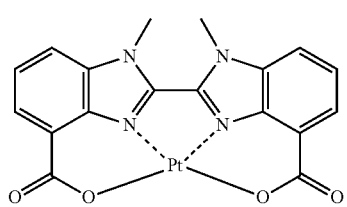
D20 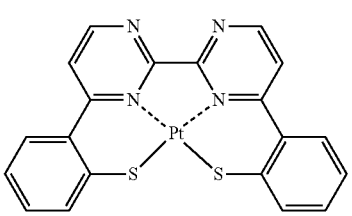
D21 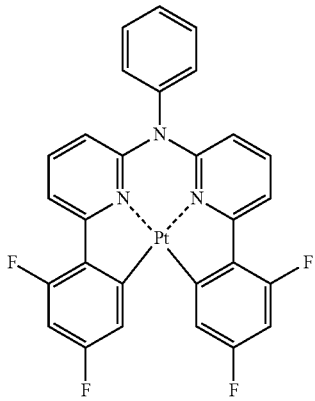
D22 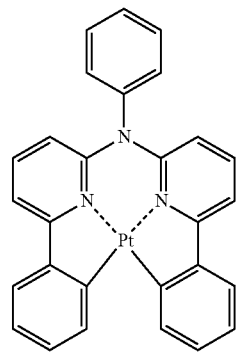

D23
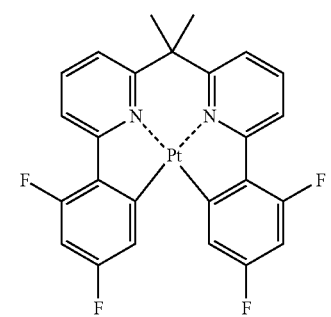
D24
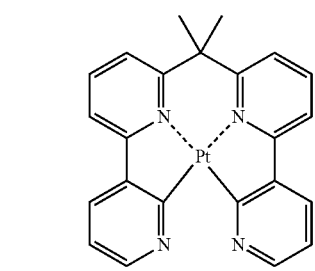
D25
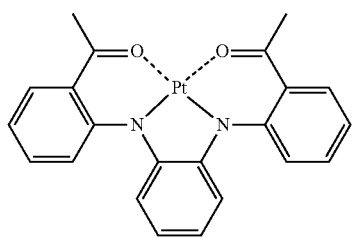
D26
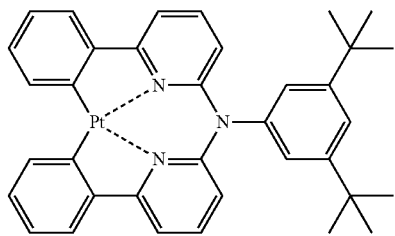
D27
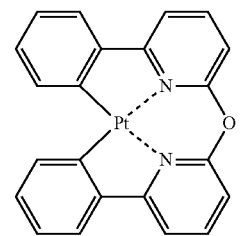
D28
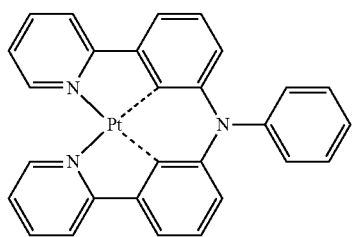
D29
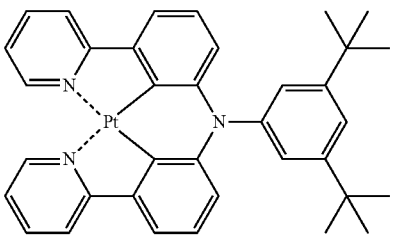
D30
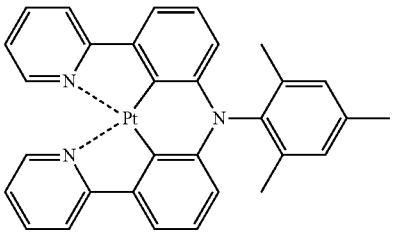
D31
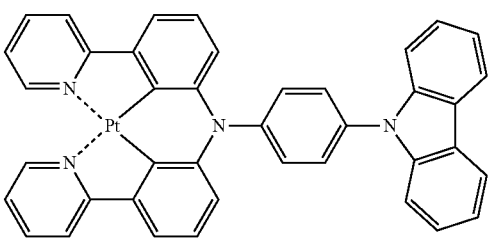
D32
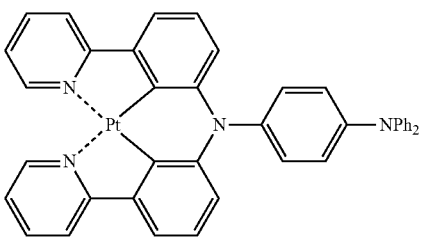
D33
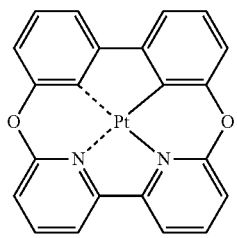
D34
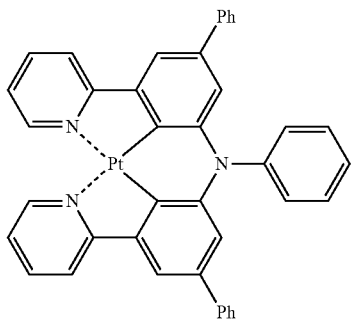

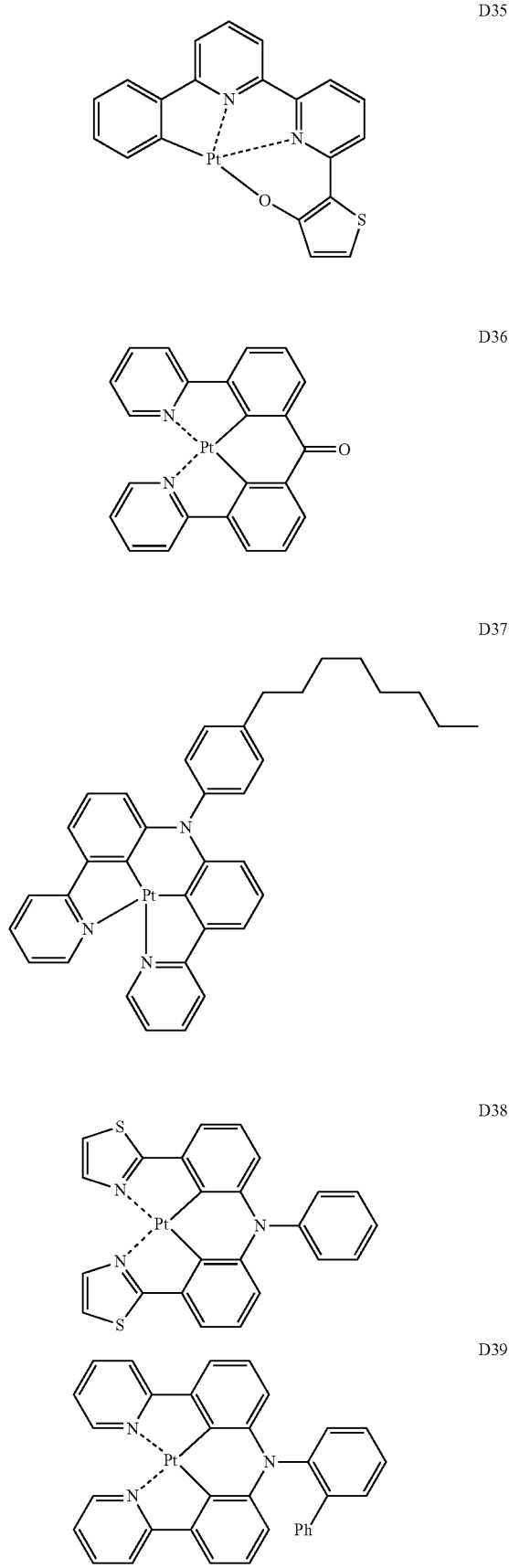

-continued
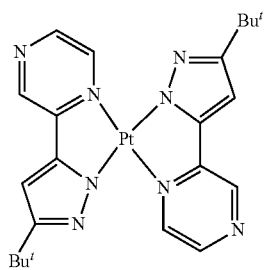
D45
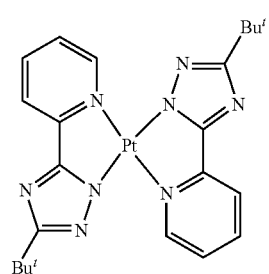
D46
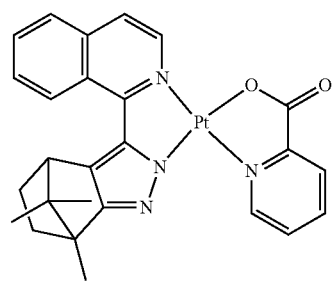
D47
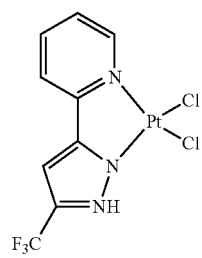
D48
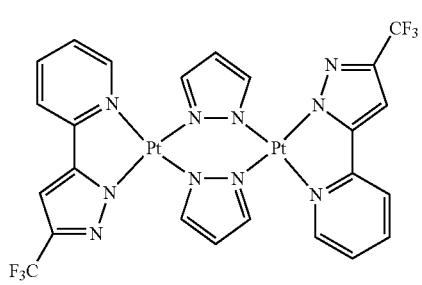
D49
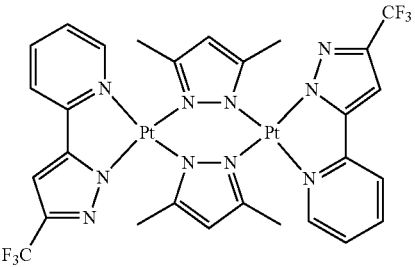
D50
Non-limiting examples of the dopant that may be used in the EML include Os complexes represented by the following formulae.
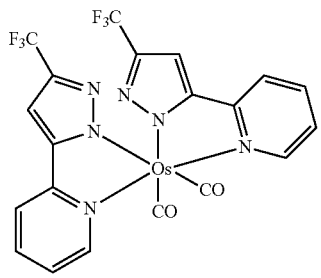
Os(fppz)$_2$(CO)$_2$
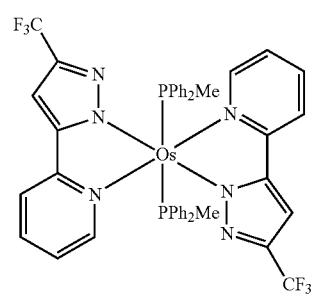
Os(fppz)$_2$(PPh$_2$Me)$_2$
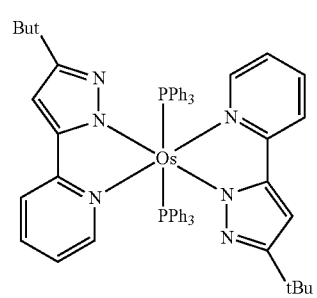
Os(bppz)$_2$(PPh$_3$)$_2$

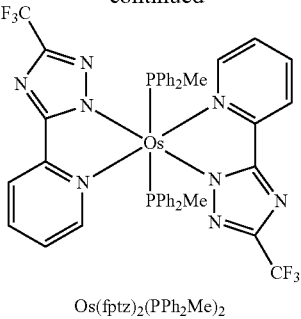

Os(fptz)₂(PPh₂Me)₂

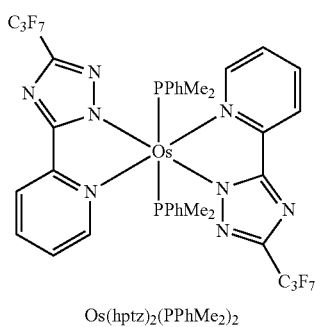

Os(hptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, may be from about 200 Å to about 600 Å. When the thickness of the EML is within these ranges, the EML may have good light emitting ability without substantially increasing driving voltage.

A HBL may be formed between the HTL and the EML by vacuum deposition, spin coating, casting, Langmuir-Blodgett (LB) deposition, or the like, in order to prevent diffusion of excitons or holes into the ETL. When the HBL is formed by vacuum deposition or spin coating, the conditions for deposition or coating may be similar to those for the formation of the HIL, although the conditions for deposition or coating may vary according to the material used to form the HBL. Any known hole-blocking material may be used. Non-limiting examples of hole-blocking materials include oxadiazole derivatives, triazole derivatives, and phenanthroline derivatives. For example, BCP may be used as a material for forming the HBL.

The thickness of the HBL may be from about 50 Å to about 1,000 Å, for example, about 100 Å to about 300 Å. When the thickness of the HBL is within these ranges, the HBL may have improved hole blocking ability without substantially increasing driving voltage.

Then, an ETL may be formed on the HBL or EML by vacuum deposition, spin coating, casting, or the like. When the ETL is formed by vacuum deposition or spin coating, the deposition or coating conditions may be similar to those for the formation of the HIL, though the deposition or coating conditions may vary according to the material that is used to form the ETL. The material for forming the ETL may be any known material that can stably transport electrons injected from an electron injecting electrode (cathode).

Non-limiting examples of ETL materials include quinoline derivatives, such as Alq3 (tris(8-quinolinolate)aluminum), BCP (2,9-dimethyl-4,7-diphenyl-1,10-phenanthroline), Bphen (4,7-diphenyl-1,10-phenanthroline; 4,7-diphenyl-1, 10-phenanthroline), TAZ (3-(4-biphenylyl)-4-phenyl-5-tert-butylphenyl-1,2,4-triazole), NTAZ (4-(Naphthalen-1-yl)-3, 5-diphenyl-4H-1,2,4-triazole), tBu-PBD(2-(4-biphenylyl)-5-(4-tert-butylphenyl)-1,3,4-oxadiazole, BAlq (see the following formula), Bebq₂ (beryllium bis(benzoquinolin-10-olate), ADN (9,10-di(naphthalene-2-yl)anthracene), Compound 101, and Compound 102.

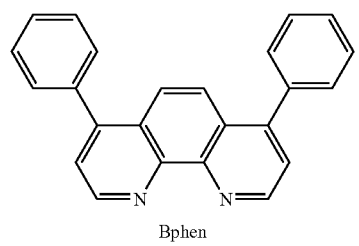

Bphen

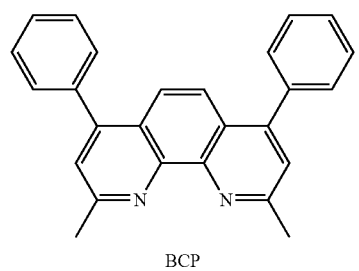

BCP

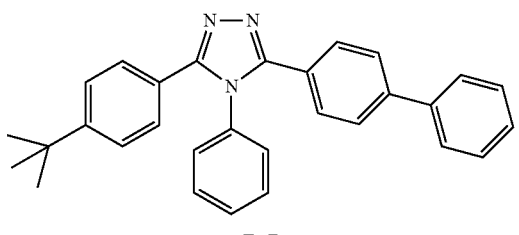

TAZ

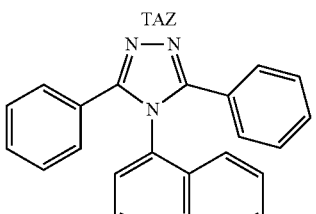

NTAZ

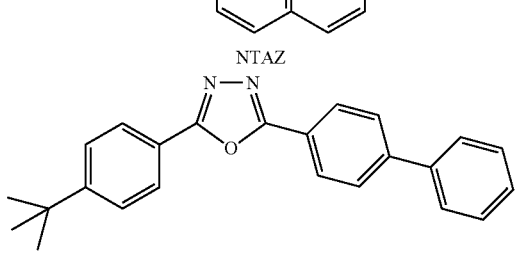

tBu-PBD

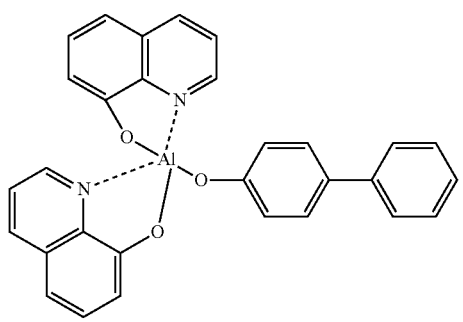

BAlq

<101>

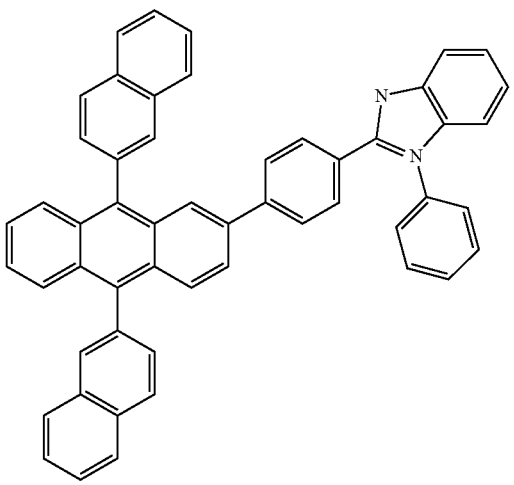

<102>

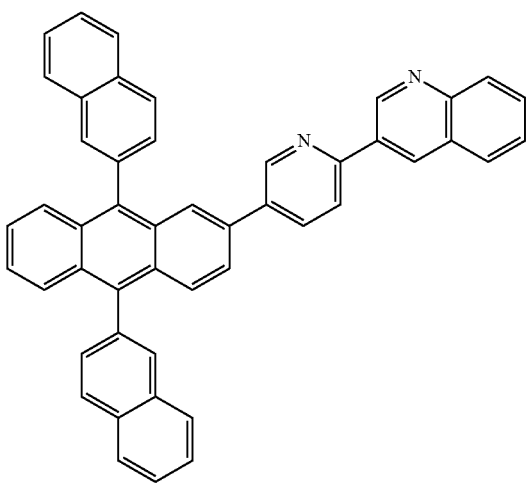

The thickness of the ETL may be from about 100 Å to about 1,000 Å, for example, about 150 Å to about 500 Å. When the thickness of the ETL is within these ranges, the ETL may have satisfactory electron transporting ability without substantially increasing in driving voltage.

In some embodiments, the ETL may include an electron-transporting organic compound and a metal-containing material. The metal-containing material may include a lithium (Li) complex. Non-limiting examples of the Li complex include lithium quinolate (LiQ) and Compound 103 below:

Compound 103

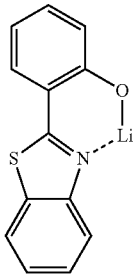

Then, an EIL, which facilitates injection of electrons from the cathode, may be formed on the ETL. Any suitable electron-injecting material may be used to form the EIL.

Examples of materials for forming the EIL include LiF, NaCl, CsF, $Li_2O$, and BaO. The deposition or coating conditions for forming the EIL 18 may be similar to those for the formation of the HIL, though the deposition or coating conditions may vary according to the material used to form the EIL 18.

The thickness of the EIL may be from about 1 Å to about 100 Å, for example, about 3 Å to about 90 Å. When the thickness of the EIL is within these ranges, the EIL may have satisfactory electron injection ability without substantially increasing driving voltage.

The second electrode 17 is disposed on the organic layer 15. The second electrode 17 may be a cathode that is an electron injection electrode. A material for forming the second electrode 17 may be a metal, an alloy, an electro-conductive compound (which have low work function), or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. To manufacture a top-emission type light-emitting device, the transmission electrode may be formed of indium tin oxide (ITO) or indium zinc oxide (IZO).

Hereinafter, the present invention will be described with reference to the following synthesis examples and other examples. However, these examples are presented for illustrative purposes only and are not intended to limit the scope of the present invention.

SYNTHESIS EXAMPLES

Synthesis Example 1

Synthesis of Compound 6

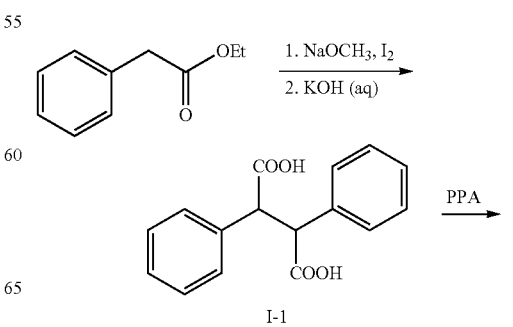

I-1

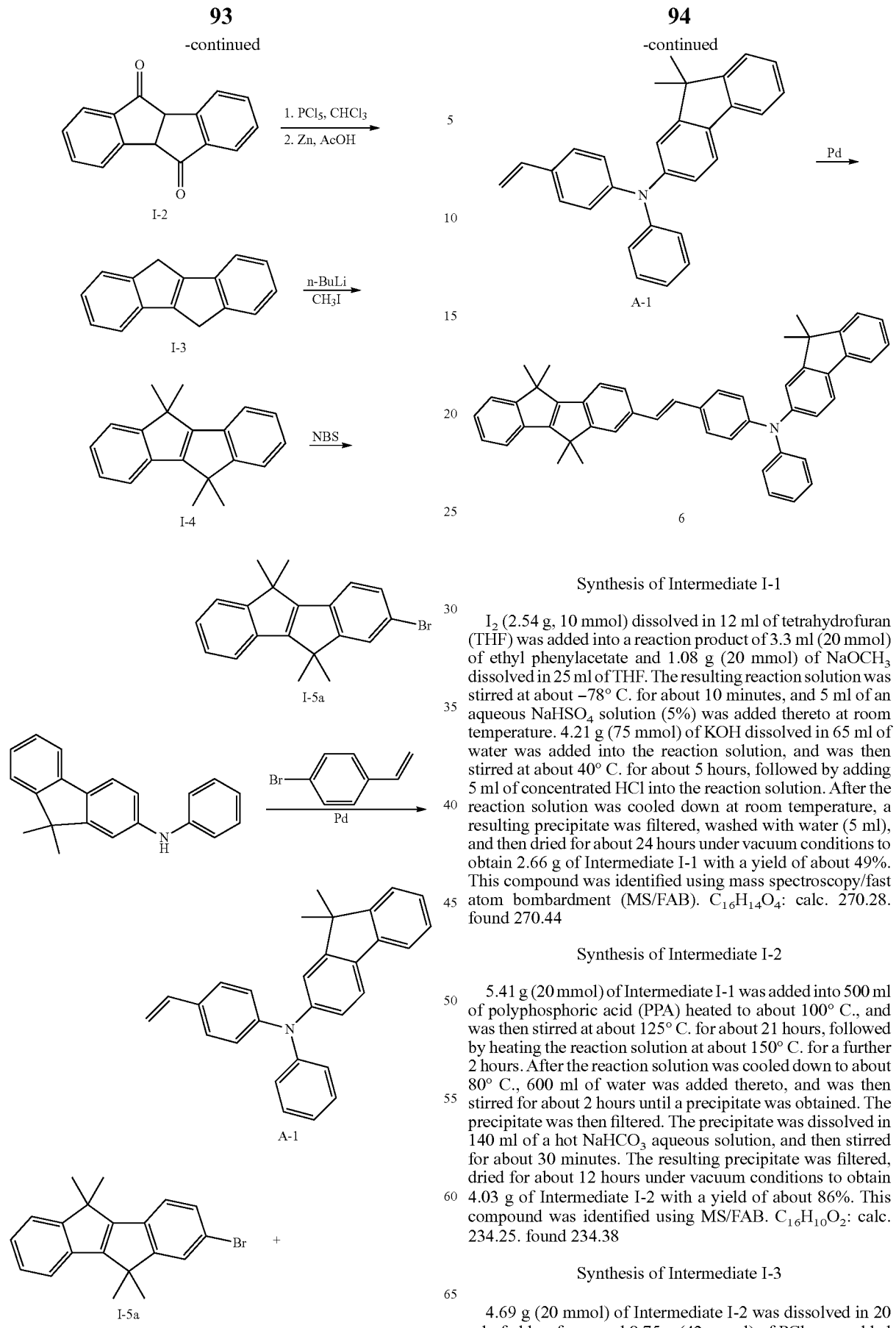

Synthesis of Intermediate I-1

I$_2$ (2.54 g, 10 mmol) dissolved in 12 ml of tetrahydrofuran (THF) was added into a reaction product of 3.3 ml (20 mmol) of ethyl phenylacetate and 1.08 g (20 mmol) of NaOCH$_3$ dissolved in 25 ml of THF. The resulting reaction solution was stirred at about −78° C. for about 10 minutes, and 5 ml of an aqueous NaHSO$_4$ solution (5%) was added thereto at room temperature. 4.21 g (75 mmol) of KOH dissolved in 65 ml of water was added into the reaction solution, and was then stirred at about 40° C. for about 5 hours, followed by adding 5 ml of concentrated HCl into the reaction solution. After the reaction solution was cooled down at room temperature, a resulting precipitate was filtered, washed with water (5 ml), and then dried for about 24 hours under vacuum conditions to obtain 2.66 g of Intermediate I-1 with a yield of about 49%. This compound was identified using mass spectroscopy/fast atom bombardment (MS/FAB). C$_{16}$H$_{14}$O$_4$: calc. 270.28. found 270.44

Synthesis of Intermediate I-2

5.41 g (20 mmol) of Intermediate I-1 was added into 500 ml of polyphosphoric acid (PPA) heated to about 100° C., and was then stirred at about 125° C. for about 21 hours, followed by heating the reaction solution at about 150° C. for a further 2 hours. After the reaction solution was cooled down to about 80° C., 600 ml of water was added thereto, and was then stirred for about 2 hours until a precipitate was obtained. The precipitate was then filtered. The precipitate was dissolved in 140 ml of a hot NaHCO$_3$ aqueous solution, and then stirred for about 30 minutes. The resulting precipitate was filtered, dried for about 12 hours under vacuum conditions to obtain 4.03 g of Intermediate I-2 with a yield of about 86%. This compound was identified using MS/FAB. C$_{16}$H$_{10}$O$_2$: calc. 234.25. found 234.38

Synthesis of Intermediate I-3

4.69 g (20 mmol) of Intermediate I-2 was dissolved in 20 ml of chloroform, and 8.75 g (42 mmol) of PCl$_5$ was added thereto and then refluxed at about 50° C. for about 30 minutes. The reaction solution was cooled down to room temperature, and the solvent was removed from the reaction solution in a vacuum condition. The resulting residue was diluted with acetic acid, and 25 g of zinc powder was slowly added thereto. The resulting precipitate was filtrated and washed with acetic acid. The residue was separated and purified using silica gel column chromatography to obtain 3.71 g of Intermediate I-3 with a yield of about 91%. This compound was identified using MS/FAB. $C_{16}H_{12}$: calc. 204.27. found 204.42

Synthesis of Intermediate I-4

2.04 g (10 mmol) of intermediate I-3 and 37.5 mL (60 mmol) of n-BuLi (1.60M hexane solution) was gradually reacted with THF at about −78° C. 3.8 ml (60 mmol) of $CH_3I$ was added into the reaction solution, and was then stirred at room temperature for about 3 hours, followed by adding 5 ml of a 1N HCl aqueous solution into the mixture. The organic phase was separated from the reaction solution, and the aqueous phase was extracted with dichloromethane (2×100 ml). The collected organic phase was dried using magnesium sulfate to evaporate the solvent. The residue was separated and purified using silica gel column chromatography to obtain 2.03 g of Intermediate I-4 (Yield: 78%). This compound was identified using MS/FAB. $C_{20}H_{20}$: calc. 260.37. found 260.45

Synthesis of Intermediate I-5a 3.56 g (20 mmol) of N-bromosuccinimide (NBS) was completely dissolved in 50 ml of dimethylformamide (DMF) to obtain a solution. Afterward, 2.60 g (10 mmol) of Intermediate I-4 was added into the solution and was then stirred at room temperature for about 24 hours. 50 ml of water was added into the reaction solution to obtain a precipitate, which was then extracted using dichloromethane. The aqueous phase was extracted from the reaction solution using dichloromethane (2×50 ml). The collected organic layer was dried using magnesium sulfate to evaporate the solvent. The residue was separately purified using silica gel column chromatography to obtain 2.55 g of Intermediate I-5a (Yield: 75%) This compound was identified using MS/FAB. $C_{20}H_{19}Br$: calc. 339.27. found 339.87

Synthesis of Compound A-1

3.42 g (12 mmol) of 9,9-dimethyl-9H-fluoren-2-yl)-phenyl-amine, 1.83 g (10 mmol) of 4-bromostyrene, 0.18 g (0.2 mmol) of $Pd_2(dba)_3$, 0.04 g (0.4 mmol) of $PtBu_3$, and 1.44 g (15.0 mmol) of NaOtBu were dissolved in 50 ml of toluene, and then refluxed at about 85° C. for about 4 hours. The reaction solution was cooled to room temperature, followed by extraction three times with 40 mL of water and 40 mL of diethyl ether. The collected organic phase was dried using magnesium sulfate to evaporate the solvent. The residue was separately purified using silica gel column chromatography to obtain 3.02 g of Compound A-1 (Yield: 78%) This compound was identified using MS/FAB. $C_{29}H_{25}N$: calc. 387.52. found 387.99

Synthesis of Compound 6

1.70 g (5 mmol) of Intermediate I-5a, 1.94 g (5 mmol) of Compound A-1, 0.056 g (0.25 mmol) of $Pd(OAc)_2$, 0.76 g (0.25 mmol) of tri(o-tolyl)phosphine ($(p-tolyl)_3P$), and 1.019 g (10 mmol) of triethylamine were dissolved in 100 mL of dimethylacetamide (DMAc) to obtain a solution, which was then stirred at about 85° C. for about 4 hours. The reaction solution was cooled to room temperature, followed by extraction three times with 100 mL of water and 100 mL of diethyl ether. The collected organic phase was dried using magnesium sulfate to evaporate the solvent. The residue was separated and purified using silica gel column chromatography to obtain 1.71 g of Compound 6 (Yield: 46%). This compound was identified using MS/FAB. $C_{49}H_{43}N$: calc. 645.87. found 646.15

$^1$H NMR (400 MHz, $CDCl_3$) δ=8.12 (d, 1H), 7.82 (d, 1H), 7.78-7.72 (m, 2H), 7.65 (d, 1H), 7.60 (d, 1H), 7.55-7.53 (m, 2H), 7.51-7.38 (m, 5H), 7.35-7.28 (m, 5H), 7.25-7.23 (m, 4H), 7.18 (d, 1H), 7.06-7.04 (m, 2H), 1.61 (s, 6H), 1.41 (s, 6H), 1.36 (s, 6H)

Synthesis Example 2

Synthesis of Compound 18

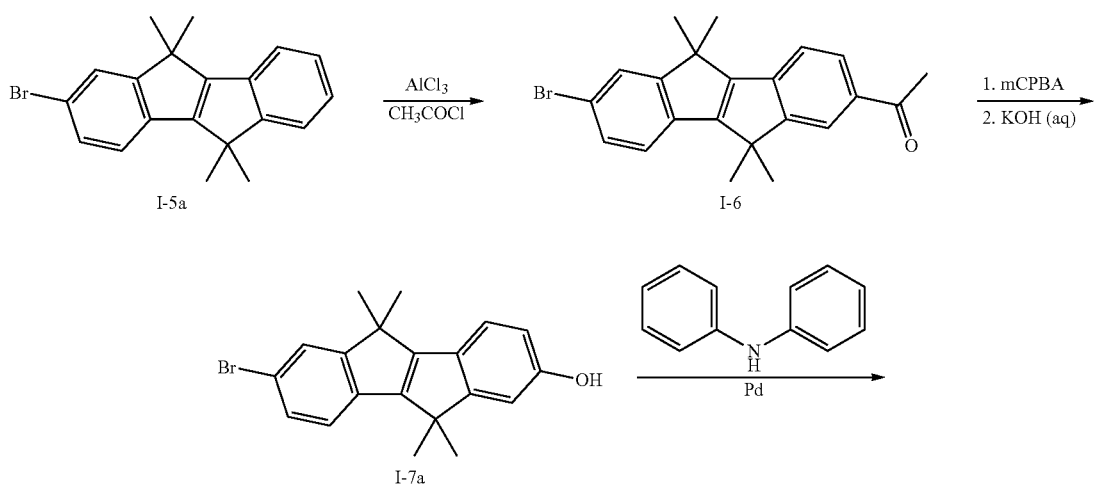

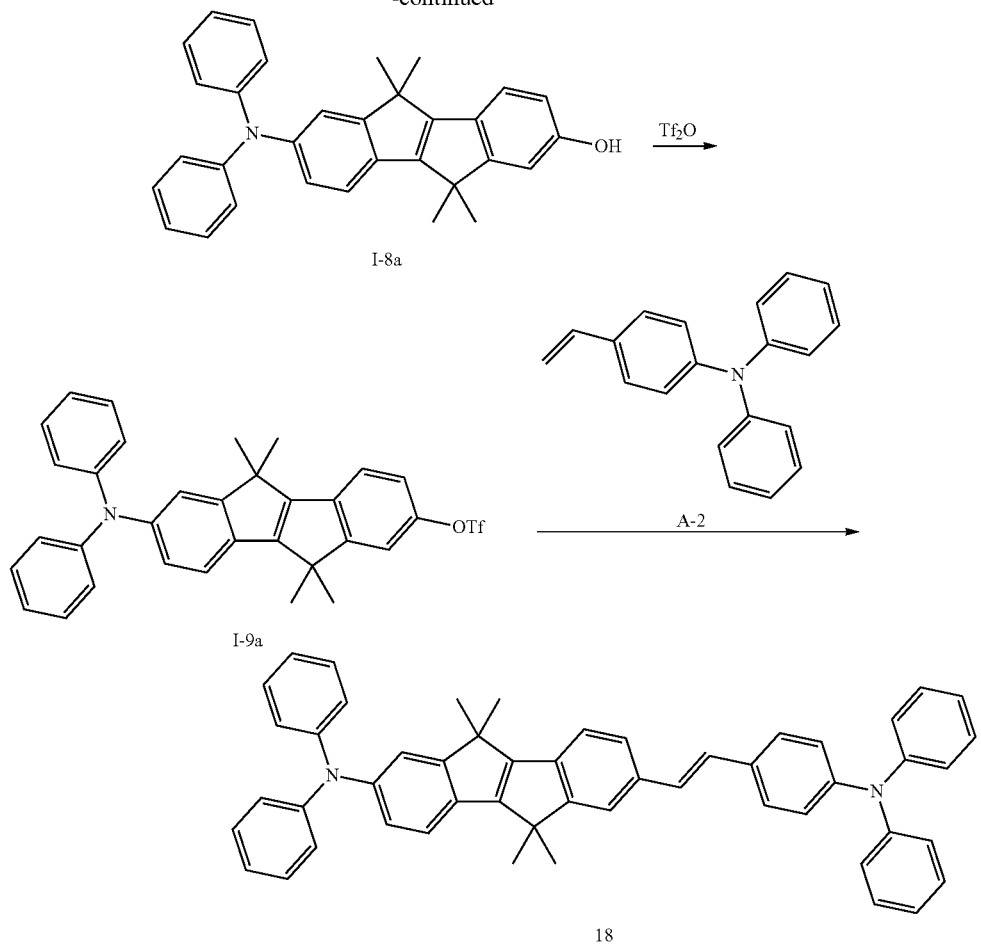

Synthesis of Intermediate I-6

3.4 g (10 mmol) of Intermediate I-5a and 3.33 g (25 mmol) of AlCl$_3$ were dissolved in 50 ml of dichloromethane to obtain a solution, which was then cooled to about 0° C. A solution prepared by dissolving 0.942 g (12 mmol) of acetyl chloride in 10 ml of dichloromethane was slowly added into the solution, and was then stirred at room temperature for about 24 hours. After the reaction, the solution was put into ice and 200 ml of concentrated HCL, and was then stirred for about 45 minutes. The organic phase was separated from the solution, and washed using brine. The resulting aqueous phase was extracted with dichloromethane. The collected organic phase was dried using magnesium sulfate to evaporate the solvent. The residue was separated and purified using silica gel column chromatography to obtain 2.7 g of Intermediate I-6 (Yield: 71%). This compound was identified using MS/FAB. $C_{22}H_{21}BrO$: calc. 381.31. found 381.58

Synthesis of Intermediate I-7a 3.8 g (10 mmol) of Intermediate I-6 was dissolved in hydrocarbon-stabilized CHCl$_3$, and was then cooled to about 0° C. 2.25 g (10 mmol, 77%) of m-chloroperbenzoic acid was slowly added into the solution for reaction, and was then stirred at room temperature for about 3 days. The reaction solution was washed with NaHCO$_3$, H$_2$O and brine sequentially to extract the organic phase therefrom. The collected organic phase was dried using magnesium sulfate to evaporate the solvent. The residue was hydrolyzed using a mixed solution of 10 g of KOH, 200 ml of water, and 50 ml of ethanol. The resulting precipitate was filtrated and then acidified to pH 2 to obtain 2.24 g of Intermediate I-7a (Yield: 63%). This compound was identified using mass spectroscopy/fast atom bombardment (MS/FAB). $C_{20}H_{19}BrO$: calc. 355.27. found 355.34

Synthesis of Intermediate I-8a 3.55 g (10 mmol) of Intermediate I-7a, 2.03 g (12 mmol) of diphenylamine, 0.18 g (0.2 mmol) of Pd$_2$(dba)$_3$, 0.04 g (0.4 mmol) of PtBu$_3$, and 1.44 g (15.0 mmol) of KOtBu were dissolved in 50 mL of toluene to obtain a solution, which was then refluxed at about 85° C. for about 4 hours. The reaction solution was cooled to room temperature, followed by extraction three times with 40 mL of water and 40 mL of diethyl ether. The collected organic phase was dried using magnesium sulfate to evaporate the solvent. The residue was separated and purified using silica gel column chromatography to obtain 3.68 g of Intermediate I-8a (Yield: 83%). This compound was identified using MS/FAB. $C_{32}H_{29}NO$: calc. 443.58. found 443.71

Synthesis of Intermediate I-9a

After 2.22 g (5 mmol) of Intermediate 10 was completely dissolved in 30 ml of toluene, 30 ml of a 30% (w/v) K$_3$PO$_4$ solution was added thereto and cooled to about 0° C. 1 ml (6 mmol) of Tf$_2$O(trifluoromethanesulfonic anhydride) was slowly added into the reaction solution at about 0° C. for reaction, and was then slowly stirred at room temperature for about 30 minutes. A toluene layer was separated from the reaction solution and was then washed with 30 ml of water. The collected organic phase was dried using magnesium sulfate to evaporate the solvent at a reduced pressure. The residue was separated and purified using silica gel column chromatography to obtain 2.62 g of Intermediate I-9a (Yield: 91%). This compound was identified using MS/FAB. $C_{33}H_{28}F_3NO_3S$: calc. 575.64 found 575.85

Synthesis of Compound 18

2.88 g (5 mmol) of Intermediate I-9a, 1.36 g (5 mmol) of Intermediate A-2, 0.056 g (0.25 mmol) of Pd(OAc)$_2$, 0.76 g (0.25 mmol) of tri(o-tolyl)phosphine ((p-tolyl)$_3$P), and 1.019 g (10 mmol) of triethylamine were dissolved in 100 mL of dimethylacetamide (DMAc) to obtain a solution, which was then stirred at about 85° C. for about 4 hours. The reaction solution was cooled to room temperature, followed by extraction three times with 100 mL of water and 100 mL of diethyl ether. The collected organic phase was dried using magnesium sulfate to evaporate the solvent. The residue was separated and purified using silica gel column chromatography to obtain 1.57 g of Compound 18 (Yield: 45%). This compound was identified using MS/FAB. $C_{52}H_{44}N_2$: calc. 696.92. found 697.05

$^1$H NMR (400 MHz, CDCl$_3$) δ=7.96-7.94 (m, 1H), 7.83-7.80 (m, 1H), 7.78-7.76 (m, 2H), 7.70-7.68 (m, 2H), 7.65-7.58 (m, 2H), 7.45-7.40 (m, 8H), 7.38-7.35 (m, 2H), 7.32-7.7.28 (m, 6H), 7.24-7.20 (m, 8H), 1.40 (m, 12H)

Synthesis Example 3

Synthesis of Compound 19

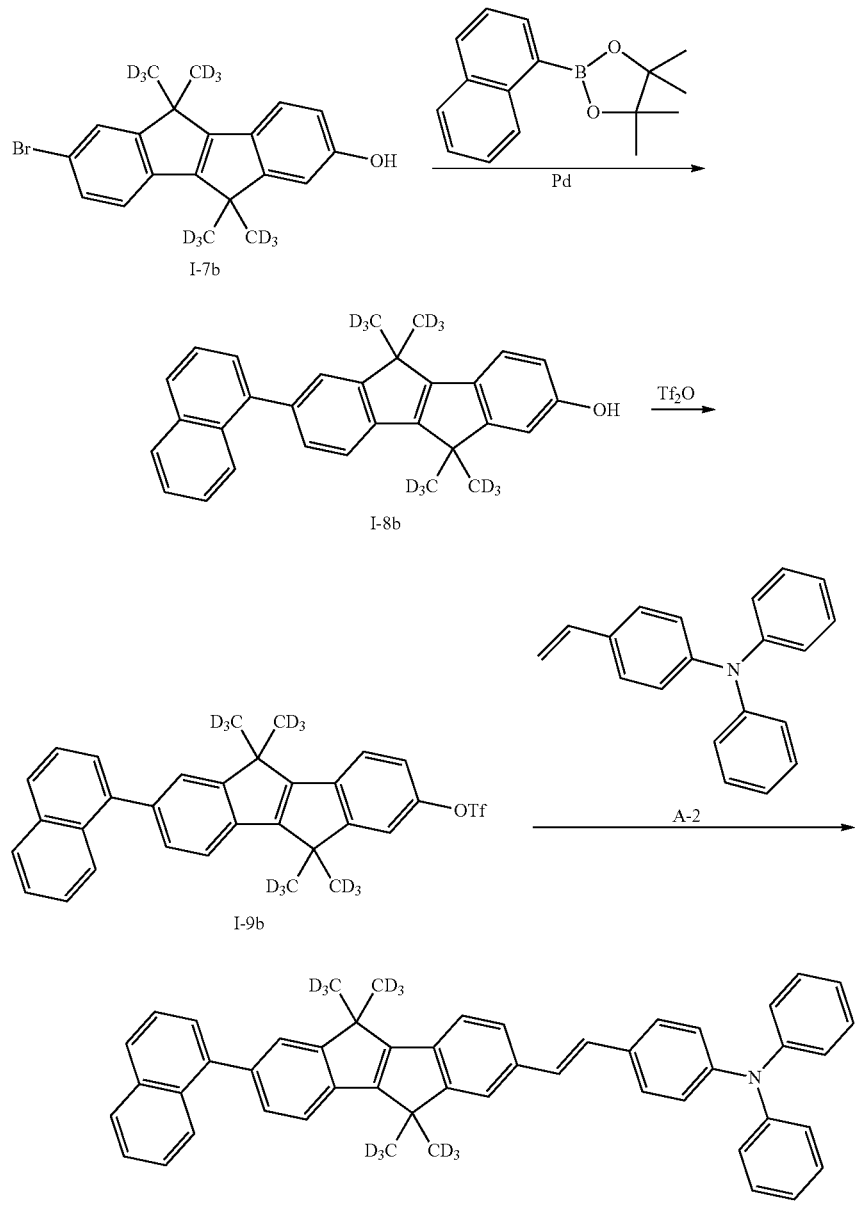

Synthesis of Intermediate I-8b 3.67 g (10.0 mmol) of Intermediate I-7b (which was produced by substituting a hydrogen of Intermediate I-7a with deuterium), 2.54 g (10.0 mmol) of 4,4,5,5,-tetramethyl-2-naphthalen-1-yl-[1,3,2]dioxaborolane, 0.58 g (0.5 mmol) of Pd(PPh$_3$)$_4$, and 4.15 g (30.0 mmol) of K$_2$CO$_3$ were dissolved in 50 mL of a mixed solution of THF/H$_2$O (2:1), which was then stirred at about 70° C. for about 5 hours. The reaction solution was cooled to room temperature, followed by extraction three times with 50 mL of water and 50 mL of diethyl-ether. The collected organic phase was dried using magnesium sulfate to evaporate the solvent. The residue was separated and purified using silica gel column chromatography to obtain 3.23 g of Intermediate I-8b (Yield: 78%). This compound was identified using MS/FAB. C$_{30}$H$_{14}$D$_{12}$O: calc. 414.60. found 414.72

Synthesis of Intermediate I-9b 2.43 g of Intermediate I-9b was synthesized using 2.07 g (5 mmol) of Intermediate I-8b and 1 ml (6 mmol) of Tf$_2$O in the same manner as in the synthesis of Intermediate I-9a in Synthesis Example 2 (Yield: 89%). This compound was identified using MS/FAB. C$_{31}$H$_{13}$D$_{12}$F$_3$O$_3$S: calc. 546.66. found 546.85

Synthesis of Compound 19

1.40 g of Compound 19 was synthesized using 2.73 g (5 mmol) of Intermediate I-9b and 1.36 g (5 mmol) of Intermediate A-2 in the same manner as in the synthesis of Compound 18 in Synthesis Example 2 (Yield: 42%). This compound was identified using MS/FAB. C$_{50}$H$_{29}$D$_{12}$N: calc.; 667.94. found; 668.21

$^1$H NMR (400 MHz, CDCl$_3$) δ=8.23 (d, 1H), 8.08 (d, 1H), 7.87-7.80 (m, 3H), 7.78-7.72 (m, 4H), 7.70-7.64 (m, 4H), 7.61-7.59 (m, 2H), 7.55-7.50 (m, 6H), 7.48-7.44 (m, 4H), 7.40-7.36 (m, 4H)

Synthesis Example 4

Synthesis of Compound 26

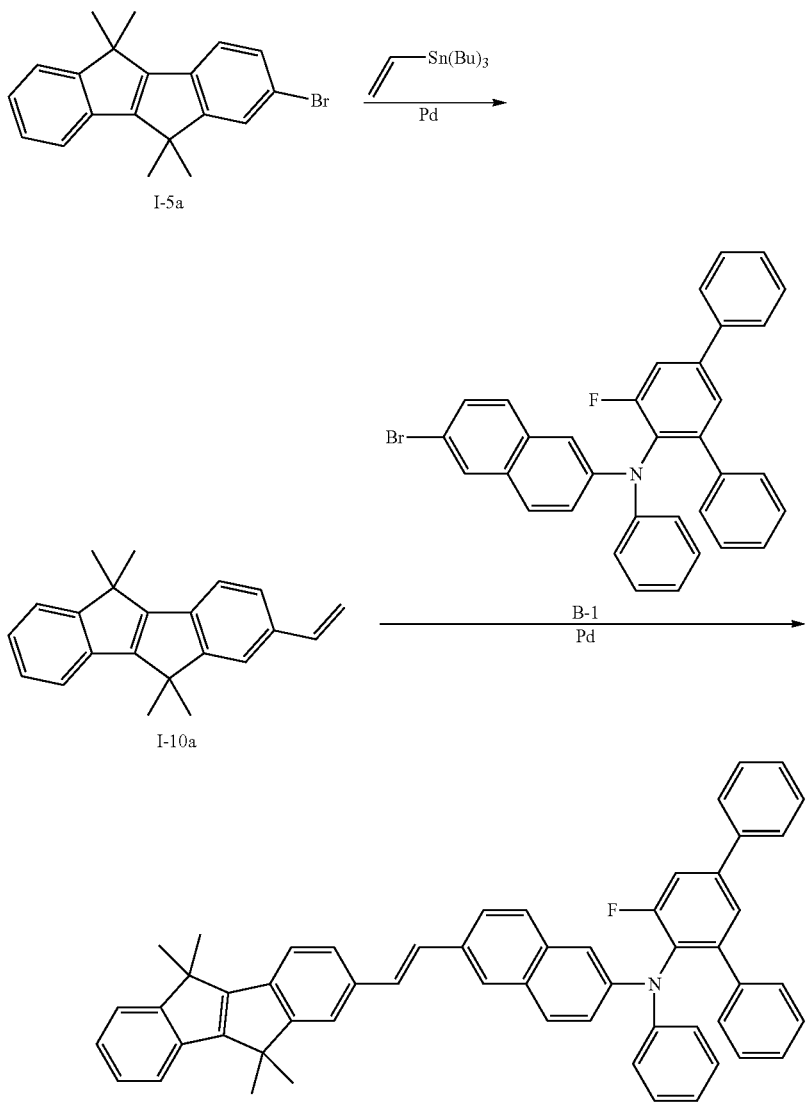

26

Synthesis of Intermediate I-10a 3.4 g (10.0 mmol) of Intermediate I-5a, 3.17 g (10.0 mmol) of tributyl vinyl tin, and 25 mg (0.02 mmol) of Pd(PPh$_3$)$_4$ were dissolved in 50 mL of toluene to obtain a solution, which was then refluxed at about 100° C. in a nitrogen atmosphere for about 48 hours. The reaction solution was cooled to room temperature, followed by extraction three times with 50 mL of water and 50 mL of dichloromethane. The collected organic phase was dried using magnesium sulfate to evaporate the solvent. The residue was separated and purified using silica gel column chromatography to obtain 2.61 g of Intermediate I-10a (Yield: 91%). This compound was identified using MS/FAB. C$_{22}$H$_{22}$: calc.; 286.41. found; 286.58

Synthesis of Compound 26

1.61 g of Compound 26 was synthesized using 1.43 g (5 mmol) of Intermediate I-10a and 2.72 g (5 mmol) of Intermediate B-1 in the same manner as in the synthesis of Compound 18 in Synthesis Example 2 (Yield: 43%). This compound was identified using MS/FAB. C$_{56}$H$_{44}$FN: calc.; 749.95. found; 750.01

$^1$H NMR (400 MHz, CDCl$_3$) δ=8.13-8.11 (m, 1H), 8.09-8.06 (m, 1H), 8.01 (d, 1H) 7.85-7.81 (m, 2H), 7.80-7.68 (m, 13H), 7.62-7.58 (m, 2H), 7.53-7.48 (m, 5H), 7.40-7.37 (m, 3H), 7.31-7.29 (m, 1H), 7.26-7.23 (m, 1H), 7.20-7.18 (m, 2H), 1.41 (s, 6H), 1.36 (s, 6H)

Synthesis Example 5

Synthesis of Compound 30

Synthesis of Intermediate I-11a 1.48 g of Intermediate I-11a was synthesized using 1.43 g (5 mmol) of Intermediate I-10a and 1.87 g (5 mmol) of Compound B-2 in the same manner as in the synthesis of Compound 18 in Synthesis Example 2 (Yield: 51%). This compound was identified using MS/FAB. C$_{44}$H$_{37}$N: calc. 579.77. found 579.85

Synthesis of Compound 30

1.62 g (2.8 mmol) of Intermediate I-11a, 0.081 g (0.08 mmol) of (carbonyl)chloro(hydrido)tris(triphenylphosphine)ruthenium(II) ([(Ph$_3$)P]$_3$Ru(CO)(Cl)H), and 0.56 g (28.0 mmol) of D$_2$O were dissolved in 30 mL of 1,4-dioxane to obtain a solution, which was then stirred at about 80° C. for about 12 hours. The reaction solution was cooled to room temperature, followed by removal of the solvent from the reaction solution, and extraction three times with 50 mL of water and 50 mL of dichloromethane. The collected organic phase was dried using magnesium sulfate to evaporate the solvent. The residue was separated and purified using silica gel column chromatography to obtain 1.24 g of Compound 30 (Yield: 76%). This compound was identified using MS/FAB. C$_{44}$H$_{35}$D$_2$N: calc. 581.78 found; 581.85

$^1$H NMR (400 MHz, CDCl$_3$) δ=8.13-8.12 (m, 1H), 7.90 (d, 1H), 7.85-7.70 (m, 5H) 7.69 (d, 1H), 7.58-7.40 (m, 4H), 7.37-7.32 (m, 4H), 7.30-7.29 (m, 1H), 7.27-7.24 (m, 2H), 7.22-7.20 (m, 4H), 1.41 (s, 6H), 1.36 (s, 6H)

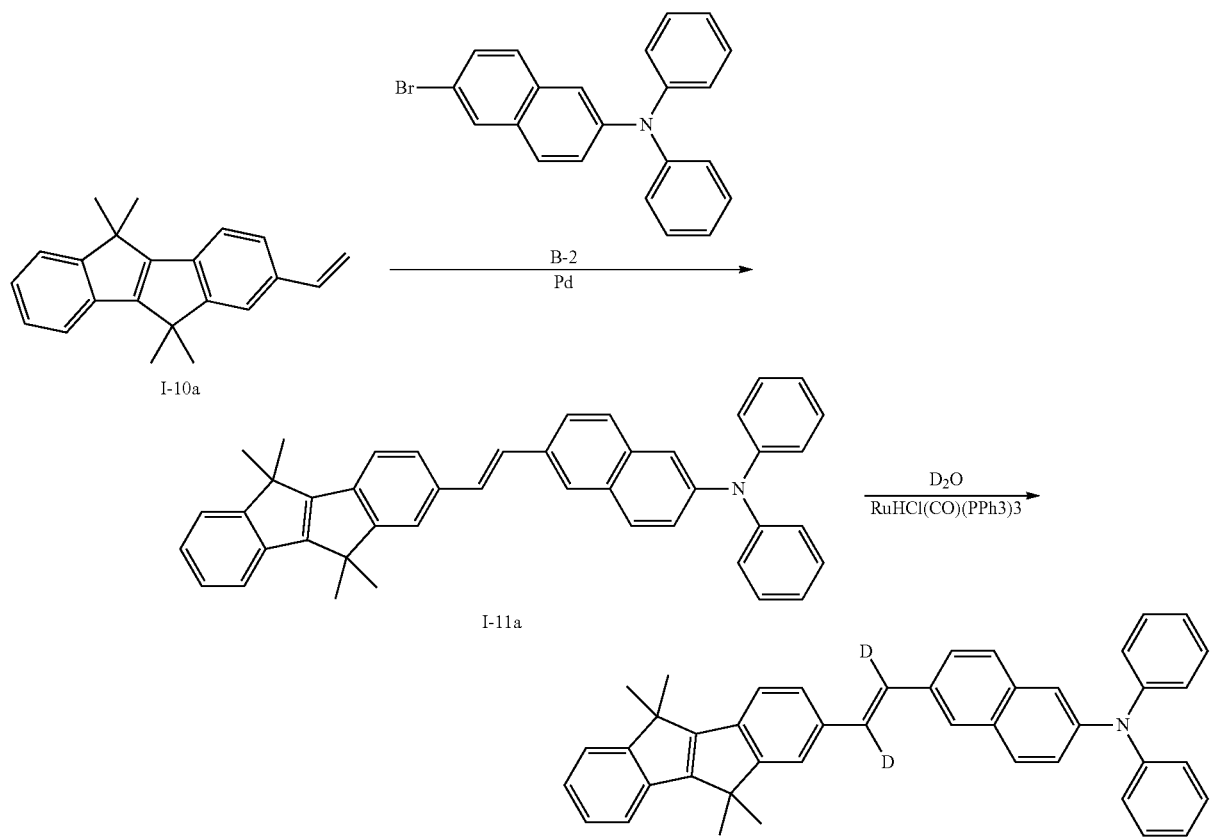

30

Synthesis Example 6

Synthesis of Compound 53

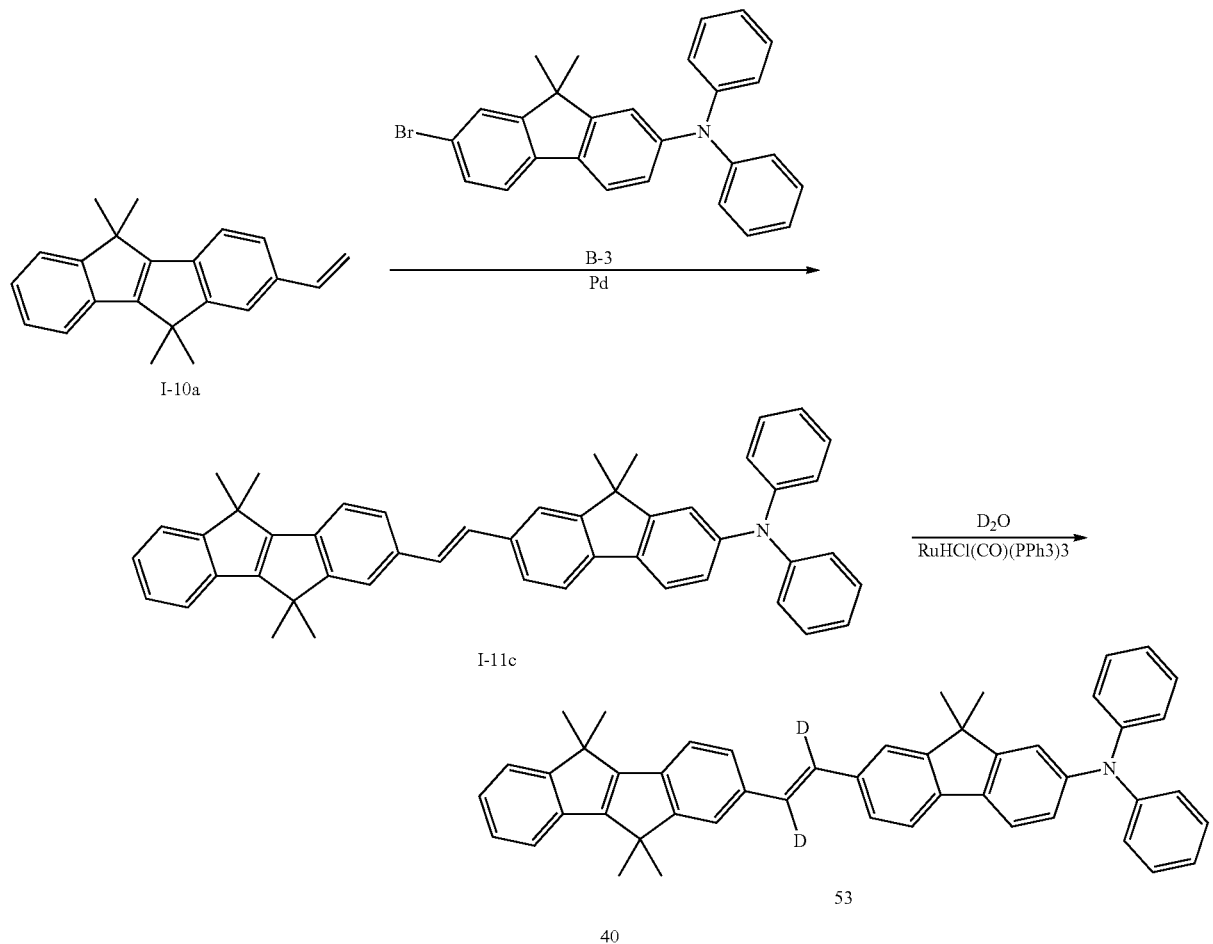

Synthesis of Intermediate I-11b 1.45 g of Intermediate I-11 was synthesized using 1.43 g (5 mmol) of Intermediate I-10a and 2.2 g (5 mmol) of Intermediate B-3 in the same manner as in the synthesis of Intermediate I-11a in Synthesis Example 5 (Yield: 45%). This compound was identified using MS/FAB. $C_{49}H_{43}N$: calc. 645.87. found; 645.95

Synthesis of Compound 53

1.31 g of Compound 53 was synthesized using 1.8 g (2.8 mmol) of Intermediate I-11b and 2.56 g (28.0 mmol) of $D_2O$ in the same manner as in the synthesis of Compound 30 in Synthesis Example 5 (Yield: 72%). This compound was identified using MS/FAB. $C_{49}H_{41}D_2N$: calc. 647.88. found 647.98

$^1$H NMR (400 MHz, $CDCl_3$) δ=8.14-8.13 (m, 1H), 7.93-7.83 (m, 3H), 8.76-7.73 (m, 2H) 7.70-7.58 (m, 5H) 7.52-7.50 (m, 4H) 7.48-7.45 (m, 3H), 7.40-7.38 (m, 1H) 7.36-7.32 (m, 4H), 1.61 (s, 6H), 1.41 (s, 6H), 1.36 (s, 6H)

Synthesis Example 7

Synthesis of Compound 65

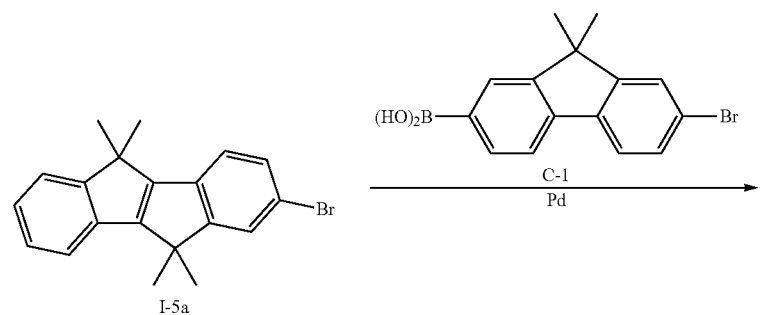

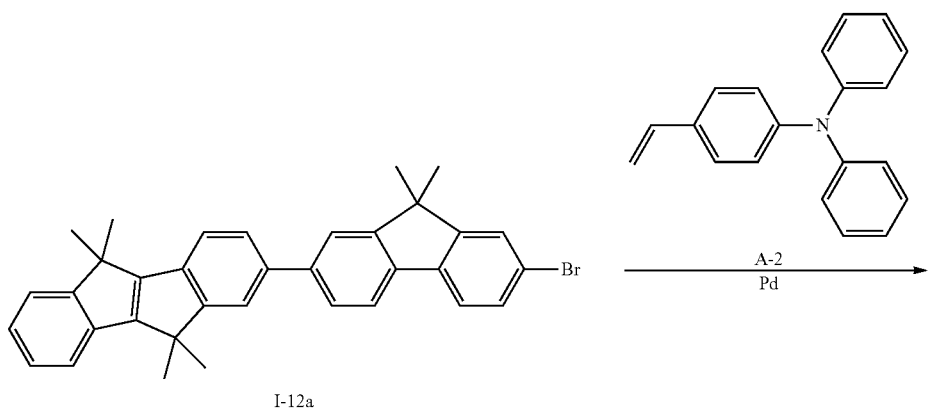

I-12a

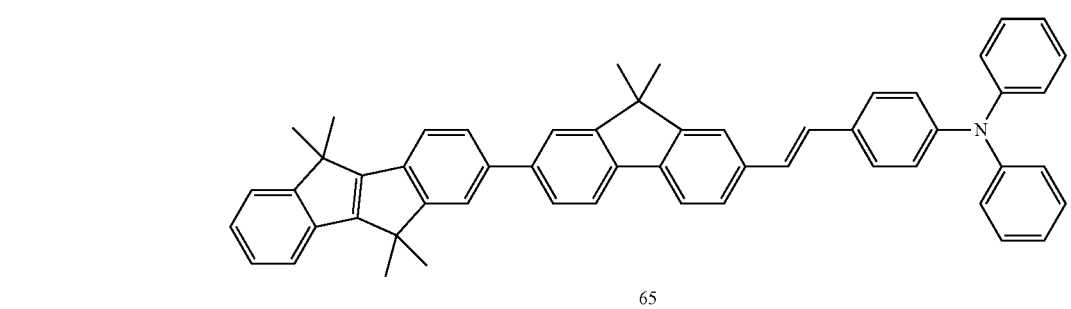

65

Synthesis of Intermediate I-12a 3.4 g (10.0 mmol) of Intermediate I-5a, 3.17 g (10.0 mmol) of Compound C-1, 0.58 g (0.5 mmol) of Pd(PPh$_3$)$_4$, and 4.15 g (30.0 mmol) of K$_2$CO$_3$ were dissolved in 60 mL of a mixed solution of THF and H$_2$O (2:1) to obtain a solution, which was then stirred at about 70° C. for about 5 hours. The reaction solution was cooled to room temperature, followed by extraction three times with 50 mL of water and 50 mL of diethylether. The collected organic phase was dried using magnesium sulfate to evaporate the solvent. The residue was separated and purified using silica gel column chromatography to obtain 4.04 g of Intermediate I-12a (Yield: 76%). This compound was identified using MS/FAB. C$_{35}$H$_{31}$Br: calc. 531.52. found 531.66

Synthesis of Compound 65

1.62 g of Compound 65 was synthesized using 2.66 g (5 mmol) of Intermediate I-12a and 1.36 g (5 mmol) of Compound A-2 in the same manner as in the synthesis of Compound 18 in Synthesis Example 2 (Yield: 45%). This compound was identified using MS/FAB. C$_{55}$H$_{47}$N: calc. 721.97. found 722.02

Synthesis Example 8

Synthesis of Compound 80

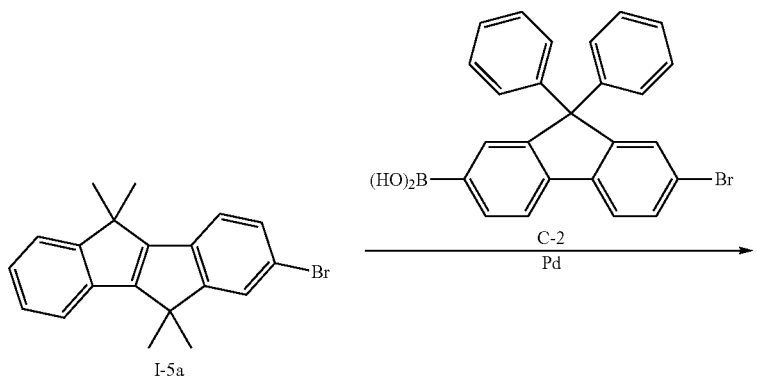

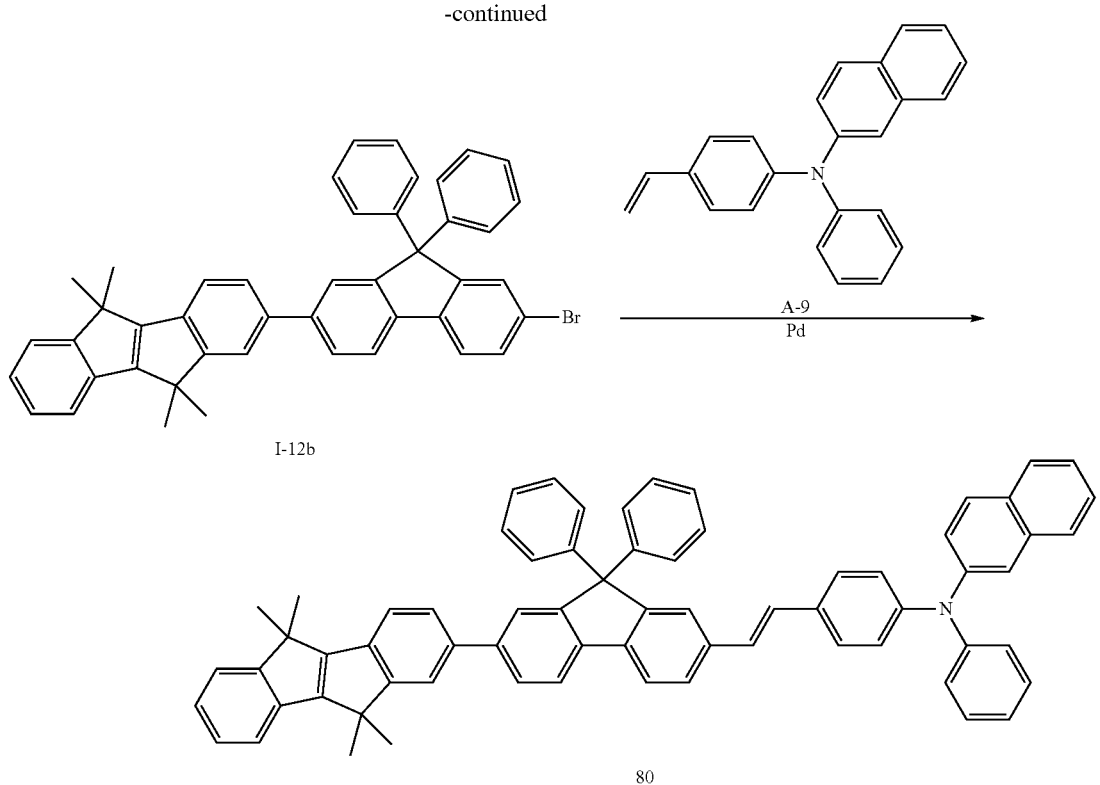

Synthesis of Intermediate I-12b 3.98 g of Intermediate I-12b was synthesized using 3.4 g (10.0 mmol) of Intermediate I-5a and 4.4 g (10 mmol) of Intermediate C-2 in the same manner as in the synthesis of Intermediate I-12a in Synthesis Example 7 (Yield: 75%). This compound was identified using MS/FAB. $C_{35}H_{31}Br$: calc. 531.52. found 531.66

Synthesis of Compound 80

1.97 g of Compound 80 was synthesized using 2.66 g (5 mmol) Intermediate I-12b and 1.61 g (5 mmol) of Intermediate A-9 in the same manner as in the synthesis of Compound 65 in Synthesis Example 7 (Yield: 44%). This compound was identified using MS/FAB. $C_{69}H_{53}N$: calc. 896.17. found 896.23

$^1$H NMR (400 MHz, CDCl$_3$) δ=8.15 (d, 1H), 7.85-7.80 (m, 3H), 7.77-7.42 (m, 20H), 7.40-7.32 (m, 11H) 7.29 (d, 1H), 7.25-7.23 (m, 2H) 7.21-7.19 (m, 1H), 7.15-7.13 (m, 2H), 1.41 (s, 6H), 1.30 (s, 6H)

Synthesis Example 9

Synthesis of Compound 1

1.19 g of Compound 1 was synthesized using Intermediate I-5a and Intermediate A-2 in the same manner as in the synthesis of Compound 6 in Synthesis Example 1 (Yield: 45%). This compound was identified using MS/FAB. $C_{40}H_{35}N$: calc. 529.71. found 529.85

$^1$H NMR (400 MHz, CDCl$_3$) δ=8.12 (d, 1H), 7.82 (d, 1H), 7.73 (d, 1H), 7.64 (d, 1H), 7.48-7.37 (m, 3H), 7.31-7.24 (m, 3H), 7.19-7.12 (m, 5H), 7.01-6.95 (m, 4H), 6.92-6.88 (m, 4H), 1.41 (s, 6H), 1.36 (s, 6H)

Synthesis Example 10

Synthesis of Compound 3

1.36 g of Compound 3 was synthesized using Intermediate I-5a and Intermediate A-3 in the same manner as in the synthesis of Compound 6 in Synthesis Example 1 (Yield: 48%). This compound was identified using MS/FAB. $C_{40}H_{33}F_2N$: calc. 565.69. found 565.85

$^1$H NMR (400 MHz, CDCl$_3$) δ=8.12 (d, 1H), 7.82 (d, 1H), 7.73 (d, 1H), 7.64 (d, 1H), 7.62-7.56 (m, 3H), 7.52-7.42 (m, 3H), 7.40-7.31 (m, 3H), 7.29-7.22 (m, 4H), 7.21-7.14 (m, 4H), 1.41 (s, 6H), 1.36 (s, 6H)

Synthesis Example 11

Synthesis of Compound 7

1.64 g of Compound 7 was synthesized using Intermediate I-5a and Intermediate A-4 in the same manner as in the synthesis of Compound 6 in Synthesis Example 1 (Yield: 47%). This compound was identified using MS/FAB. $C_{52}H_{42}FN$: calc. 699.89. found 699.98

$^1$H NMR (400 MHz, CDCl$_3$) δ=8.12 (d, 1H), 7.82 (d, 1H), 7.74-7.70 (m, 3H), 7.66-7.62 (m, 4H), 7.58-7.51 (m, 5H), 7.46-7.40 (m, 4H), 7.37-7.24 (m, 7H), 7.22-7.16 (m, 3H), 7.14-7.10 (m, 2H), 1.41 (s, 6H), 1.36 (s, 6H)

Synthesis Example 12

Synthesis of Compound 9

1.64 g of Compound 9 was synthesized using Intermediate I-5a and Intermediate A-5 in the same manner as in the synthesis of Compound 6 in Synthesis Example 1 (Yield: 47%). This compound was identified using MS/FAB. $C_{59}H_{45}N$: calc. 768.00. found 768.21

$^1$H NMR (400 MHz, $CDCl_3$) δ=8.12 (d, 1H), 7.92-7.81 (m, 4H), 7.77-7.65 (m, 2H), 7.62-7.58 (m, 6H), 7.53-7.40 (m, 10H), 7.38-7.20 (m, 5H), 7.18-7.11 (m, 2H), 7.08-7.01 (m, 3H), 1.41 (s, 6H), 1.36 (s, 6H)

Synthesis Example 13

Synthesis of Compound 10

1.41 g of Intermediate I-11 as a styryl compound was synthesized using Intermediate I-5b (obtained by substituting the methyl group of Intermediate I-5a with an ethyl group) and Compound A-2 in the same manner as in the synthesis of Compound 6 in Synthesis Example 1 (Yield: 48%). 1.28 g of Compound 10 was synthesized by substituting Intermediate I-11 with deuterium in the same manner as in the synthesis of Compound 30 in Synthesis Example 5 (Yield: 78%). This compound was identified using MS/FAB. $C_{44}H_{41}D_2N$: calc. 587.83. found 587.96

$^1$H NMR (400 MHz, $CDCl_3$) δ=8.01 (d, 1H), 7.86 (d, 1H), 7.75-7.71 (m, 3H), 7.64-7.62 (m, 2H), 7.58-7.50 (m, 2H), 7.44-7.40 (m, 4H), 7.35-7.27 (m, 4H), 7.23-7.18 (m, 4H), 1.89-1.80 (m, 4H), 1.68-1.59 (m, 4H), 0.81-0.78 (m. 12H)

Synthesis Example 14

Synthesis of Compound 12

Intermediate I-5c was synthesized using Intermediate I-5a and $CD_3I$ in the same manner as in the synthesis of Intermediate I-5a in Synthesis Example 1. 1.25 g of Compound 1 was synthesized using Intermediate I-5c and Intermediate A-2 in the same manner as in the synthesis of Compound 6 in Synthesis Example 1 (Yield: 46%). This compound was identified using MS/FAB. $C_{40}H_{23}D_{12}N$: calc. 541.79. found 541.98

$^1$H NMR (400 MHz, $CDCl_3$) δ=8.12 (d, 1H), 7.82 (d, 1H), 7.74-7.72 (m, 1H), 7.64-7.65 (m, 1H), 7.60-7.56 (m, 3H), 7.54-7.48 (m, 3H), 7.43 (s, 1H), 7.36 (s, 1H), 7.28-7.23 (m, 3H), 7.19-7.13 (m, 4H), 7.10-7.04 (m, 4H)

Synthesis Example 15

Synthesis of Compound 14

1.61 g of Compound 14 was synthesized using Intermediate I-7a instead of Intermediate I-7b, 4,4,5,5-tetramethyl-2-naphthalene-2-yl-[1,3,2]dioxaborolane instead of 4,4,5,5-tetramethyl-2-naphthalene-1-yl-[1,3,2]dioxaborolane, and Compound A-8 instead of Compound A-2 in the same manner as in the synthesis of Compound 19 in Synthesis Example 3 (Yield: 47%). This compound was identified using MS/FAB. $C_{52}H_{45}N$: calc. 683.92. found 683.99

$^1$H NMR (400 MHz, $CDCl_3$) δ=8.19 (s, 1H), 8.02 (d, 1H), 7.93-7.70 (m, 6H), 7.67-7.60 (m, 3H), 7.57-7.52 (m, 4H), 7.50-7.38 (m, 6H), 7.36-7.34 (m, 2H), 7.31-7.28 (m, 2H), 7.26-7.24 (m, 2H), 1.87 (s, 6H), 1.40 (s, 6H), 1.37 (s, 6H)

Synthesis Example 16

Synthesis of Compound 16

1.42 g of Compound 16 was synthesized using Intermediate I-5b and Compound A-6 in the same manner as in the synthesis of Compound 6 in Synthesis Example 1 (Yield: 47%). This compound was identified using MS/FAB. $C_{44}H_{42}FN$: calc. 603.81. found 603.95

$^1$H NMR (400 MHz, $CDCl_3$) δ=8.19 (d, 1H), 7.88 (d, 1H), 7.82-7.80 (m, 3H), 7.78-7.76 (m, 1H), 7.73-7.71 (m, 2H), 7.68-7.65 (m, 2H), 7.62-7.60 (m, 2H), 7.57-7.54 (m, 3H), 7.50-7.48 (m, 2H), 7.45-7.40 (m, 1H), 7.38-7.30 (m, 2H), 7.28-7.24 (m, 2H), 1.89-1.78 (m, 4H), 1.68-1.59 (m, 4H), 0.81-0.78 (m. 12H)

Synthesis Example 17

Synthesis of Compound 20

1.53 g of Compound 20 was synthesized using Intermediate I-5b and Compound A-7 in the same manner as in the synthesis of Compound 6 in Synthesis Example 1 (Yield: 48%). This compound was identified using MS/FAB. $C_{46}H_{37}NS$: calc. 635.86. found 635.98

$^1$H NMR (400 MHz, $CDCl_3$) δ=8.18 (d, 1H), 8.13-8.11 (d, 2H), 7.82-7.80 (m, 2H), 7.78-7.76 (m, 1H), 7.72-7.71 (m, 1H), 7.64-7.52 (m, 8H), 7.48-7.40 (m, 4H), 7.38-7.36 (m, 1H), 7.34-7.32 (m, 2H), 7.30-7.28 (m, 1H), 7.26-7.24 (m, 2H), 1.41 (s, 6H), 1.36 (s, 6H)

Synthesis Example 18

Synthesis of Compound 22

1.32 g of Compound 22 was synthesized using Compound B-4 instead of Compound B-1 in the same manner as in the synthesis of Compound 26 in Synthesis Example 4 (Yield: 45%). This compound was identified using MS/FAB. $C_{44}H_{32}D_5N$: calc. 584.80. found 584.95

$^1$H NMR (400 MHz, $CDCl_3$) δ=8.13-8.11 (d, 1H), 8.08-8.07 (m, 1H), 8.05-8.03 (d, 1H), 7.88-7.84 (m, 2H), 7.80-7.77 (m, 2H), 7.62 (d, 1H), 7.56-7.48 (m, 5H), 7.42-7.38 (m, 2H), 7.35-7.32 (m, 2H), 7.31-7.24 (m, 1H), 7.22-7.18 (m, 2H), 1.41 (s, 6H), 1.36 (s, 6H)

Synthesis Example 19

Synthesis of Compound 31

1.47 g of Compound 31 was synthesized using Compound B-5 instead of Compound B-1 in the same manner as in the synthesis of Compound 26 in Synthesis Example 4 (Yield: 44%). This compound was identified using MS/FAB. $C_{50}H_{39}NO$: calc. 669.85. found 669.96

$^1$H NMR (400 MHz, $CDCl_3$) δ=8.13-8.06 (m, 2H), 8.01 (d, 1H), 7.88-7.85 (m, 3H), 7.76-7.68 (m, 4H), 7.63-7.61 (m, 1H), 7.58-7.56 (m, 2H), 7.50-7.44 (m, 2H), 7.42-7.36 (m, 4H), 7.32-7.28 (m, 2H), 7.26-7.24 (m, 3H), 7.22-7.20 (m, 1H), 7.18-7.16 (m, 2H) 1.41 (s, 6H), 1.36 (s, 6H)

Synthesis Example 20

Synthesis of Compound 35

1.59 g of Compound 35 was synthesized using Intermediate I-10b instead of Intermediate I-10a, and Compound B-6 instead of Compound B-1 in the same manner as in the synthesis of Compound 26 in Synthesis Example 4 (Yield: 45%). This compound was identified using MS/FAB. $C_{53}H_{42}N_2$: calc. 706.91. found 707.21

$^1$H NMR (400 MHz, $CDCl_3$) δ=8.68-8.67 (m, 1H), 8.35-8.32 (m, 1H), 8.09-8.06 (m, 1H), 8.01 (d, 1H) 7.95 (d, 1H), 7.84-7.68 (m, 10H), 7.65-7.63 (m, 3H), 7.55-7.47 (m, 2H), 7.44-7.39 (m, 5H), 7.36-7.34 (m, 2H), 7.30-7.27 (m, 1H), 7.24-7.22 (m, 2H), 1.42 (s, 6H), 1.40 (s, 6H)

Synthesis Example 21

Synthesis of Compound 39

1.48 g of Compound 39 was synthesized using Intermediate I-10c instead of Intermediate I-10a, and Compound B-7 instead of Compound B-1 in the same manner as in the synthesis of Compound 30 in Synthesis Example 5 (Yield: 44%; deuterium substitution yield: 79%). This compound was identified using MS/FAB. $C_{50}H_{27}D_{14}N$: calc. 669.95. found; 670.11

$^1$H NMR (400 MHz, $CDCl_3$) δ=8.12-8.11 (m, 1H), 7.91-7.89 (m, 1H), 7.85-7.83 (m, 1H) 7.82-7.80 (m, 1H) 7.78-7.75 (m, 3H) 7.70-7.66 (m, 3H), 7.60-7.54 (m, 5H) 7.50-7.46 (m, 3H), 7.40-7.36 (m, 2H), 7.32-7.30 (m, 2H), 7.28-7.26 (m, 2H), 7.20-7.19 (m, 1H), 7.18-7.15 (m, 2H)

Synthesis Example 22

Synthesis of Compound 40

1.49 g of Compound 40 was synthesized using Intermediate I-10d instead of Intermediate I-10a, and Compound B-8 instead of Compound B-1 in the same manner as in the synthesis of Compound 26 in Synthesis Example 4 (Yield: 43%). This compound was identified using MS/FAB. $C_{52}H_{53}N$: calc. 691.98. found 692.02

$^1$H NMR (400 MHz, $CDCl_3$) δ=8.12-8.11 (m, 1H), 7.91-7.89 (m, 1H), 7.85-7.83 (m, 1H) 7.82-7.80 (m, 1H) 7.78-7.75 (m, 3H) 7.70-7.66 (m, 3H), 7.60-7.54 (m, 5H) 7.50-7.46 (m, 3H), 7.40-7.36 (m, 2H), 7.32-7.30 (m, 2H), 7.28-7.26 (m, 2H), 7.20-7.19 (m, 1H), 7.18-7.15 (m, 2H)

Synthesis Example 23

Synthesis of Compound 44

1.51 g of Compound 44 was synthesized using Intermediate I-10a, and Compound B-9 instead of Compound B-1 in the same manner as in the synthesis of Compound 26 in Synthesis Example 4 (Yield: 48%). This compound was identified using MS/FAB. $C_{47}H_{38}N_2$: calc. 630.82. found 630.98

$^1$H NMR (400 MHz, $CDCl_3$) δ=8.51 (d, 1H), 8.15-8.09 (m, 2H), 8.06-8.04 (m, 1H) 7.88-7.82 (m, 3H) 7.72-7.68 (m, 2H) 7.60-7.56 (m, 4H), 7.54-7.50 (m, 3H) 7.48-7.37 (m, 7H), 7.32-7.28 (m, 2H), 7.26-7.24 (m, 1H), 1.41 (s, 6H), 1.36 (s, 6H)

Synthesis Example 24

Synthesis of Compound 45

1.38 g of Compound 45 was synthesized using Intermediate I-10a, and Compound B-10 instead of Compound B-1, in the same manner as in the synthesis of Compound 30 in Synthesis Example 5 (Yield: 47% I 78% with deuterium substitution). This compound was identified using MS/FAB. $C_{48}H_{37}D_2N$: calc. 631.84. found 631.95

$^1$H NMR (400 MHz, $CDCl_3$) δ=8.50-8.46 (m, 2H), 8.14-8.13 (m, 1H), 8.02 (s, 1H) 7.87-7.81 (m, 2H) 7.76-7.66 (m, 4H) 7.56-7.46 (m, 4H), 7.43-7.38 (m, 4H) 7.35-7.33 (m, 1H), 7.31-7.28 (m, 2H), 7.26-7.23 (m, 4H), 1.41 (s, 6H), 1.36 (s, 6H)

Synthesis Example 25

Synthesis of Compound 46

1.67 g of Compound 46 was synthesized using Intermediate I-10e instead of Intermediate I-10a, and Compound B-11 instead of Compound B-1, in the same manner as in the synthesis of Compound 30 in Synthesis Example 5 (Yield: 46%; 77% with deuterium substitution). This compound was identified using MS/FAB. $C_{58}H_{44}D_2N$: calc. 773.01. found 773.21

$^1$H NMR (400 MHz, $CDCl_3$) δ=8.16-8.14 (m, 2H), 8.07-8.01 (m, 3H), 7.75-7.71 (m, 2H) 7.68-7.58 (m, 5H) 7.54-7.40 (m, 7H) 7.35-7.30 (m, 5H), 7.27-7.24 (m, 2H) 7.22-7.20 (m, 2H), 7.18-7.15 (m, 4H), 1.43 (s, 6H), 1.40 (s, 6H)

Synthesis Example 26

Synthesis of Compound 48

1.61 g of Compound 48 was synthesized using Intermediate I-10a, and Compound B-12 instead of Compound B-1, in the same manner as in the synthesis of Compound 26 in Synthesis Example 4 (Yield: 41%). This compound was identified using MS/FAB. $C_{59}H_{47}NO$: calc. 786.01. found 786.22

$^1$H NMR (400 MHz, $CDCl_3$) δ=8.15-8.14 (m, 1H), 8.08-8.07 (m, 1H), 8.01-7.99 (m, 1H) 7.88-7.86 (m, 2H) 7.78-7.72 (m, 3H) 7.70-7.64 (m, 5H), 7.63-7.48 (m, 12H) 7.40-7.28 (m, 2H), 7.23-7.21 (m, 1H), 7.18-7.16 (m, 1H), 1.61 (s, 6H), 1.41 (s, 6H), 1.36 (s, 6H)

Synthesis Example 27

Synthesis of Compound 49

1.63 g of Compound 49 was synthesized using Intermediate I-10f instead of Intermediate I-10a, and Compound B-13 instead of Compound B-1, in the same manner as in the synthesis of Compound 26 in Synthesis Example 4 (Yield: 42%). This compound was identified using MS/FAB. $C_{56}H_{43}NS$: calc. 762.01. found 762.21

$^1$H NMR (400 MHz, $CDCl_3$) δ=8.13-8.11 (m, 2H), 8.06-8.04 (m, 1H), 8.00-7.92 (m, 5H) 7.89-7.87 (m, 2H) 7.76-7.64 (m, 9H) 7.63-7.60 (m, 2H), 7.57-7.53 (m, 1H) 7.50-7.46 (m, 4H), 7.40-7.35 (m, 2H), 7.32-7.29 (m, 1H), 7.27-7.25 (m, 2H), 1.40 (s, 6H), 1.37 (s, 6H)

Synthesis Example 28

Synthesis of Compound 50

1.82 g of Compound 50 was synthesized using Intermediate I-10g instead of Intermediate I-10a, and Compound B-10 instead of Compound B-1, in the same manner as in the synthesis of Compound 26 in Synthesis Example 4 (Yield: 39%). This compound was identified using MS/FAB. $C_{72}H_{53}N$: calc. 932.20. found 932.32

$^1$H NMR (400 MHz, $CDCl_3$) δ=8.48-8.46 (m, 2H), 8.38-8.34 (m, 1H), 7.96-7.94 (m, 1H), 7.93-7.85, (m, 6H) 7.82-7.78 (m, 4H), 7.76-7.74 (m, 4H) 7.72-7.70 (m, 1H), 7.64-7.52 (m, 9H) 7.50-7.46 (m, 4H), 7.40-7.35 (m, 3H), 7.32-7.30 (m, 2H), 7.28-7.26 (m, 4H), 1.41 (s, 6H), 1.40 (s, 6H)

Synthesis Example 29

Synthesis of Compound 52

1.69 g of Compound 52 was synthesized using Intermediate I-10a, and Compound B-14 instead of Compound B-1, in the same manner as in the synthesis of Compound 26 in Synthesis Example 4 (Yield: 43%). This compound was identified using MS/FAB. $C_{59}H_{46}FN$: calc. 788.00. found 788.12

$^1$H NMR (400 MHz, $CDCl_3$) δ=8.13-8.11 (m, 1H), 7.88-7.86 (m, 2H), 7.80-7.76 (m, 2H), 7.72-7.60 (m, 10H) 7.54-7.50 (m, 8H), 7.47-7.42 (m, 4H) 7.38-7.34 (m, 4H), 7.31-7.30 (m, 1H) 7.28-7.24 (m, 2H), 1.41 (s, 6H), 1.36 (s, 6H)

Synthesis Example 30

Synthesis of Compound 55

1.55 g of Compound 55 was synthesized using Intermediate I-10a, and Compound B-15 instead of Compound B-1, in the same manner as in the synthesis of Compound 26 in Synthesis Example 4 (Yield: 48%). This compound was identified using MS/FAB. $C_{49}H_{41}N$: calc. 643.86. found 643.95

$^1$H NMR (400 MHz, $CDCl_3$) δ=8.14-8.10 (m, 3H), 7.98-7.94 (m, 2H), 7.88-7.85 (m, 3H), 7.77-7.70 (m, 3H), 7.65-7.60 (m, 9H), 7.54-7.50 (m, 1H), 7.47-7.43 (m, 2H), 1.63 (s, 6H), 1.41 (s, 6H), 1.36 (s, 6H)

Synthesis Example 31

Synthesis of Compound 57

1.46 g of Compound 57 was synthesized using Intermediate I-10a, and Compound B-16 instead of Compound B-1, in the same manner as in the synthesis of Compound 26 in Synthesis Example 4 (Yield: 42%). This compound was identified using MS/FAB. $C_{52}H_{42}N_2$: calc. 694.90. found 694.98

$^1$H NMR (400 MHz, $CDCl_3$) δ=8.14-8.13 (m, 1H), 8.05-8.03 (m, 1H), 7.95-7.90 (m, 2H), 7.86-7.84, (m, 1H) 7.80-7.78 (m, 1H), 7.70-7.66 (m, 5H) 7.64-7.62 (m, 3H), 7.60-7.56 (m, 4H) 7.50-7.46 (m, 5H), 7.43-7.40 (m, 1H), 7.35-7.32 (m, 2H), 7.28-7.25 (m, 4H), 1.41 (s, 6H), 1.36 (s, 6H)

Synthesis Example 32

Synthesis of Compound 59

1.62 g of Compound 59 was synthesized using Intermediates I-5a, Compound C-3 instead of Compound C-1, and Compound A-10 instead of Compound A-2, in the same manner as in the synthesis of Compound 65 in Synthesis Example 7 (Yield: 42). This compound was identified using MS/FAB. $C_{58}H_{46}N_2$: calc. 771.00. found 771.13

$^1$H NMR (400 MHz, $CDCl_3$) δ=8.25-8.23 (m, 1H), 8.17-8.13 (m, 1H), 8.08-8.06 (m, 1H), 8.04-8.02 (m, 2H), 7.88-7.65 (m, 20H), 7.60-7.56 (m, 2H), 7.51-7.48 (m, 4H), 7.46-7.43 (m, 1H), 7.40-7.35 (m, 2H), 1.41 (s, 6H), 1.30 (s, 6H)

Synthesis Example 33

Synthesis of Compound 61

1.55 g of a styryl compound (intermediate I-12) was synthesized using Intermediates I-5a, Compound C-3 instead of Compound C-1 and Compound A-11 instead of Compound A-2, in the same manner as in the synthesis of Compound 65 in Synthesis Example 7 (Yield: 41%). 1.60 g of Compound 61 was synthesized by substituting Intermediate I-12 with deuterium in the same manner as in the synthesis of Compound 30 in Synthesis Example 5 (Yield: 75%). This compound was identified using MS/FAB. $C_{58}H_{45}D_2N$: calc. 760.01. found 760.14

$^1$H NMR (400 MHz, $CDCl_3$) δ=8.14-8.12 (m, 1H), 7.98-7.94 (m, 1H), 7.88-7.86 (m, 2H), 7.80-7.77 (m, 4H) 7.72-7.60 (m, 17H) 7.55-7.50 (m, 2H), 7.45-7.40 (m, 6H), 1.41 (s, 6H), 1.30 (s, 6H)

Synthesis Example 34

Synthesis of Compound 62

1.71 g of Compound 62 was synthesized using Intermediate I-5a, Compound C-3 instead of Compound C-1, and Compound A-12 instead of Compound A-2, in the same manner as in the synthesis of Compound 65 in Synthesis Example 7 (Yield: 41%). This compound was identified using MS/FAB. $C_{64}H_{51}N$: calc. 834.10. found 834.23

$^1$H NMR (400 MHz, $CDCl_3$) δ=8.14-8.13 (m, 1H), 7.95-7.93 (m, 1H), 7.88-7.78 (m, 8H), 7.70-7.51 (m, 19H), 7.48-7.40 (m, 3H), 7.35-7.30 (m, 5H) 7.28-7.24 (m, 2H), 1.41 (s, 6H), 1.30 (s, 6H)

Synthesis Example 35

Synthesis of Compound 64

1.58 g of Compound 64 was synthesized using Intermediate I-5a, Compound C-4 instead of Compound C-1, and Compound A-9 instead of Compound A-2, in the same manner as in the synthesis of Compound 65 in Synthesis Example 7 (Yield: 48%). This compound was identified using MS/FAB. $C_{49}H_{40}N_2$: calc. 656.86. found 656.95

$^1$H NMR (400 MHz, $CDCl_3$) δ=02 (s, 1H), 8.20-8.15 (m, 2H), 7.96-7.92 (m, 2H), 7.87-7.85 (m, 2H) 7.82-7.66 (m, 8H), 7.63-7.59 (m, 2H) 7.50-7.46 (m, 3H), 7.41-7.36 (m, 3H) 7.30-7.25 (m, 2H), 7.22-7.20 (m, 1H), 7.18-7.16 (m, 2H), 1.41 (s, 6H), 1.30 (s, 6H)

Synthesis Example 36

Synthesis of Compound 66

1.47 g of Compound 66 was synthesized using Intermediate I-5a, Compound C-5 instead of Compound C-1, and Compound A-2, in the same manner as in the synthesis of Compound 65 in Synthesis Example 7 (Yield: 43%). This compound was identified using MS/FAB. $C_{52}H_{43}N$: calc. 681.90. found 681.99

$^1$H NMR (400 MHz, $CDCl_3$) δ=8.13 (s, 1H), 8.03-8.00 (m, 1H), 7.93-7.88 (m, 4H), 7.84-7.77, (m, 9H) 7.70-7.66 (m, 3H), 7.50-7.45 (m, 4H) 7.41-7.38 (m, 1H), 7.32-7.25 (m, 4H), 7.22-7.19 (m, 4H), 1.41 (s, 6H), 1.30 (s, 6H)

Synthesis Example 37

Synthesis of Compound 69

1.59 g of Compound 69 was synthesized using Intermediate I-5a, Compound C-6 instead of Compound C-1, and Compound A-13 instead of Compound A-2, in the same manner as in the synthesis of Compound 65 in Synthesis Example 7 (Yield: 44%). This compound was identified using MS/FAB. $C_{54}H_{42}FN$: calc. 723.92. found 724.02

$^1$H NMR (400 MHz, $CDCl_3$) δ=8.18-8.10 (m, 3H), 8.02-7.88 (m, 6H), 7.78-7.76 (m, 1H), 7.72-7.66, (m, 7H) 7.62-7.58 (m, 3H), 7.52-7.48 (m, 3H) 7.40-7.32 (m, 2H), 7.28-7.20 (m, 3H), 7.18-7.16 (m, 2H), 1.41 (s, 6H), 1.37 (s, 6H)

Synthesis Example 38

Synthesis of Compound 71

1.48 g of Compound 71 was synthesized using Intermediate I-5a, Compound C-7 instead of Compound C-1, and Compound A-14 instead of Compound A-2, in the same manner as in the synthesis of Compound 65 in Synthesis Example 7 (Yield: 42%). This compound was identified using MS/FAB. $C_{54}H_{41}N$: calc. 703.91. found 704.12

$^1$H NMR (400 MHz, $CDCl_3$) δ=8.31-8.29 (m, 1H), 8.15-8.12 (m, 3H), 8.04-7.98 (m, 4H), 7.90-7.88 (m, 3H) 7.72-7.70 (m, 2H), 7.66-7.58 (m, 5H) 7.56-7.46 (m, 9H), 7.38-7.36 (m, 2H), 1.41 (s, 6H), 1.39 (s, 6H)

Synthesis Example 39

Synthesis of Compound 73

1.48 g of Compound 73 was synthesized using Intermediate I-5a, Compound C-8 instead of Compound C-1, and Compound A-2, in the same manner as in the synthesis of Compound 65 in Synthesis Example 7 (Yield: 49%). This compound was identified using MS/FAB. $C_{46}H_{39}N$: calc. 605.81. found 605.98

$^1$H NMR (400 MHz, $CDCl_3$) δ=8.17-8.12 (m, 2H), 7.85-7.83 (m, 1H), 7.72-7.70 (m, 1H), 7.52-7.30, (m, 11H) 7.25-7.20 (m, 4H), 7.16-7.12 (m, 4H) 7.10-7.06 (m, 4H), 1.41 (s, 6H), 1.30 (s, 6H)

Synthesis Example 40

Synthesis of Compound 74

1.40 g of Compound 74 was synthesized using Intermediate I-5a, Compound C-9 instead of Compound C-1, and Compound A-15 instead of Compound A-2, in the same manner as in the synthesis of Compound 65 in Synthesis Example 7 (Yield: 41%). This compound was identified using MS/FAB. $C_{52}H_{45}N$: calc. 683.92. found 684.10

$^1$H NMR (400 MHz, $CDCl_3$) δ=8.15-8.09 (m, 2H), 8.06-8.05 (d, 1H), 7.92-7.82 (m, 4H), 7.80-7.50 (m, 11H) 7.45-7.40 (m, 3H), 7.38-7.34 (m, 2H) 7.30-7.28 (m, 2H), 7.24-7.22 (m, 2H), 2.30 (s, 6H), 1.41 (s, 6H), 1.37 (s, 6H)

Synthesis Example 41

Synthesis of Compound 75

1.96 g of Compound 75 was synthesized using Intermediate I-5a, Compound C-10 instead of Compound C-1, and Compound A-2, in the same manner as in the synthesis of Compound 65 in Synthesis Example 7 (Yield: 47%). This compound was identified using MS/FAB. $C_{64}H_{49}N$: calc. 832.08. found 832.18

$^1$H NMR (400 MHz, $CDCl_3$) δ=8.30 (d, 1H), 8.12 (d, 1H), 7.90-7.81 (m, 6H), 7.77 (d, 1H) 7.66-7.62 (m, 2H), 7.58-7.36 (m, 11H) 7.32-7.26 (m, 7H), 7.24-7.22 (m, 2H), 7.20-7.19 (m, 2H), 7.15-7.13 (m, 4H), 1.41 (s, 6H), 1.38 (s, 6H)

Synthesis Example 42

Synthesis of Compound 78

1.79 g of Compound 73 was synthesized using Intermediate I-5a, Compound C-8 instead of Compound C-1, and Compound A-2, in the same manner as in the synthesis of Compound 65 in Synthesis Example 7 (Yield: 49%). This compound was identified using MS/FAB. $C_{55}H_{44}N_2$: calc. 732.95. found 733.04

$^1$H NMR (400 MHz, $CDCl_3$) δ=8.63 (d, 1H), 8.17 (d, 1H), 8.10-8.08 (m, 1H), 7.92-7.60 (m, 8H) 7.55-7.50 (m, 5H), 7.44-7.36 (m, 7H) 7.29-7.27 (m, 1H), 7.25-7.22 (m, 3H), 7.19 (d, 1H), 7.17-7.15 (m, 4H), 1.41 (s, 6H), 1.30 (s, 6H)

<Intermediates>

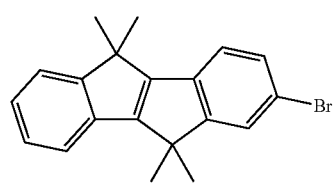

I-5a

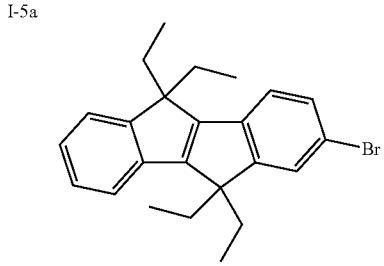

I-5b

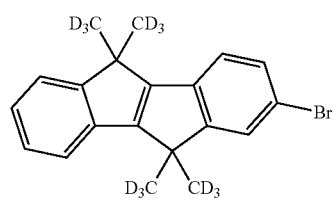

I-5c

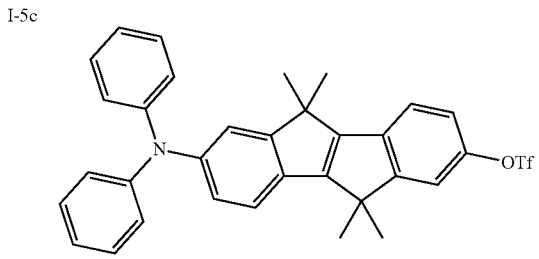

I-9a

-continued
I-9b
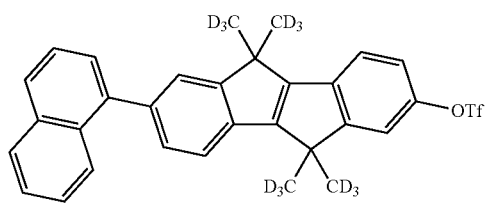
I-9c
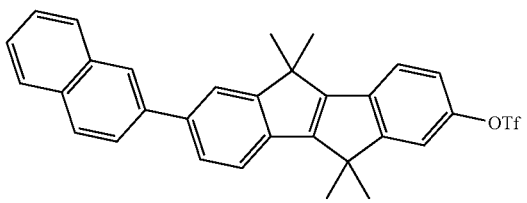
I-10a
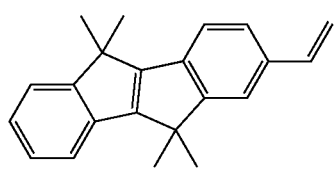
I-10b
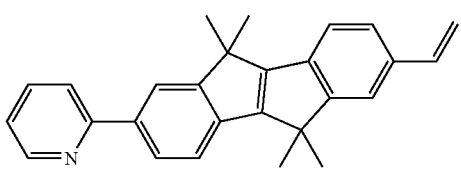
I-10c
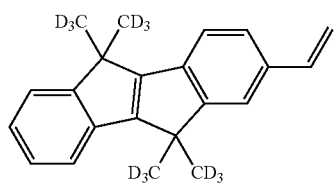
I-10d
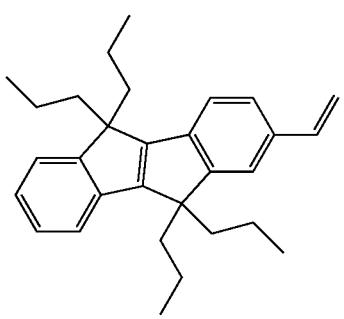
I-10e
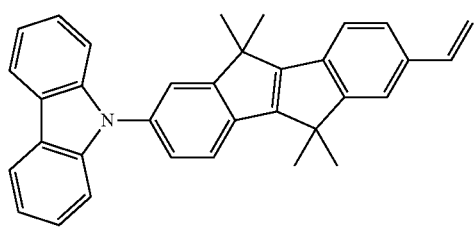
I-10f
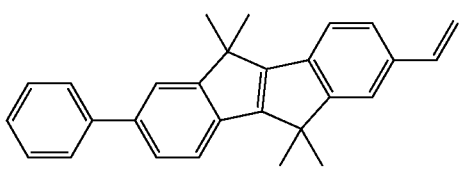
I-10g
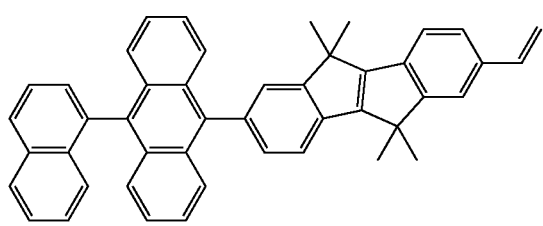
I-11
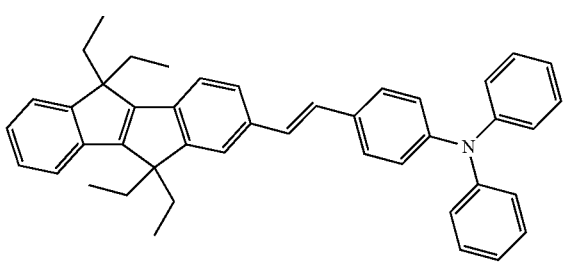

-continued
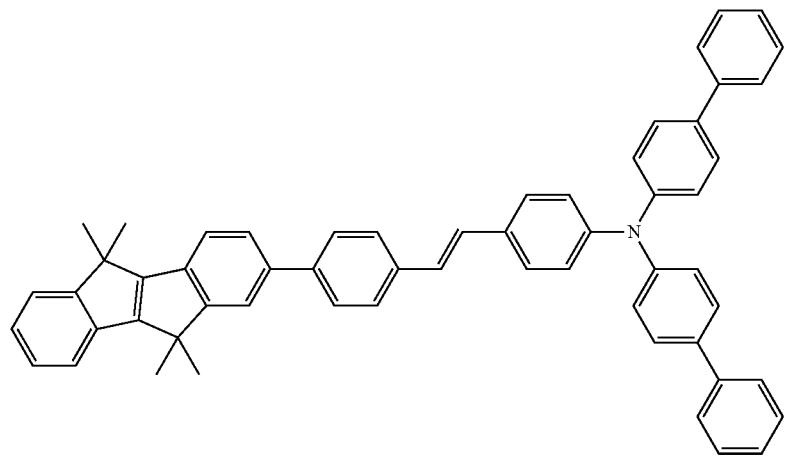
I-12
Compounds A
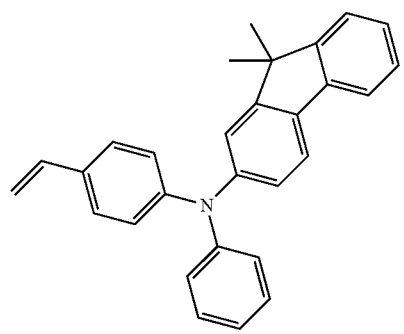
A-1
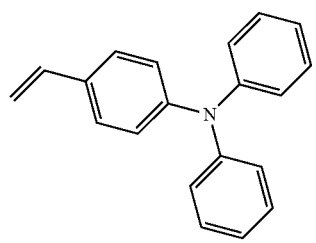
A-2
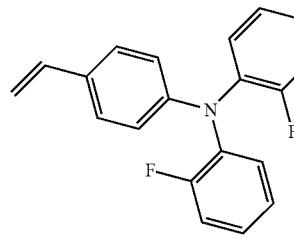
A-3
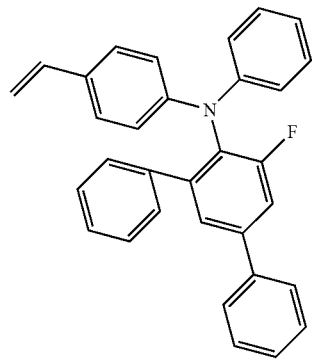
A-4
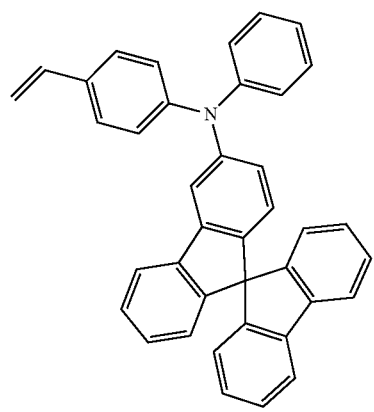
A-5
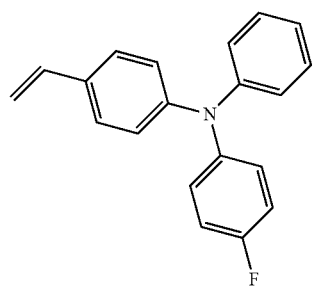
A-6

-continued
A-7
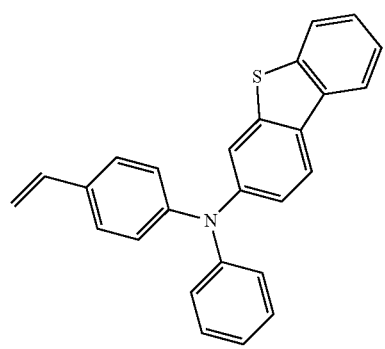
A-8
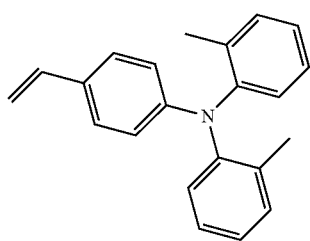
A-9
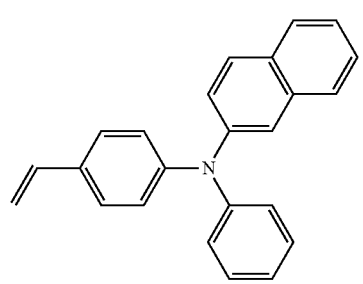
A-10
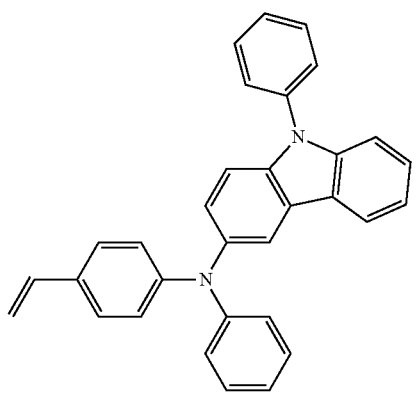
A-11
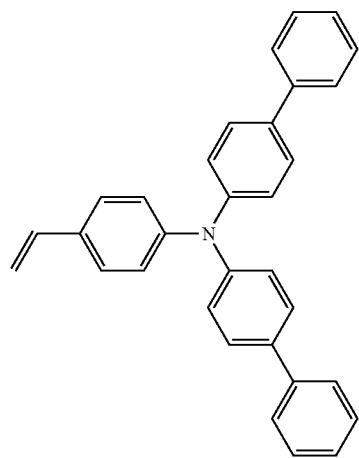
A-12
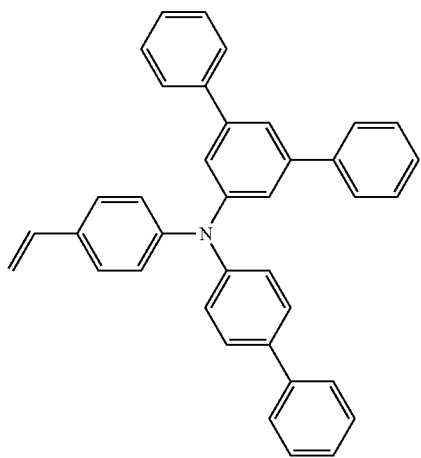
A-13
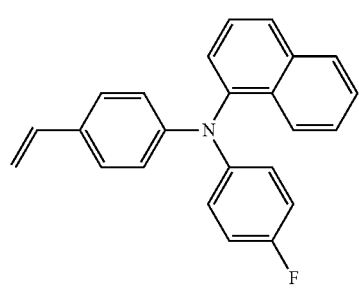
A-14
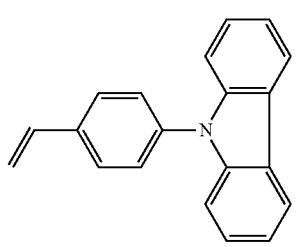

-continued
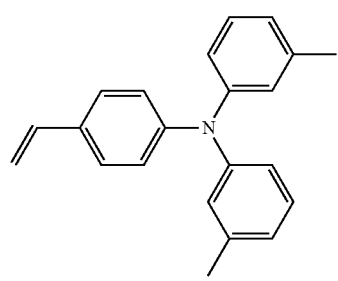
A-15
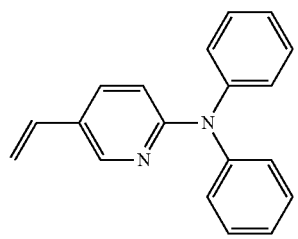
A-16
Compounds B
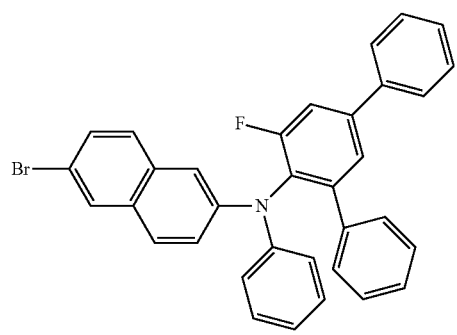
B-1
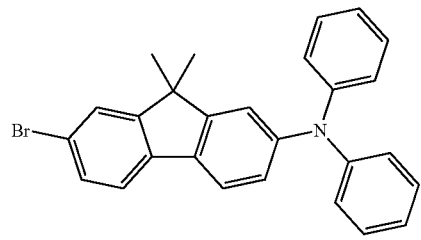
B-2
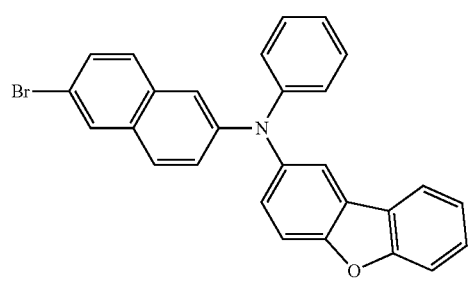
B-3
B-4
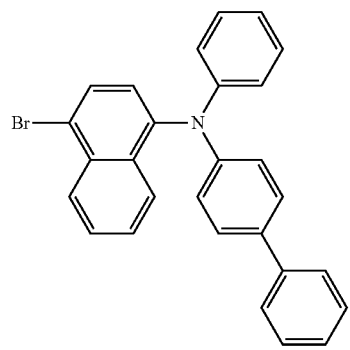
B-5
B-6
B-7
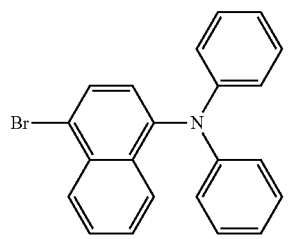
B-8

-continued
B-9
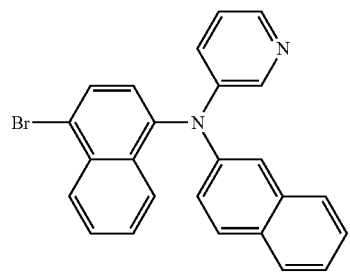
B-10
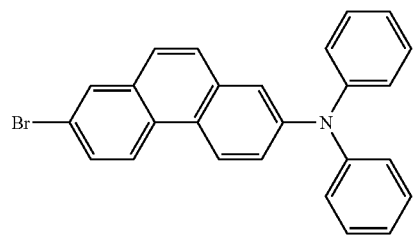
B-11
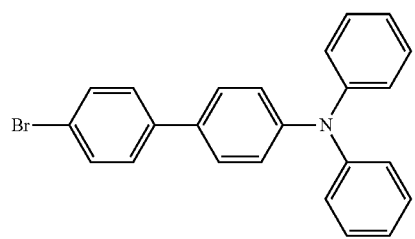
B-12
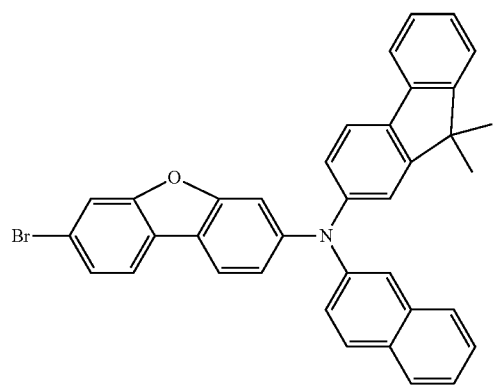
B-13
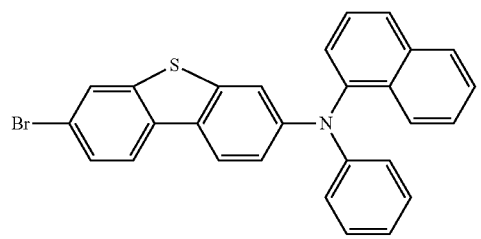
B-14
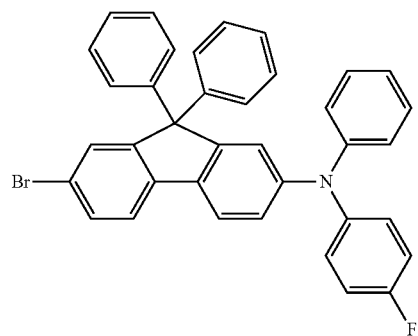
B-15
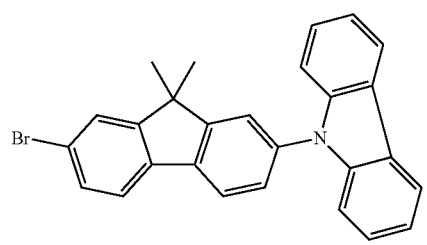
B-16
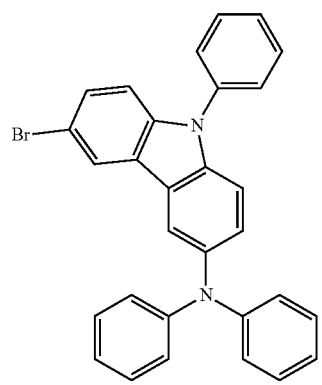
Compounds C
C-1
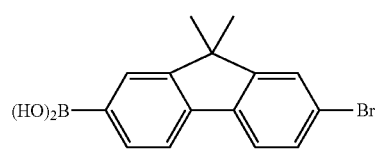
C-2
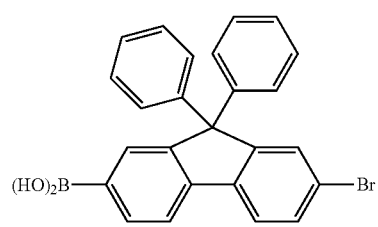

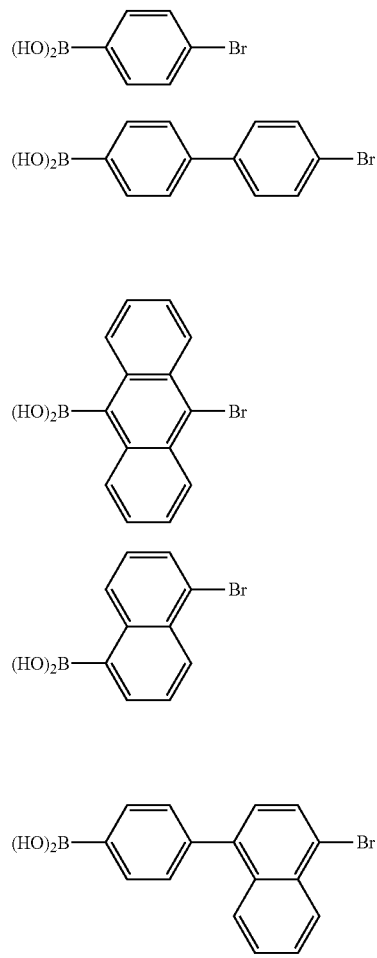

Example 1

A 15 Ω/cm² (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. 2-TNATA was vacuum-deposited on the ITO glass substrate to form an HIL having a thickness of 600 Å on the anode, and then 4,4'-bis[N-(1-naphthyl)-N-phenylamino]biphenyl (NPB) was vacuum-deposited on the HIL to form a HTL having a thickness of 300 Å. 98 wt % of ADN as a blue fluorescent host and 2 wt % of Compound 6 above as a fluorescent dopant were deposited on the HTL to form an EML having a thickness of 300 Å. Alq₃ was vacuum-deposited on the EML to form an ETL having a thickness of 300 Å. LiF was vacuum-deposited on the ETL to form an EIL having a thickness of 10 Å and Al was vacuum-deposited on the EIL to form a cathode having a thickness of 3000 Å, thereby completing the manufacture of an organic light-emitting device.

Example 2

An organic light-emitting device was manufactured in the same manner as in Example 1, except that Compound 18 was used instead of Compound 6 to form the EML.

Example 3

An organic light-emitting device was manufactured in the same manner as in Example 1, except that Compound 19 was used instead of Compound 6 to form the EML.

Example 4

An organic light-emitting device was manufactured in the same manner as in Example 1, except that Compound 26 was used instead of Compound 6 to form the EML.

Example 5

An organic light-emitting device was manufactured in the same manner as in Example 1, except that Compound 30 was used instead of Compound 6 to form the EML.

Example 6

An organic light-emitting device was manufactured in the same manner as in Example 1, except that Compound 53 was used instead of Compound 6 to form the EML.

Example 7

An organic light-emitting device was manufactured in the same manner as in Example 1, except that Compound 65 was used instead of Compound 6 to form the EML.

Example 8

An organic light-emitting device was manufactured in the same manner as in Example 1, except that Compound 80 was used instead of Compound 6 to form the EML.

Example 9

An organic light-emitting device was manufactured in the same manner as in Example 1, except that Compound 6 was used instead of NPB to form the HTL, and DPAVBi was used instead of Compound 6 to form the EML.

Example 10

An organic light-emitting device was manufactured in the same manner as in Example 1, except that Compound 6 was used instead of NPB to form the HTL, and DPAVBi was used instead of Compound 53 to form the EML.

Comparative Example 1

An organic light-emitting device was manufactured in the same manner as in Example 1, except that DPAVBi was used instead of Compound 6 to form the EML.

Comparative Example 2

An organic light-emitting device was manufactured in the same manner as in Example 1, except that Compound D1 below was used instead of Compound 6 as a dopant in forming the EML.

Comparative Example 3

An organic light-emitting device was manufactured in the same manner as in Example 1, except that Compound D-2 below was used instead of Compound 6 as a dopant in forming the EML.

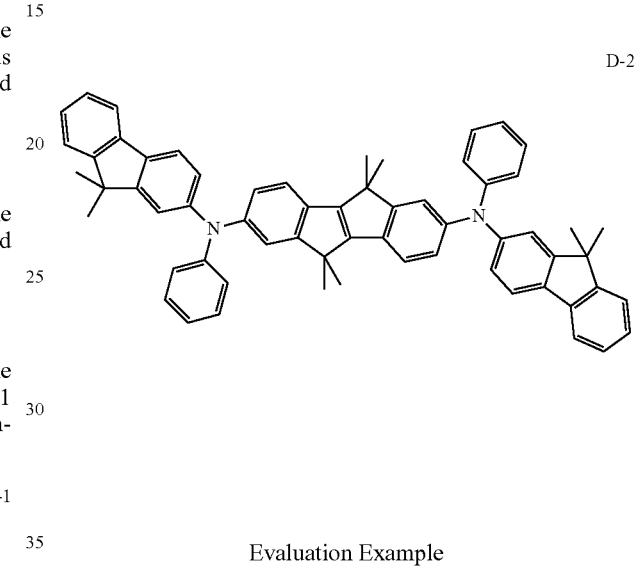

Evaluation Example

The driving voltages, current densities, luminance, efficiencies, light emission colors, and half-life spans of the organic light-emitting devices of Examples 1 to 10 and Comparative Examples 1 to 3 were measured using a PR650 (Spectroscan) Source Measurement Unit. (available from Photo Research, Inc.). The results are shown in Table 1 below.

TABLE 1

| | EML host | EML dopant | Driving Voltage (V) | Current density (mA/cm$^2$) | Luminance (cd/m$^2$) | Efficiency (cd/A) | Emission color | Half-life Span (hr @100 mA/cm$^2$) |
|---|---|---|---|---|---|---|---|---|
| Ex. 1 | ADN | Comp. 6 | 6.53 | 50 | 3,310 | 6.62 | blue | 264 |
| Ex. 2 | ADN | Comp. 18 | 6.67 | 50 | 3,405 | 6.81 | blue | 297 |
| Ex. 3 | ADN | Comp. 19 | 6.65 | 50 | 3,275 | 6.55 | blue | 311 |
| Ex. 4 | ADN | Comp. 26 | 6.53 | 50 | 3,305 | 6.61 | blue | 289 |
| Ex. 5 | ADN | Comp. 30 | 6.65 | 50 | 3,270 | 6.54 | blue | 364 |
| Ex. 6 | ADN | Comp. 53 | 6.59 | 50 | 3,395 | 6.79 | blue | 325 |
| Ex. 7 | ADN | Comp. 65 | 6.63 | 50 | 3,370 | 6.74 | blue | 266 |
| Ex. 8 | ADN | Comp. 80 | 6.67 | 50 | 3,435 | 6.87 | blue | 289 |
| Ex. 9 | ADN | Comp. 6 | 5.46 | 50 | 2,560 | 5.12 | blue | 222 |
| Ex. 10 | ADN | Comp. 53 | 5.39 | 50 | 2,530 | 5.06 | blue | 236 |
| Comp. Ex. 1 | ADN | DPAVBi | 7.35 | 50 | 2,065 | 4.13 | blue | 145 |
| Comp. Ex. 2 | ADN | D-2-6 | 6.12 | 50 | 1,490 | 2.98 | blue | 114 |
| Comp. Ex. 3 | ADN | D-3-7 | 6.13 | 50 | 1,560 | 3.12 | blue | 126 |

[1] Standard current density for half-life span: 100 mA/cm$^2$

Referring to Table 2, the organic light-emitting devices of Examples 1 to 10 were found to have better performance in terms of driving voltage, luminance, efficiency, and lifetime, as compared with the organic light-emitting devices of Comparative Examples 1 to 3.

As described above, an organic light-emitting device including the heterocyclic compound according to embodiments of the present invention may exhibit improved performance, for example, a low driving voltage, high luminance, high efficiency, and a long lifetime.

While the present invention has been illustrated and described with reference to certain exemplary embodiments, it will be understood by those of ordinary skill in the art that various changes may be made to the described embodiments without departing from the spirit and scope of the present invention as defined by the following claims.

What is claimed is:

1. A condensed-cyclic compound represented by Formula 1:

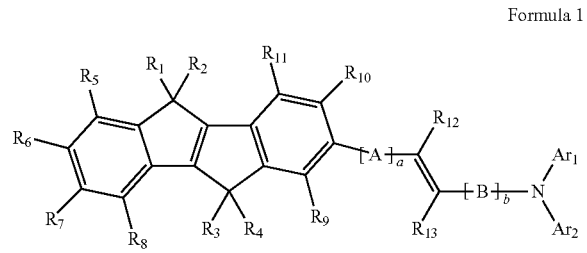

Formula 1 wherein:

$Ar_1$ and $Ar_2$ are each independently a substituted or unsubstituted $C_5$-$C_{40}$ aryl group or a substituted or unsubstituted $C_3$-$C_{40}$ heteroaryl group, and N, $Ar_1$ and $Ar_2$ optionally combine to form a substituted or unsubstituted $C_5$-$C_{20}$ heteroaryl group;

A and B are each a divalent linker, and are each independently one of a substituted or unsubstituted $C_5$-$C_{40}$ arylene group or a substituted or unsubstituted $C_3$-$C_{40}$ heteroarylene group;

a is an integer from 0 to 3, and b is an integer from 0 to 3, wherein when a is 2 or 3, the two or three A groups are identical to or different from each other, and when b is 2 or 3, the two or three B groups are identical to or different from each other;

$R_1$ to $R_{13}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_2$-$C_{40}$ cycloalkenyl group, a substituted or unsubstituted $C_5$-$C_{40}$ aryl group, a substituted or unsubstituted $C_2$-$C_{40}$ heteroaryl group, a substituted or unsubstituted $C_5$-$C_{40}$ aryloxy group, a substituted or unsubstituted $C_5$-$C_{40}$ arylthio group, —Si($R_{31}$)($R_{32}$)($R_{33}$), or —N($R_{34}$)($R_{35}$); and $R_{31}$ through $R_{35}$ are each independently a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_5$-$C_{40}$ aryl group, a substituted or unsubstituted $C_5$-$C_{40}$ aryloxy group, a substituted or unsubstituted $C_5$-$C_{40}$ arylthio group, or a substituted or unsubstituted $C_2$-$C_{40}$ heteroaryl group.

2. The condensed-cyclic compound of claim 1, wherein $Ar_1$ and $Ar_2$ are each independently one of a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted phenanthrenyl group, a substituted or unsubstituted pyranyl group, a substituted or unsubstituted pyridyl group, a substituted or unsubstituted pyrimidinyl group, a substituted or unsubstituted diazinyl group, a substituted or unsubstituted triazinyl group, a substituted or unsubstituted quinolyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted imidazopyridyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolyl group, a substituted or unsubstituted pyridoindolyl group, a substituted or unsubstituted indazolyl group, a substituted or unsubstituted carbazolyl group, a substituted or unsubstituted purinyl group, a substituted or unsubstituted benzoquinolyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furyl group, a substituted or unsubstituted benzofuryl group, a substituted or unsubstituted dibenzofuryl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, or a substituted or unsubstituted tetrazolyl group.

3. The condensed-cyclic compound of claim 1, wherein $Ar_1$ and $Ar_2$ are each independently a group represented by one of Formulae 2A to 2H:

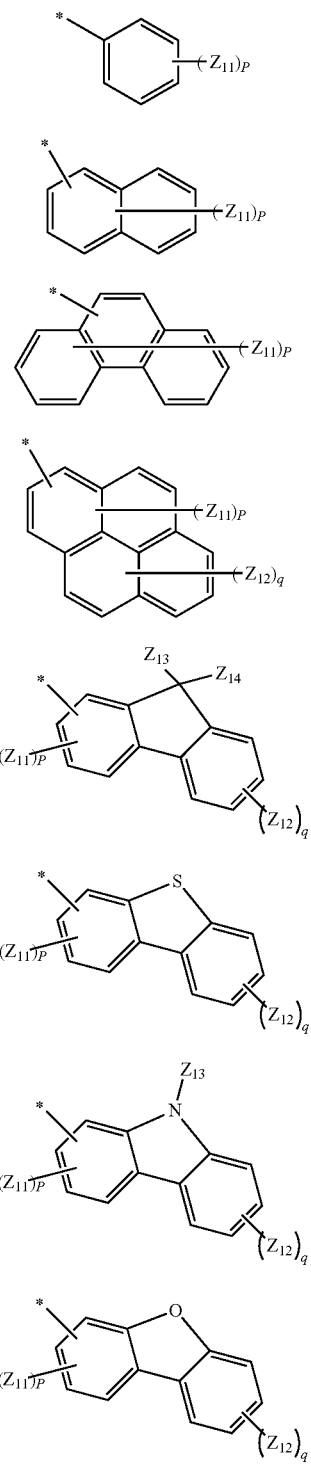

Formula 2A

Formula 2B

Formula 2C

Formula 2D

Formula 2E

Formula 2F

Formula 2G

Formula 2H wherein:
$Z_{11}$, $Z_{12}$, $Z_{13}$, and $Z_{14}$ are each independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridyl group, a substituted or unsubstituted fluorenyl group, or a substituted or unsubstituted quinolyl group, and $Z_{13}$ and $Z_{14}$ optionally combine to form a substituted or unsubstituted $C_5$-$C_{20}$ aryl group;

a plurality of each of $Z_{11}$, $Z_{12}$, $Z_{13}$ and/or $Z_{14}$ are identical to or different from each other;

p is an integer from 1 to 9;

q is an integer from 1 to 5; and

* is a binding site.

4. The condensed-cyclic compound of claim 3, wherein $Ar_1$ and $Ar_2$ are each independently a group represented by one of Formulae 3A to 3W:

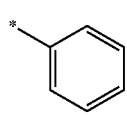

Formula 3A

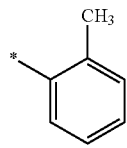

Formula 3B

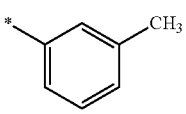

Formula 3C

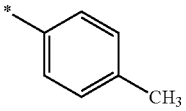

Formula 3D

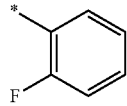

Formula 3E

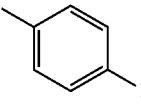

Formula 3F

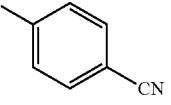

Formula 3G

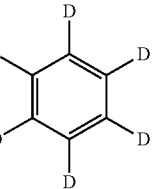

Formula 3H

-continued

Formula 3I 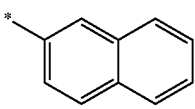

Formula 3J 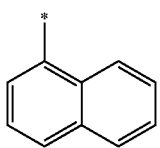

Formula 3K 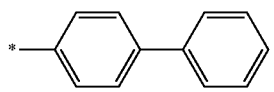

Formula 3L 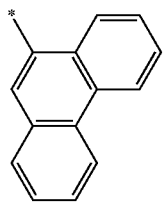

Formula 3M 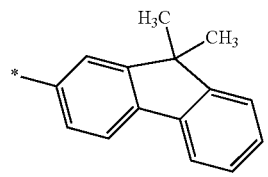

Formula 3N 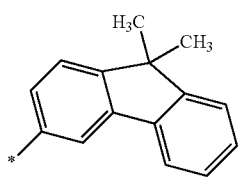

Formula 3O 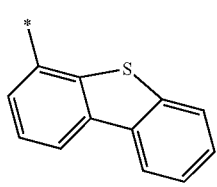

Formula 3P 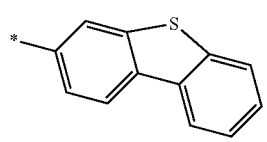

Formula 3Q 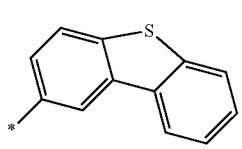

-continued

Formula 3R 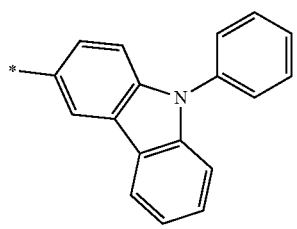

Formula 3S 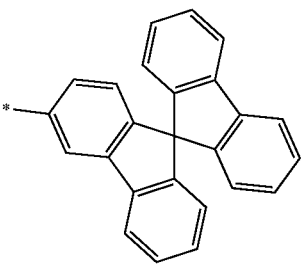

Formula 3T 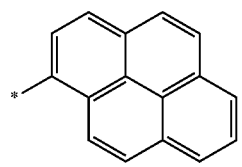

Formula 3U 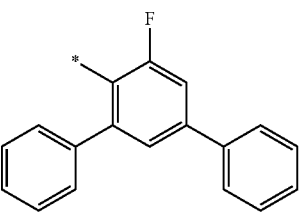

Formula 3V 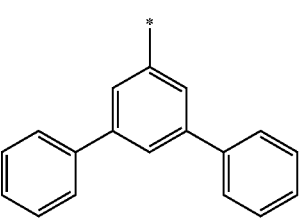

Formula 3W 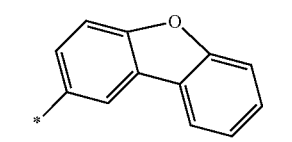

wherein * is a binding site.

5. The condensed-cyclic compound of claim 1, wherein A and B are each independently a substituted or unsubstituted phenylene group, a substituted or unsubstituted naphthylene group, a substituted or unsubstituted fluorenylene group, a substituted or unsubstituted carbazolylene group, a substituted or unsubstituted dibenzofurylene group, a substituted or unsubstituted dibenzothiophenylene group, a substituted or unsubstituted pyridylene group, a substituted or unsubstituted pyrimidinylene group, a substituted or unsubstituted triazinylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted furylene group, a substituted or unsubstituted thiophenylene group, or a substituted or unsubstituted oxadiazolylene group.

6. The condensed-cyclic compound of claim 1, wherein A and B are each independently a group represented by one of Formulae 4A to 4G:

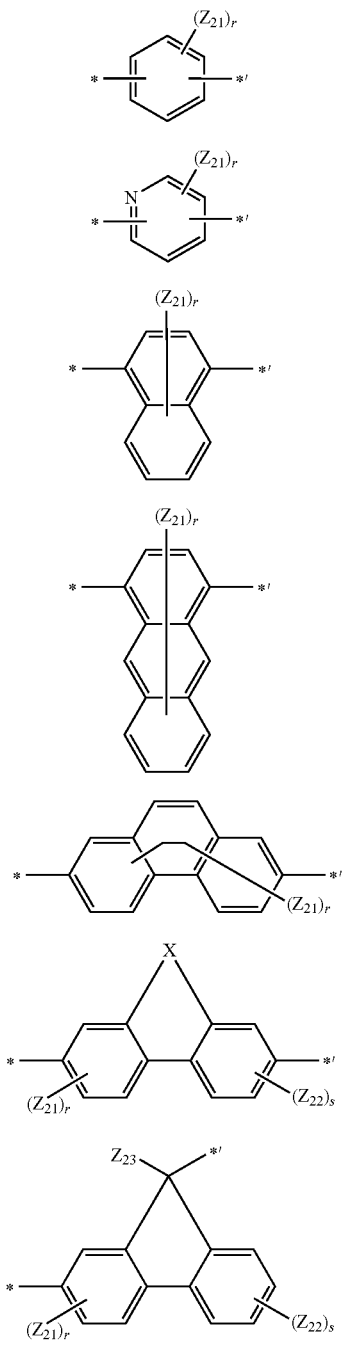

wherein X is O, S, N($Z_{23}$), or C($Z_{24}$)($Z_{25}$);

$Z_{21}$, $Z_{22}$, $Z_{23}$, $Z_{24}$ and $Z_{25}$ are each independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, or a substituted or unsubstituted pyridyl group, wherein a plurality of each of $Z_{21}$ and/or $Z_{22}$ are identical to or different from each other;

r is an integer from 1 to 8;

s is an integer from 1 to 4; and

* and *' are binding sites.

7. The condensed-cyclic compound of claim 6, wherein A and B are each independently a group represented by one of Formulae 5A to 5N:

Formula 5A

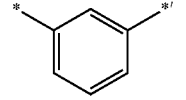

Formula 5B

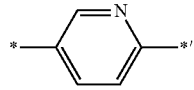

Formula 5C

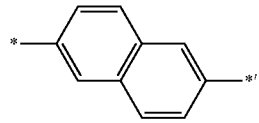

Formula 5D

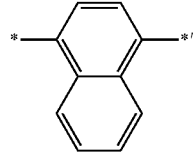

Formula 5E

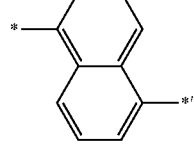

Formula 5F

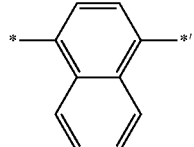

Formula 5G

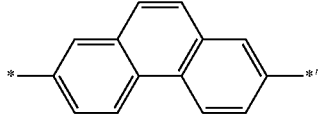

Formula 5H

-continued

Formula 5I
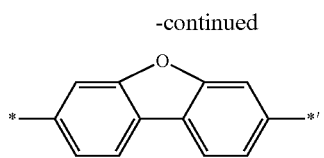

Formula 5J
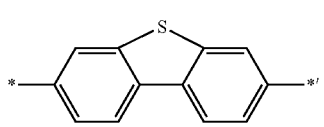

Formula 5K
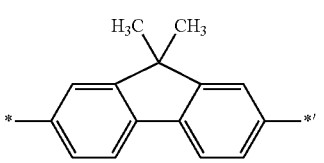

Formula 5L
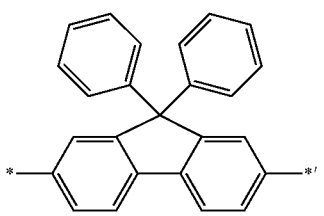

Formula 5M
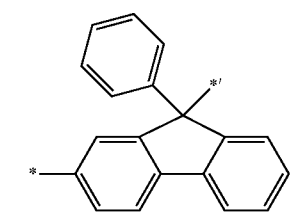

Formula 5N
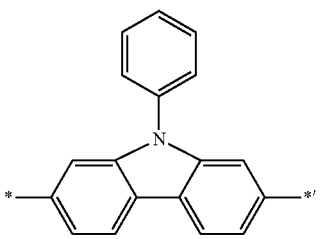

wherein * and *' are binding sites.

8. The condensed-cyclic compound of claim 1, wherein $R_1$ and $R_{13}$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted cyclohexyl group, a substituted or unsubstituted ethenyl group, a substituted or unsubstituted phenyl group, a substituted or unsubstituted naphthyl group, a substituted or unsubstituted fluorenyl group, a substituted or unsubstituted carbazolyl group, a substituted or unsubstituted dibenzofuryl group, a substituted or unsubstituted dibenzothiophenyl group, a substituted or unsubstituted pyridyl group, a substituted or unsubstituted pyrimidinyl group, a substituted or unsubstituted triazinyl group, a substituted or unsubstituted anthryl group, a substituted or unsubstituted phenanthrenyl group, a substituted or unsubstituted pyrenyl group, a substituted or unsubstituted chrysenyl group, a substituted or unsubstituted perylenyl group, a substituted or unsubstituted furyl group, a substituted or unsubstituted thiophenyl group, or a substituted or unsubstituted oxadiazolyl group.

9. The condensed-cyclic compound of claim 1, wherein $R_1$ and $R_{13}$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted cyclohexyl group, or a group represented by one of Formulae 6A to 6F:

Formula 6A
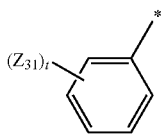

Formula 6B
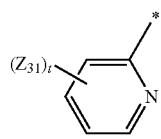

Formula 6C
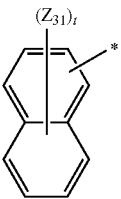

Formula 6D
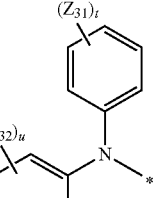

Formula 6E
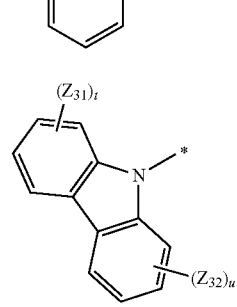

Formula 6F

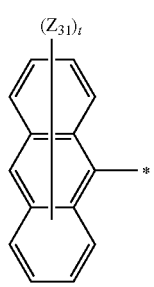

wherein $Z_{31}$ and $Z_{32}$ are each independently a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, or a substituted or unsubstituted pyridyl group, wherein a plurality of each of $Z_{31}$ and/or $Z_{32}$ are identical to or different from each other;

t is an integer from 1 to 7;
u is an integer from 1 to 4; and
* is a binding site.

10. The condensed-cyclic compound of claim 9, wherein $R_1$ and $R_{13}$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted cyclohexyl group, or a group represented by one of Formulae 7A to 7G:

Formula 7A
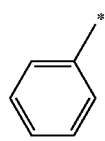

Formula 7B
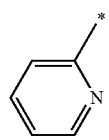

Formula 7C
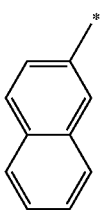

Formula 7D
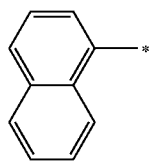

Formula 7E
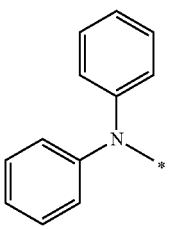

Formula 7F
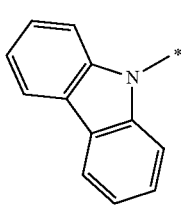

Formula 7G
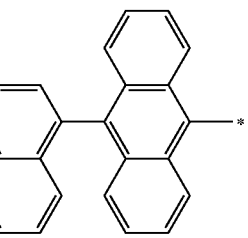

wherein * is a binding site.

11. The condensed-cyclic compound of claim 1, wherein the condensed-cyclic compound of Formula 1 is one of compounds 6, 18, 19, 26, 30, 53, 65 or 80:

6

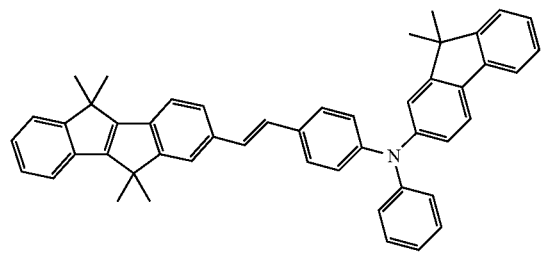

18

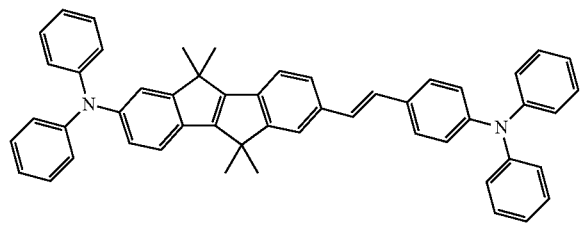

-continued

19

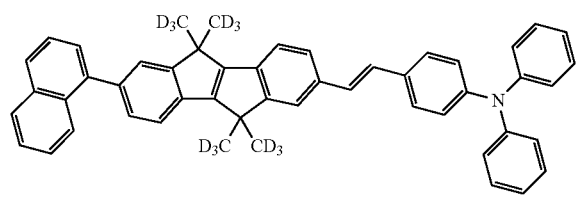

26

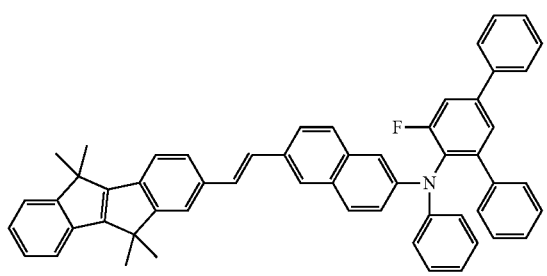

30

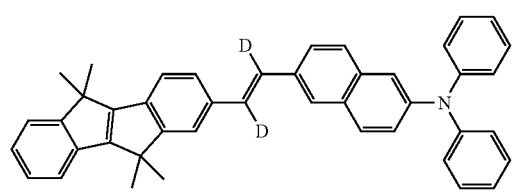

53

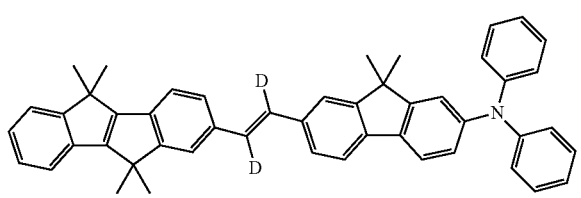

65

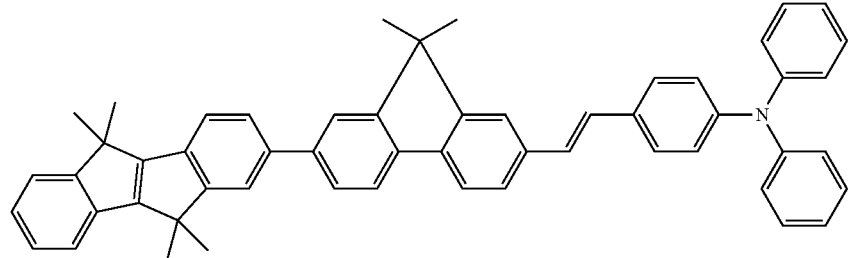

80

45

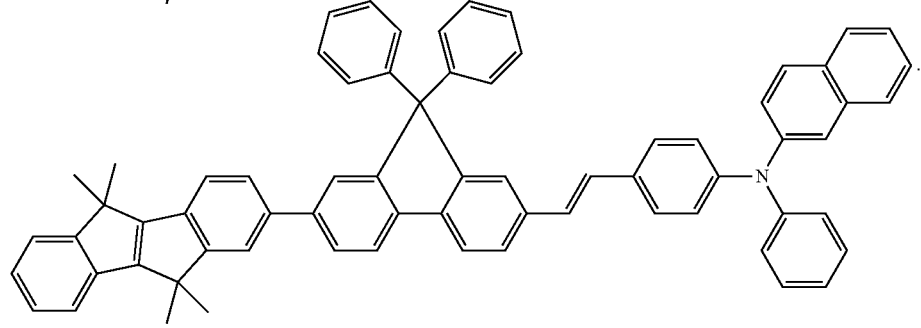

12. An organic light-emitting device comprising:
a first electrode;
a second electrode facing the first electrode; and
an organic layer between the first electrode and the second electrode, wherein the organic layer comprises at least one layer, and comprises at least one condensed-cyclic compound according to claim 1.

13. The organic light-emitting device of claim 12, wherein the organic layer comprises at least one of a hole injection layer, a hole transport layer, a hole injection and transport layer having both hole injection and hole transport capabilities, an emission layer, an electron injection layer, an electron transport layer, or an electron injection and transport layer having both electron injection and electron transport capabilities.

14. The organic light-emitting device of claim 13, wherein at least one selected from the emission layer, the hole injection layer, the hole transport layer, and the hole injection and transport layer further comprises the condensed-cyclic compound represented by Formula 1.

15. The organic light-emitting device of claim 12, wherein the organic layer comprises an emission layer, the emission layer comprises a host and a dopant, and the condensed-cyclic compound represented by Formula 1 is a fluorescent host or a phosphorescent host of the emission layer.

16. The organic light-emitting device of claim 12, wherein the organic layer comprises an emission layer, the emission layer comprises a host and a dopant, and the condensed-cyclic compound represented by Formula 1 is a fluorescent dopant of the emission layer.

17. The organic light-emitting device of claim 13, wherein at least one selected from the hole injection layer, the hole transport layer, and the hole injection and transport layer further comprises a charge-generating material.

18. The organic light-emitting device of claim 17, wherein the charge-generating material is a p-type dopant.

19. The organic light-emitting device of claim 12, wherein the organic layer comprises an electron transport layer, and the electron transport layer comprises an electron transporting organic compound and a metal-containing material.

20. The organic light-emitting device of claim 19, wherein the metal-containing material includes a lithium (Li) complex.

* * * * *